US012729226B2

(12) United States Patent
Kikuchi, III et al.

(10) Patent No.: US 12,729,226 B2
(45) Date of Patent: Sep. 8, 2026

(54) KLF INDUCED CARDIOMYOGENESIS

(71) Applicants: Victor Chang Cardiac Research Institute, Sydney (AU); National Cerebral and Cardiovascular Center, Osaka (JP)

(72) Inventors: Kazu Kikuchi, III, Sydney (AU); Masahito Ogawa, Sydney (AU)

(73) Assignees: Victor Chang Cardiac Research Institute, Sydney (AU); National Cerebral and Cardiovascular Center, Osaka (JP)

( * ) Notice: Subject to any disclaimer, the term of this patent is extended or adjusted under 35 U.S.C. 154(b) by 958 days.

(21) Appl. No.: 17/630,263

(22) PCT Filed: Jul. 30, 2020

(86) PCT No.: PCT/AU2020/050775
§ 371 (c)(1),
(2) Date: Jan. 26, 2022

(87) PCT Pub. No.: WO2021/016663
PCT Pub. Date: Feb. 4, 2021

(65) Prior Publication Data

US 2023/0192784 A1 Jun. 22, 2023

(30) Foreign Application Priority Data

Jul. 30, 2019 (AU) ................................ 2019902703

(51) Int. Cl.

| | |
|---|---|
| ***C07K 14/47*** | (2006.01) |
| ***A61K 35/34*** | (2015.01) |
| ***A61K 38/17*** | (2006.01) |
| ***A61P 9/00*** | (2006.01) |
| ***C12N 5/077*** | (2010.01) |

(52) U.S. Cl.
CPC .......... *C07K 14/4702* (2013.01); *A61K 35/34* (2013.01); *A61K 38/1709* (2013.01); *A61P 9/00* (2018.01); *C12N 5/0657* (2013.01)

(58) Field of Classification Search
None
See application file for complete search history.

(56) References Cited

U.S. PATENT DOCUMENTS

2012/0009158 A1 1/2012 Chien et al.

FOREIGN PATENT DOCUMENTS

WO 2011/157029 A1 12/2011
WO 2012/067266 A1 5/2012

OTHER PUBLICATIONS

International Search Report issued in corresponding International Patent Application No. PCT/AU2020/050775 dated Aug. 21, 2020.
Azeez, et al. “Homology-Based Structure Prediction of the Human Kruppel-Like Factor 1 Protein,” International Journal of Current Microbiology and Applied Sciences, vol. 7, No. 6, pp. 2169-2176.
Ireland, et al., “ZincBind—the database of zinc binding sites,” Database, 8 pages, 2019.

*Primary Examiner* — Christina Bradley
(74) *Attorney, Agent, or Firm* — Morgan, Lewis & Bockius LLP

(57) ABSTRACT

The technology relates to a method for inducing cardiomyogenesis comprising administering a therapeutically effective amount of either or both of KLF1 and KLF2b to increase the level of KLF1 and/or KLF2b in the cardiomyocytes thereby inducing cardiomyogenesis.

18 Claims, 41 Drawing Sheets

Specification includes a Sequence Listing.

A
Muscle Fibrin Collagen
KftDN-OFF
30 dpi
0/7
KftDN-ON
30 dpi
7/7
B
Ventricles
7 dpi
Mef2+PCNA+ (%)
20
15
10
5
0
*
OFF
ON A
Relative expression
4
2
0
7d OFF
7d ON
**
runx1
B
Relative expression
2
1
0
7d OFF
7d ON
**
**
*
vmhc
actc1a
myom2a

A

Right arm cloning site

Left arm cloning site

Zwitch2

Lens tag

3xBGHpA

*FRT* *loxP* *lox5171* Splice acceptor

B

C

D

G

H

A

B

A

B

C D

E

F

G

H

I

A

B

H

I

SEQUENCE LISTING

<160> NUMBER OF SEQ ID NOS: 12

<210> SEQ ID NO 1
<211> LENGTH: 362
<212> TYPE: PRT
<213> ORGANISM: Homo sapiens

<400> SEQUENCE: 1

Met Ala Thr Ala Glu Thr Ala Leu Pro Ser Ile Ser Thr Leu Thr Ala
1 5 10 15

Leu Gly Pro Phe Pro Asp Thr Gln Asp Asp Phe Leu Lys Trp Trp Arg
20 25 30

Ser Glu Glu Ala Gln Asp Met Gly Pro Gly Pro Pro Asp Pro Thr Glu
35 40 45

Pro Pro Leu His Val Lys Ser Glu Asp Gln Pro Gly Glu Glu Glu Asp
50 55 60

Asp Glu Arg Gly Ala Asp Ala Thr Trp Asp Leu Asp Leu Leu Leu Thr
65 70 75 80

Asn Phe Ser Gly Pro Glu Pro Gly Gly Ala Pro Gln Thr Cys Ala Leu
85 90 95

Ala Pro Ser Glu Ala Ser Gly Ala Gln Tyr Pro Pro Pro Pro Glu Thr
100 105 110

Leu Gly Ala Tyr Ala Gly Gly Pro Gly Leu Val Ala Gly Leu Leu Gly
115 120 125

Ser Glu Asp His Ser Gly Trp Val Arg Pro Ala Leu Arg Ala Arg Ala
130 135 140

Pro Asp Ala Phe Val Gly Pro Ala Leu Ala Pro Ala Pro Ala Pro Glu
145 150 155 160

Pro Lys Ala Leu Ala Leu Gln Pro Val Tyr Pro Gly Pro Gly Ala Gly
165 170 175

Ser Ser Gly Gly Tyr Phe Pro Arg Thr Gly Leu Ser Val Pro Ala Ala
180 185 190

Ser Gly Ala Pro Tyr Gly Leu Leu Ser Gly Tyr Pro Ala Met Tyr Pro
195 200 205

Ala Pro Gln Tyr Gln Gly His Phe Gln Leu Phe Arg Gly Leu Gln Gly
210 215 220

Pro Ala Pro Gly Pro Ala Thr Ser Pro Ser Phe Leu Ser Cys Leu Gly
225 230 235 240

Pro Gly Thr Val Gly Thr Gly Leu Gly Gly Thr Ala Glu Asp Pro Gly
245 250 255

Val Ile Ala Glu Thr Ala Pro Ser Lys Arg Gly Arg Arg Ser Trp Ala
260 265 270

Arg Lys Arg Gln Ala Ala His Thr Cys Ala His Pro Gly Cys Gly Lys
275 280 285

Ser Tyr Thr Lys Ser Ser His Leu Lys Ala His Leu Arg Thr His Thr
290 295 300

Gly Glu Lys Pro Tyr Ala Cys Thr Trp Glu Gly Cys Gly Trp Arg Phe
305 310 315 320

Ala Arg Ser Asp Glu Leu Thr Arg His Tyr Arg Lys His Thr Gly Gln
325 330 335

Arg Pro Phe Arg Cys Gln Leu Cys Pro Arg Ala Phe Ser Arg Ser Asp
340 345 350

His Leu Ala Leu His Met Lys Arg His Leu
355 360

<210> SEQ ID NO 2
<211> LENGTH: 1645
<212> TYPE: DNA
<213> ORGANISM: Homo sapiens

<400> SEQUENCE: 2

```
tcagagttca cgaggcagcc gaggaagagg aggcttgagg cccagggtgg gcaccagcca     60

gccatggcca cagccgagac cgccttgccc tccatcagca cactgaccgc cctgggcccc    120

ttcccggaca cacaggatga cttcctcaag tggtggcgct ccgaagaggc gcaggacatg    180

ggcccgggtc ctcctgaccc cacggagccg cccctccacg tgaagtctga ggaccagccc    240

ggggaggaag aggacgatga gaggggcgcg gacgccacct gggacctgga tctcctcctc    300

accaacttct cgggcccgga gcccggtggc gcgccccaga cctgcgctct ggcgcccagc    360

gaggcctccg ggcgcaata tccgccgccg cccgagactc tgggcgcata tgctggcggc    420

ccggggctgg tggctgggct tttgggttcg gaggatcact cgggttgggt gcgccctgcc    480

ctgcgagccc gggctcccga cgccttcgtg ggcccagccc tggctccagc cccggccccc    540

gagcccaagg cgctggcgct gcaaccggtg tacccggggc ccggcgccgg ctcctcgggt    600

ggctacttcc cgcggaccgg gctttcagtg cctgcggcgt cgggcgcccc ctacgggcta    660

ctgtccgggt accccgcgat gtacccggcg cctcagtacc aagggcactt ccagctcttc    720

cgcgggctcc agggacccgc gcccggtccc gccacgtccc cctccttcct gagttgtttg    780

ggacccggga cggtgggcac tggactcggg gggactgcag aggatccagg tgtgatagcc    840

gagaccgcgc catccaagcg aggccgacgt tcgtgggcgc gcaagaggca ggcagcgcac    900

acgtgcgcgc acccgggttg cggcaagagc tacaccaaga gctcccacct gaaggcgcat    960

ctgcgcacgc acacagggga gaagccatac gcctgcacgt gggaaggctg cggctggaga   1020

ttcgcgcgct cggacgagct gacccgccac taccggaaac acacggggca gcgccccttc   1080

cgctgccagc tctgcccacg tgctttttcg cgctctgacc acctggcctt gcacatgaag   1140

cgccaccttt gagccctgcc ctggcacttg gactctccta gtgactgggg atgggacaag   1200

aagcctgttt ggtggtctct tcacacggac gcgcgtgaca caatgctggg tggttttccc   1260

acgaatggac cctctcctgg actcgcgttc ccaaagatcc acccaaatat caaacacgga   1320

cccatagaca gccctggggg agcctcttac ggaaaatccg acaagccttc agccacaggg   1380

agccacacag agatgtccaa actgtcgtgc aaacccagtg agacagaccg ccaaataaac   1440

ggactcagtg gacactcaga ccagctccca gatggccctg gacagcagga gagggtgtgg   1500

gatgaggctt cccagagacc ctgggtctag aaagcggctc ctgaaggtcc cttattgtgg   1560

ctgatattaa ctgtcaatgg ttatgggtcc tataaaaatg cccctcccag ataaaaaaaa   1620

aaaaaaaaaa aaaaaaaaaa aaaaa                                         1645
```

<210> SEQ ID NO 3
<211> LENGTH: 1089
<212> TYPE: DNA
<213> ORGANISM: Homo sapiens

<400> SEQUENCE: 3

```
atggccacag ccgagaccgc cttgccctcc atcagcacac tgaccgccct gggccccttc     60

ccggacacac aggatgactt cctcaagtgg tggcgctccg aagaggcgca ggacatgggc    120

ccgggtcctc ctgaccccac ggagccgccc ctccacgtga agtctgagga ccagcccggg    180

gaggaagagg acgatgagag gggcgcggac gccacctggg acctggatct cctcctcacc    240
```

```
aacttctcgg gcccggagcc cggtggcgcg ccccagacct gcgctctggc gcccagcgag    300

gcctccgggg cgcaatatcc gccgccgccc gagactctgg gcgcatatgc tggcggcccg    360

gggctggtgg ctgggctttt gggttcggag gatcactcgg gttgggtgcg ccctgccctg    420

cgagcccggg ctcccgacgc cttcgtgggc ccagccctgg ctccagcccc ggcccccgag    480

cccaaggcgc tggcgctgca accggtgtac ccggggcccg gcgccggctc ctcgggtggc    540

tacttcccgc ggaccgggct ttcagtgcct gcggcgtcgg gcgcccccta cgggctactg    600

tccgggtacc ccgcgatgta cccggcgcct cagtaccaag ggcacttcca gctcttccgc    660

gggctccagg gacccgcgcc cggtcccgcc acgtccccct ccttcctgag ttgtttggga    720

cccgggacgg tgggcactgg actcgggggg actgcagagg atccaggtgt gatagccgag    780

accgcgccat ccaagcgagg ccgacgttcg tgggcgcgca agaggcaggc agcgcacacg    840

tgcgcgcacc cgggttgcgg caagagctac accaagagct cccacctgaa ggcgcatctg    900

cgcacgcaca caggggagaa gccatacgcc tgcacgtggg aaggctgcgg ctggagattc    960

gcgcgctcgg acgagctgac ccgccactac cggaaacaca cggggcagcg ccccttccgc   1020

tgccagctct gcccacgtgc tttttcgcgc tctgaccacc tggccttgca catgaagcgc   1080

cacctttga                                                          1089
```

```
<210> SEQ ID NO 4
<211> LENGTH: 1476
<212> TYPE: DNA
<213> ORGANISM: Mus musculus

<400> SEQUENCE: 4

agaagagaga gaggaggcct gaggtccagg gtggacacca gccagccatg gcctcagctg     60

agactgtctt accctccatc agtacactca ccaccctggg acagttcctg gacacccagg    120

aggacttcct caagtggtgg cggtctgagg agacgcagga tttggggccg gggcccccga    180

atcccacggg gccgtcccat cacgtgagtc tgaaatcgga ggacccttcc ggagaggacg    240

atgagaggga cgtgacctgt gcgtgggacc cggatctttt ccttacaaac tttccaggtt    300

ccgagtctcc cggcacttcc cggacctgtg ccctggcgcc cagcgtgggg ccagtggcac    360

agttcgagcc gcctgagtct ctgggcgcct atgcgggtgg cccagggttg gtgactgggc    420

ctttgggctc cgaggagcac acaagctggg cgcacccgac tccgagaccc ccagcccctg    480

aacccttcgt ggcccctgcc ctggccccgg gactcgctcc caaggctcag ccctcgtact    540

ccgactcgcg agcgggctcc gtagggggct tcttcccgcg ggcggggctt gcggtgcccg    600

cagctccagg cgccccctat gggctgctgt cgggataccc cgcgctgtac cccgcgccac    660

agtaccaagg ccacttccag ctctttcgcg ggctcgcggc gccttctgct ggtcccacgg    720

cgccccccttc cttcttgaat tgtctgggac ctgggactgt ggccacagaa ctcggggcca    780

ctgcgatcgc cggagacgca ggcttgtccc cgggaactgc gccgcccaaa cgcagccggc    840

gaactttggc acctaagagg caggcggcac atacgtgcgg gcacgaaggc tgcgggaaga    900

gctacaccaa gagctcgcac ctcaaggcgc acctgcgcac gcacacggga gagaagcctt    960

atgcctgctc ctgggacggc tgtgactgga ggttcgctcg ctcagacgaa ctgacgcgcc   1020

actaccggaa gcacactgga catcgtccct tctgctgtgg cctctgccca cgtgcttttt   1080

cacgctctga ccacttagct ctgcacatga agcgtcacct ctgagtgatc ctgcacaagg   1140

actggggatg aaataagagt ggatccaagg accgtatccc aaaagatggg ccattatata   1200
```

```
gtcctaccca gatcaaaaac tgaccagaag accatacaaa ggagccttca ggacaaacct   1260

cacatgtcct cagggagccc cacacatggc cccacagacc cagcaatata gaccaccaga   1320

taaatcaact caaatggacc cctagaccag aggagtgacc ctgtgtcctg gacgcagatg   1380

gactggggtg agatttccta agatctagaa gggagcttca cactgtgccc atctgctagg   1440

attgttgtcg ttactataaa aatttcccat ataaaa                             1476
```

<210> SEQ ID NO 5
<211> LENGTH: 1077
<212> TYPE: DNA
<213> ORGANISM: Mus musculus

<400> SEQUENCE: 5

```
atggcctcag ctgagactgt cttaccctcc atcagtacac tcaccaccct gggacagttc     60

ctggacaccc aggaggactt cctcaagtgg tggcggtctg aggagacgca ggatttgggg    120

ccggggcccc cgaatcccac ggggccgtcc catcacgtga gtctgaaatc ggaggaccct    180

tccggagagg acgatgagag ggacgtgacc tgtgcgtggg acccggatct tttccttaca    240

aactttccag gttccgagtc tcccggcact tcccggacct gtgccctggc gcccagcgtg    300

gggccagtgg cacagttcga gccgcctgag tctctgggcg cctatgcggg tggcccaggg    360

ttggtgactg ggcctttggg ctccgaggag cacacaagct gggcgcaccc gactccgaga    420

cccccagccc ctgaaccctt cgtggcccct gccctggccc cgggactcgc tcccaaggct    480

cagccctcgt actccgactc gcgagcgggc tccgtagggg gcttcttccc gcgggcgggg    540

cttgcggtgc ccgcagctcc aggcgccccc tatgggctgc tgtcgggata ccccgcgctg    600

taccccgcgc cacagtacca aggccacttc cagctctttc gcgggctcgc ggcgccttct    660

gctggtccca cggcgccccc ttccttcttg aattgtctgg gacctgggac tgtggccaca    720

gaactcgggg ccactgcgat cgccggagac gcaggcttgt ccccgggaac tgcgccgccc    780

aaacgcagcc ggcgaacttt ggcacctaag aggcaggcgg cacatacgtg cgggcacgaa    840

ggctgcggga agagctacac caagagctcg cacctcaagg cgcacctgcg cacgcacacg    900

ggagagaagc cttatgcctg ctcctgggac ggctgtgact ggaggttcgc tcgctcagac    960

gaactgacgc gccactaccg gaagcacact ggacatcgtc ccttctgctg tggcctctgc   1020

ccacgtgctt tttcacgctc tgaccactta gctctgcaca tgaagcgtca cctctga      1077
```

<210> SEQ ID NO 6
<211> LENGTH: 363
<212> TYPE: PRT
<213> ORGANISM: Danio rerio

<400> SEQUENCE: 6

```
Met Ala Leu Pro Cys Leu Leu Pro Ser Ile Ser Thr Phe Ala Asn Gln
1               5                   10                  15

Lys Glu Lys Leu Trp Glu Asp Arg Trp Lys Ile Glu Glu His Lys Pro
            20                  25                  30

Leu Asn Ala Ser Cys Pro Pro Leu Asn Val Ala Leu Asn Thr Asp Thr
        35                  40                  45

Cys Arg Gly Arg Lys Asp Asp Glu Asp Leu Ser Asn Tyr Leu Asp Leu
    50                  55                  60

Glu Phe Ile Leu Ala Asn Thr Thr Gly Pro Leu Glu Ala Gly Ala Glu
65                  70                  75                  80

Phe Ile Ser His Ser Glu Pro Cys Gly Met Tyr Ser Thr Ala Val Tyr
                85                  90                  95
```

```
Ser Ser Pro Glu Ala Pro Pro Pro Tyr Gly Leu Met Ala Glu Leu Leu
            100                 105                 110

Arg Ser Asp Val Asp Ser Thr Tyr Asp Thr Thr Val Gln Gly Arg Phe
        115                 120                 125

Leu Leu Asn Ser Ser Gly Phe Pro Arg Gln Glu Phe Pro Glu Ile Lys
    130                 135                 140

Val Glu Pro Pro Met Asp Gly Tyr Gly Pro Val Ile Gly Met Val Pro
145                 150                 155                 160

Gln Thr Cys Gln Lys Ile Lys Gln Glu Gly Asn Val Ser Cys Met Met
                165                 170                 175

Ser Phe Glu Gln Pro Arg Leu Ala Val Ser Pro Gln Ala Thr Gly Asn
            180                 185                 190

Met Thr Pro Pro Leu Ser Pro Asp Asp Ser His Leu Arg Gln Thr Thr
        195                 200                 205

Tyr Thr Gln Ser Tyr His His Ser Pro Pro Ala Tyr Pro Gln Val Pro
    210                 215                 220

Met Gln Phe Thr Ala Pro His Gln Phe Ala Met Tyr Glu Glu Ala Met
225                 230                 235                 240

Gly Met Gln Pro Ser Met Gln Arg Ala Leu Leu Thr Pro Pro Ser Ser
                245                 250                 255

Pro Leu Glu Leu Met Glu Ser Lys Pro Lys Arg Gly Arg Arg Thr Trp
            260                 265                 270

Pro Arg Lys Arg Met Ala Thr His Thr Cys Thr Tyr Ala Gly Cys Gly
        275                 280                 285

Lys Thr Tyr Thr Lys Ser Ser His Leu Lys Ala His His Arg Thr His
    290                 295                 300

Thr Gly Glu Lys Pro Tyr His Cys Asn Trp Glu Gly Cys Gly Trp Lys
305                 310                 315                 320

Phe Ala Arg Ser Asp Glu Leu Thr Arg His Phe Arg Lys His Thr Gly
                325                 330                 335

His Arg Pro Phe Gln Cys His Leu Cys Glu Arg Ala Phe Ser Arg Ser
            340                 345                 350

Asp His Leu Ala Leu His Met Lys Arg His Leu
        355                 360


<210> SEQ ID NO 7
<211> LENGTH: 3573
<212> TYPE: DNA
<213> ORGANISM: Danio rerio

<400> SEQUENCE: 7

ggcacgaggc gcactgtgcc ttatatatag actatctttg ggaactctga acgcggtttc      60

caccgcgcac acaattggtc taggagccgt atttattaag taggaggcgc tccagccggg     120

caaactttgt tcatgactgt ggaagttcac tcgaggaaaa agcgcgcaga cgtttgacat     180

ctcttcagga gcaagtgcat taatactgaa tacacaccga gcacgcgtgg acatggcttt     240

accttgcctt ttgccttcga tttcaacgtt tgcaaaccag aaggagaagc tctgggagga     300

tagatggaag attgaggagc acaaaccact gaacgccagc tgccctccgc tcaacgtggc     360

actgaacaca gacacttgtc gaggccgcaa ggatgacgag gatctcagca attatttaga     420

cctggagttt atcctggcca acaccacggg ccctctggag gccggagccg agttcatctc     480

ccactccgag ccatgcggca tgtactccac tgcagtttac tcatctccag aagcacctcc     540

accatacggc ctcatggcag agctcctgcg atctgatgta gactccacgt atgacaccac     600
```

-continued

```
agtgcagggg agattcctgc tcaactccag cggcttcccc agacaggagt ttcctgaaat    660
caaagtggag ccgccgatgg atggctacgg tccggtgata ggcatggtgc cacaaacctg    720
ccaaaaaatc aagcaggaag gcaacgtttc atgcatgatg tctttcgagc agcccagact    780
agcagtttct ccgcaggcca ccgggaatat gactcctccg ctgagtcctg acgactccca    840
cctccgtcaa acgacatata cacagagcta ccatcactct cctccggcgt atccgcaggt    900
gccaatgcag ttcacagcgc cacaccagtt tgccatgtat gaggaggcaa tggggatgca    960
acccagcatg cagcgggctc ttctcacccc tccgtcctct ccgttagagc taatggagtc   1020
caaacccaag cgagggcgac gcacctggcc gaggaagcgc atggcgacac atacatgcac   1080
gtacgccggc tgcgggaaga cgtacaccaa aagctcccat ttaaaagcgc atcaccgcac   1140
tcacaccggt gaaaaaccat accactgcaa ctgggaggga tgcggatgga agttcgcccg   1200
ttctgacgag ctgacgcgtc acttccgtaa acacacgggc caccggccgt tccagtgcca   1260
cctgtgtgaa cgtgccttct cccgctccga ccacctggcg ctgcacatga agagacacct   1320
gtgagggccg gatccaccac aactgcctta tttaatgact cttattatat atatatatca   1380
tcatactttt ataacaaagt agctggtact acatagatca cgcagagctc tttttaaggc   1440
cttttttttgg ggttaaaaag catcctgaaa ggctggtcct acgaatcggt gtccaatccg   1500
gagactgtta tgttgaatta acgatgccac aacgagtgca aagcctgacg actagcaaac   1560
caaagtggaa aatgcacaac gatgttgaca atgttttgct cgaaactgcc atgcaacaaa   1620
tgtgtttcat ttttaccagg gctgggagga taaaatcatt attgtgaatc aagaaatgat   1680
tcctacattt tctgaatgca ttgcgatttc cttttgaatc gatttgaagc ttagttttta   1740
ccaccagagg gcactgtatg ctttacacat acaatttaaa tgtaaaacaa ttattaatac   1800
atacatttgt acataaacta gcctagacct ctgttaaaag ttaacctata gtgcgtctgc   1860
tgttaaaaac tagcctagag cgccctctag tgttaaaaac tagcctagag tactgtctgg   1920
tgtttacaaa ctagtctaga gcttcatcta ctgttcaaac ctagcctaga cctctgttaa   1980
agattaacct atagtgcttc tgctgttaaa aactagcata gagctgcctc tggtgttaaa   2040
aactagccta gagtgtcatc tgctgtttga aaactagcct agagtgcatt cttctgctca   2100
aaactagcct tgacctctgt taaaattagc ctatagtgcg tctgctgtta aaaactagcc   2160
tagagcgcca tctggtgtta aaaactagcc tagagcgccc tctgctgctc aaaactaacc   2220
taaacctctg ttaaaaatta gcctatatag tgtctggtgt taaacactag tctagactgc   2280
cctctgatgt taaaaaaact agcctagagt gccttttgtt gcttaaaact agcctagacc   2340
tcagtttaaa aattagccta cagtgcatct gctgataaaa actagcctag agcgctctca   2400
ggtgttaaaa actagcctag agtgccgtct gcttctcaaa aactagccta gagttgattc   2460
ctttgctcaa aactagccta gacctctgtt aaaaaattag cctatagtgc gtctgctgtt   2520
acaaactagc ccagaacatc atctggtgtt aataactagc ctagagcgcc atctgctgct   2580
cagaactagc ctagacctct gttaaaaatt agcctttagt gcgtctccgg ttaaaaacta   2640
gcctagagcg ccctctagtg ttaaaaacta gtctagagcg ccctctgctg cacaaaatta   2700
gcctaaacct ctgttaaaat tagacaagag tgcgtttgct ggtaaaaact agcatagagc   2760
accctctggt gttaaaatct agcctagagc acactgtggt gttaaaaact agccaagagc   2820
gccatttgca gttcaaaact agcctagatt gctgttaaac attagtctag attccatatg   2880
ctgttataaa ctcacctaga gcgccatctg ctgtcaaaaa acccacctag agcgccatct   2940
```

```
gctgttaaaa acggatctta gaattgattc catagagaat cgggacgcag ttaaaaatct   3000

aacaatcgat tcatgaataa caatacaatg atttatcaat tccagcccta attttttaca   3060

tatttctttc caaatgttgg taacgcttta caataatgct gcatttagta aatgcattga   3120

gcaaaaaaaa gtgtgtaatt taggtgcatt ggatcacacc aacagatgca acttttgtaa   3180

gtgttaaagg gacggctcac tccaaaaatg aagatgacct ccattgactt taatagtaat   3240

tgttttttta tcctatggaa gtcagtggag accatcaagt agcattcttc aaaatatctt   3300

ctgtagtgtt taacagatga aaagagtgag tgaatgatga cagatctaat tccttgtgtg   3360

aactatccct ttaacgcatg ttccctattg taaaacattc ctcaaacggc ggcacattca   3420

gtgtcctctt gttcaatagc accggatgcg ctgggtcttg aagtcctggg tcttttttta   3480

tatgattgtg tacatacatt ttatattgta agtactgtat ttattgtaaa tattaaacta   3540

aatttgaata taaaaaaaaa aaaaaaaaaa aaa                                3573
```

<210> SEQ ID NO 8
<211> LENGTH: 1092
<212> TYPE: DNA
<213> ORGANISM: Danio rerio

<400> SEQUENCE: 8

```
atggctttac cttgcctttt gccttcgatt tcaacgtttg caaaccagaa ggagaagctc     60

tgggaggata gatggaagat tgaggagcac aaaccactga acgccagctg ccctccgctc    120

aacgtggcac tgaacacaga cacttgtcga ggccgcaagg atgacgagga tctcagcaat    180

tatttagacc tggagtttat cctggccaac accacgggcc ctctggaggc cggagccgag    240

ttcatctccc actccgagcc atgcggcatg tactccactg cagtttactc atctccagaa    300

gcacctccac catacggcct catggcagag ctcctgcgat ctgatgtaga ctccacgtat    360

gacaccacag tgcaggggag attcctgctc aactccagcg gcttccccag acaggagttt    420

cctgaaatca aagtggagcc gccgatggat ggctacggtc cggtgatagg catggtgcca    480

caaacctgcc aaaaaatcaa gcaggaaggc aacgtttcat gcatgatgtc tttcgagcag    540

cccagactag cagtttctcc gcaggccacc gggaatatga ctcctccgct gagtcctgac    600

gactcccacc tccgtcaaac gacatataca cagagctacc atcactctcc tccggcgtat    660

ccgcaggtgc caatgcagtt cacagcgcca caccagtttg ccatgtatga ggaggcaatg    720

gggatgcaac ccagcatgca gcgggctctt ctcacccctc cgtcctctcc gttagagcta    780

atggagtcca aacccaagcg agggcgacgc acctggccga ggaagcgcat ggcgacacat    840

acatgcacgt acgccggctg cgggaagacg tacaccaaaa gctcccattt aaaagcgcat    900

caccgcactc acaccggtga aaaaccatac cactgcaact gggagggatg cggatggaag    960

ttcgcccgtt ctgacgagct gacgcgtcac ttccgtaaac acacgggcca ccggccgttc   1020

cagtgccacc tgtgtgaacg tgccttctcc cgctccgacc acctggcgct gcacatgaag   1080

agacacctgt ga                                                       1092
```

<210> SEQ ID NO 9
<211> LENGTH: 2532
<212> TYPE: DNA
<213> ORGANISM: Danio rerio

<400> SEQUENCE: 9

```
ggcacgagga taaagtaacc tttaatggca ctgtgaagtt ttatgtaaat atatttgact     60

ttaacactaa attctgggtt cttacccttt gtgtattgca catgtaaata aatacaattc    120
```

```
tggacaaata tcaaacactc tatttggaga caattgtttg tgtaataaat gctgaaaggg    180
caccaaacgg atggctgtga ctcaagccgt actgccttca ttttcaaact tctgcaccaa    240
ctccgaaaac atgaagtttg aaaaaggctt tctggatctg gactccaagg atctgcacca    300
aagcccagcc agctacaaac cttcccagtt cctgactgat gagcaccagg acgacagcga    360
gggatgctgg gacatggagt tcctactgtc tgactgggcc agtatgtcac ctgaacggtc    420
caactctcaa aactacactc cccagcggcc gaccctacag gaccagcttc acagtccaga    480
tctttatcag gagctgaacg caccaaaacc aaacagacat caagtgtgcg ttgcaagttc    540
cctagctgag ctgcttcctc ctgaagcaac cttaagttcc tccctgcctc ctgacctcca    600
gtttaattgt ggatttctag atcaacaagc tgccaaatca tattcccagg cagaaaaccc    660
ccagcagttc agtgctttcc ctgtcacaag taatgtaaac agagacagca gcatgggaaa    720
aatggggaag tcctgggatt tcggacatta ctatcagcct gcgcctctga tatccttccc    780
agactccaaa tttgtccaaa cgcaggggat cacaatggaa acagtggtct ttcctccgca    840
tcatcactac aacttcatcc cgagctactc gcatcccaga ctctaccagc agcaggcaaa    900
ctacgtccac aggccgccgc cgcagagcca ctttccctcc acacagagca tggtgcccga    960
ctccacagtg ccgcctgcag gccttgagag caagcgcatc cgcagagggc tggtcaagag   1020
gaaagccacg gtgcacagct gtgaatatcc aggctgccag aagacataca ccaagagctc   1080
tcatctcaaa gcacacctcc gtacacacac aggtgaaaag ccgtatcact gcacatggga   1140
tggctgcggg tggaagttcg cccgttcaga cgagctgacg agacacttcc gaaaacacac   1200
cggacagaag ccgtatgagt gtctgctgtg ccacagagcc ttcagcaggt ccgaccacct   1260
ggcgttacac atgaagagac acgtgtgagg aaaaacacta acaaaacaca acaaaccaca   1320
tgagcttcat ccatttcaaa ggcttgcgag gacctgtgtt cagctggaga gatgctggac   1380
gctgtttatg catgataaag aaagtataga agcactatta tatacacata caatcagtgt   1440
tgggggtaac gtgttacaag taatgcagat attacttttt gaagtaaaga gtaaagtgat   1500
gcagtacttt taaaaatgaa tgtaatgcaa gttacttttt agtttaatta acccagatag   1560
cacacataca cttgaagtca gaattattag tccccctgta tacttttctc ccaatttctt   1620
tttaacagag aaaaaattta tttctgaaca caatagcttt aataactcat ttctaataac   1680
tgatttattt tatttacttt gccatggtga taataaataa tattttacta gctatttttt   1740
caagacactt ctatacaact taaagtgaca tttaaaggct taactaggtt tattaggcaa   1800
ttcattgtat aacagtggtt tgttctgtag acaataaaaa aatgcttaag gaggctaata   1860
atattgacct taaaatgtct ttaaaaaatt ggaaactgct tttattttag cggaaataaa   1920
acaaataaga ctttctctag aagaaataaa tattataaga aatactgtga aaagttcctt   1980
gctctgttaa acatcatttg ggaaaaataa aaaaaaatgt aacaaataaa taaaataaaa   2040
taaattacag gagggcgaat acttttgact tcaactatac gtcgaggaaa agtcaatgaa   2100
agatcgtaac atctacagca tcgcattcga tcaaacattt gtattttaat gagccgtctt   2160
ctttacctct atacactgtc tatgaatctt caactcctga aattatgcga tggcaagctc   2220
tggtaaaaag acgcaacaac ttcatcttga atagctttaa aaaattcatt gttgaattaa   2280
aattgacatt ttgaaaagtg gattgtctca ctgggactga ctacttaatg cataggaaaa   2340
aagtacaaaa gtagcaaaca tgttgcttta aatttgcatt attctgtata tacagcatgt   2400
atagctcaaa agatcacttt attctaaaca acttttagat gtgtgtgtgt gttttttttaa   2460
```

```
agctaaacaa aagttataga gagtgttgtt agttgcaaag ctcgtcatat aaaaaaaaaa   2520

aaaaaaaaaa aa                                                       2532


<210> SEQ ID NO 10
<211> LENGTH: 1098
<212> TYPE: DNA
<213> ORGANISM: Danio rerio

<400> SEQUENCE: 10

atggctgtga ctcaagccgt actgccttca ttttcaaact tctgcaccaa ctccgaaaac     60

atgaagtttg aaaaaggctt tctggatctg gactccaagg atctgcacca aagcccagcc    120

agctacaaac cttcccagtt cctgactgat gagcaccagg acgacagcga gggatgctgg    180

gacatggagt tcctactgtc tgactgggcc agtatgtcac ctgaacggtc caactctcaa    240

aactacactc cccagcggcc gaccctacag gaccagcttc acagtccaga tctttatcag    300

gagctgaacg caccaaaacc aaacagacat caagtgtgcg ttgcaagttc cctagctgag    360

ctgcttcctc ctgaagcaac cttaagttcc tccctgcctc ctgacctcca gtttaattgt    420

ggatttctag atcaacaagc tgccaaatca tattcccagg cagaaaaccc ccagcagttc    480

agtgctttcc ctgtcacaag taatgtaaac agagacagca gcatgggaaa aatggggaag    540

tcctgggatt tcggacatta ctatcagcct gcgcctctga tatccttccc agactccaaa    600

tttgtccaaa cgcaggggat cacaatggaa acagtggtct ttcctccgca tcatcactac    660

aacttcatcc cgagctactc gcatcccaga ctctaccagc agcaggcaaa ctacgtccac    720

aggccgccgc cgcagagcca ctttccctcc acacagagca tggtgcccga ctccacagtg    780

ccgcctgcag gccttgagag caagcgcatc cgcagagggc tggtcaagag gaaagccacg    840

gtgcacagct gtgaatatcc aggctgccag aagacataca ccaagagctc tcatctcaaa    900

gcacacctcc gtacacacac aggtgaaaag ccgtatcact gcacatggga tggctgcggg    960

tggaagttcg cccgttcaga cgagctgacg agacacttcc gaaaacacac cggacagaag   1020

ccgtatgagt gtctgctgtg ccacagagcc ttcagcaggt ccgaccacct ggcgttacac   1080

atgaagagac acgtgtga                                                 1098


<210> SEQ ID NO 11
<211> LENGTH: 365
<212> TYPE: PRT
<213> ORGANISM: Danio rerio

<400> SEQUENCE: 11

Met Ala Val Thr Gln Ala Val Leu Pro Ser Phe Ser Asn Phe Cys Thr
1               5                   10                  15

Asn Ser Glu Asn Met Lys Phe Glu Lys Gly Phe Leu Asp Leu Asp Ser
            20                  25                  30

Lys Asp Leu His Gln Ser Pro Ala Ser Tyr Lys Pro Ser Gln Phe Leu
        35                  40                  45

Thr Asp Glu His Gln Asp Asp Ser Glu Gly Cys Trp Asp Met Glu Phe
    50                  55                  60

Leu Leu Ser Asp Trp Ala Ser Met Ser Pro Glu Arg Ser Asn Ser Gln
65                  70                  75                  80

Asn Tyr Thr Pro Gln Arg Pro Thr Leu Gln Asp Gln Leu His Ser Pro
                85                  90                  95

Asp Leu Tyr Gln Glu Leu Asn Ala Pro Lys Pro Asn Arg His Gln Val
            100                 105                 110
```

```
Cys Val Ala Ser Ser Leu Ala Glu Leu Leu Pro Pro Glu Ala Thr Leu
        115                 120                 125

Ser Ser Ser Leu Pro Pro Asp Leu Gln Phe Asn Cys Gly Phe Leu Asp
    130                 135                 140

Gln Gln Ala Ala Lys Ser Tyr Ser Gln Ala Glu Asn Pro Gln Gln Phe
145                 150                 155                 160

Ser Ala Phe Pro Val Thr Ser Asn Val Asn Arg Asp Ser Ser Met Gly
                165                 170                 175

Lys Met Gly Lys Ser Trp Asp Phe Gly His Tyr Tyr Gln Pro Ala Pro
            180                 185                 190

Leu Ile Ser Phe Pro Asp Ser Lys Phe Val Gln Thr Gln Gly Ile Thr
        195                 200                 205

Met Glu Thr Val Val Phe Pro Pro His His His Tyr Asn Phe Ile Pro
    210                 215                 220

Ser Tyr Ser His Pro Arg Leu Tyr Gln Gln Gln Ala Asn Tyr Val His
225                 230                 235                 240

Arg Pro Pro Pro Gln Ser His Phe Pro Ser Thr Gln Ser Met Val Pro
                245                 250                 255

Asp Ser Thr Val Pro Pro Ala Gly Leu Glu Ser Lys Arg Ile Arg Arg
            260                 265                 270

Gly Leu Val Lys Arg Lys Ala Thr Val His Ser Cys Glu Tyr Pro Gly
        275                 280                 285

Cys Gln Lys Thr Tyr Thr Lys Ser Ser His Leu Lys Ala His Leu Arg
    290                 295                 300

Thr His Thr Gly Glu Lys Pro Tyr His Cys Thr Trp Asp Gly Cys Gly
305                 310                 315                 320

Trp Lys Phe Ala Arg Ser Asp Glu Leu Thr Arg His Phe Arg Lys His
                325                 330                 335

Thr Gly Gln Lys Pro Tyr Glu Cys Leu Leu Cys His Arg Ala Phe Ser
            340                 345                 350

Arg Ser Asp His Leu Ala Leu His Met Lys Arg His Val
        355                 360                 365


<210> SEQ ID NO 12
<211> LENGTH: 358
<212> TYPE: PRT
<213> ORGANISM: Mus musculus

<400> SEQUENCE: 12

Met Ala Ser Ala Glu Thr Val Leu Pro Ser Ile Ser Thr Leu Thr Thr
1               5                   10                  15

Leu Gly Gln Phe Leu Asp Thr Gln Glu Asp Phe Leu Lys Trp Trp Arg
            20                  25                  30

Ser Glu Glu Thr Gln Asp Leu Gly Pro Gly Pro Pro Asn Pro Thr Gly
        35                  40                  45

Pro Ser His His Val Ser Leu Lys Ser Glu Asp Pro Ser Gly Glu Asp
    50                  55                  60

Asp Glu Arg Asp Val Thr Cys Ala Trp Asp Pro Asp Leu Phe Leu Thr
65                  70                  75                  80

Asn Phe Pro Gly Ser Glu Ser Pro Gly Thr Ser Arg Thr Cys Ala Leu
                85                  90                  95

Ala Pro Ser Val Gly Pro Val Ala Gln Phe Glu Pro Pro Glu Ser Leu
            100                 105                 110

Gly Ala Tyr Ala Gly Gly Pro Gly Leu Val Thr Gly Pro Leu Gly Ser
        115                 120                 125
```

-continued

```
Glu Glu His Thr Ser Trp Ala His Pro Thr Pro Arg Pro Pro Ala Pro
    130                 135                 140

Glu Pro Phe Val Ala Pro Ala Leu Ala Pro Gly Leu Ala Pro Lys Ala
145                 150                 155                 160

Gln Pro Ser Tyr Ser Asp Ser Arg Ala Gly Ser Val Gly Gly Phe Phe
                165                 170                 175

Pro Arg Ala Gly Leu Ala Val Pro Ala Ala Pro Gly Ala Pro Tyr Gly
            180                 185                 190

Leu Leu Ser Gly Tyr Pro Ala Leu Tyr Pro Ala Pro Gln Tyr Gln Gly
        195                 200                 205

His Phe Gln Leu Phe Arg Gly Leu Ala Ala Pro Ser Ala Gly Pro Thr
    210                 215                 220

Ala Pro Pro Ser Phe Leu Asn Cys Leu Gly Pro Gly Thr Val Ala Thr
225                 230                 235                 240

Glu Leu Gly Ala Thr Ala Ile Ala Gly Asp Ala Gly Leu Ser Pro Gly
                245                 250                 255

Thr Ala Pro Pro Lys Arg Ser Arg Arg Thr Leu Ala Pro Lys Arg Gln
            260                 265                 270

Ala Ala His Thr Cys Gly His Glu Gly Cys Gly Lys Ser Tyr Thr Lys
        275                 280                 285

Ser Ser His Leu Lys Ala His Leu Arg Thr His Thr Gly Glu Lys Pro
    290                 295                 300

Tyr Ala Cys Ser Trp Asp Gly Cys Asp Trp Arg Phe Ala Arg Ser Asp
305                 310                 315                 320

Glu Leu Thr Arg His Tyr Arg Lys His Thr Gly His Arg Pro Phe Cys
                325                 330                 335

Cys Gly Leu Cys Pro Arg Ala Phe Ser Arg Ser Asp His Leu Ala Leu
            340                 345                 350

His Met Lys Arg His Leu
        355
```

KLF INDUCED CARDIOMYOGENESIS

CROSS-REFERENCE TO RELATED APPLICATIONS

This application is a U.S. national phase application, pursuant to 35 U.S.C. 371, of PCT International Application No. PCT/AU2020/050775, filed Jul. 30, 2020. This international application claims priority to Australian Patent Application No. 2019902703, filed Jul. 30, 2019. The contents of the aforementioned patent applications are incorporated herein by reference in their entireties.

TECHNICAL FIELD

The technology relates to methods for promoting cardiomyogenesis (that is, the formation of new cardiomyocytes as a result of cell division) by administering at least one of KLF1 or KLF2b or at least one of a KLF1 or KLF2b nucleic acid to a cardiomyocyte. The technology further relates to promoting cardiomyogenesis in a subject by administering at least one of KLF1 or KLF2b protein or nucleic acid to the subject.

SEQUENCE LISTING

The instant application contains a Sequence Listing which has been submitted in ASCII format via EFS-Web and is hereby incorporated by reference in its entirety. The ASCII copy, created on Aug. 18, 2025, is 32,768 bytes in size and is named "057734-5058_Sequence_Listing_ST25".

BACKGROUND

Cardiomyocytes in the adult mammalian heart are terminally differentiated cells that have exited from the cell cycle and have limited proliferative capacity. Consequently, death of mature cardiomyocytes in pathological cardiac conditions leads to high mortality and morbidity. For example, the high mortality and morbidity associated with myocardial infarction is due in large part to the fact that the human heart has an extremely limited ability for repair through regeneration of new cardiomyocytes (cardiomyogenesis). As a result, the infarcted heart muscle is replaced by fibrotic scar tissue, which cannot contact, resulting in reduced heart pump activity, heart failure and/or sudden death from an arrhythmia.

In contrast to mammals, certain vertebrates, including the teleost zebrafish, show full, scarless regeneration of the heart after myocardial infarction. It is known from fate mapping studies that cardiomyocytes, not stem cells, are the major source for new cardiac muscle in regenerating zebrafish hearts. Importantly, a similar regenerative capacity has been discovered in neonatal mice. However, the self-renewal capacity of mammalian cardiomyocytes quickly diminishes after birth.

Cardiovascular disorders can induce severe, progressive loss of contractile heart muscle tissue, as a result of loss of billions of cardiomyocytes (CMs). Because of the low regenerative capacity of the mammalian heart, this can ultimately lead to heart failure with no treatment options currently available to robustly restore the lost CMs.

KLF1, a member of Krüppel-like transcription factors, is known to have an important role in red blood cell development and mutations in the KLF1 gene cause congenital anaemia. The present inventors have discovered a previously unknown role for KLF1 in cardiomyogenesis. Further, the present inventors have demonstrated that overexpressing KLF1 in adult cardiomyocytes can induce cardiomyogenesis in adult mammalian hearts and lead to cardiac regeneration.

SUMMARY

In a first aspect, there is provided a method for inducing cardiomyogenesis comprising administering a therapeutically effective amount of a KLF to a cardiomyocyte, or inducing expression of the KLF in the cardiomyocyte, for example to increase the level of KLF1 and/or KLF2b in the cardiomyocytes thereby inducing cardiomyogenesis.

In one embodiment the population of cardiomyocytes are infant, child or adult cardiomyocytes. The population of cardiomyocytes may be isolated from a subject or present in a subject.

In one embodiment the cardiomyogenesis facilitates cardiac regeneration in the subject. The cardiac regeneration may characterized by an increase in ejection fraction, fractional shortening or both.

The cardiac regeneration may be characterized by an increase in vascular endothelial cells, epicardial cells or both.

The KLF may induce dedifferentiation of the cardiomyocyte to produce proliferative cardiomyocytes, preferably the proliferative cardiomyocytes are mitotic.

The method may further comprise allowing the proliferative cardiomyocytes to proliferate in the presence of the KLF to produce a population of proliferative cardiomyocytes.

The proliferative cardiomyocytes preferentially metabolize glucose using the pentose phosphate pathway, the serine synthesis pathway, or both.

The method may further comprise allowing differentiation of the population of proliferative cardiomyocytes to produce a population of cardiomyocytes. The differentiation may occur in the substantial absence of the KLF, or after the induction of KLF has ceased.

In some embodiments the KLF induces chromatin remodeling to facilitate the dedifferentiation.

The KLF induced chromatin remodeling may reduce accessibility to binding sites of one, or any combination of, MEF2C, GATA4, MEF2A, and NKX2.5.

The KLF can be KLF1, KLF2b or both, a KLF1 and/or a KLF2b nucleic acid or a vector comprising at least one of the nucleic acids. The vector may comprise the nucleic acid operably coupled to a promoter. The promoter may be a cardiac specific promoter. In embodiments where the population of cardiomyocytes is present in a subject, and the KLF is administered to the subject. For example, the KLF may be administered to the heart of the subject.

The KLF1 protein may be SEQ ID NO: 1, 11, or a protein at least 80% identical to SEQ ID NO: 1 or 11. The KLF1 nucleic acid may comprise or consists of any one of SEQ ID NO: 2, 3, 4, 5, 9, 10 or a nucleic acid at least 80% identical to any one of SEQ ID NO: 2, 3, 4, 5, 9 or 10.

The KLF2b protein may be SEQ ID NO: 6, or a protein at least 80% identical to SEQ ID NO: 6. The KLF2b nucleic acid may comprises or consists of SEQ ID NO:7 or 8, or a nucleic acid at least 80% identical to any one of SEQ ID NO: 7 or 8.

The promoter may be the alpha-myosin heavy chain (α-MHC) promoter, the myosin light chain 2 (MLC-2) promoter, the cardiac troponin C (cTnC) promoter, the NCX1 promoter, or the TNNT2 promoter. The promoter may be used to provide CM expression of a vector encoding KLF1 or KLF2b.

The promoter may be an inducible promoter, for example a tetracycline inducible promoter, steroid hormone (e.g. progesterone or ecdysone) inducible promoter, a hypoxia inducible promoter, a promoter that is specific for an area near the site of cardiac damage, or a promoter that is responsive to stress that results from ischemia and reperfusion.

The proliferative cardiomyocytes may be cardiomyocyte progenitor cells, immature cardiomyocytes, cardiomyocytes with embryonic phenotype, or any combination thereof.

In some embodiments the cardiomyogenesis does not involve reprogramming the cell lineage of the cardiomyocytes.

In some embodiments the proliferative cardiomyocytes re-enter the cell cycle.

In some embodiments the proliferative cardiomyocytes are characterized by an increased reliance on the pentose phosphate pathway (PPP), the serine synthesis pathway, or both, compared to the cardiomyocytes.

In an embodiment the cardiomyogenesis includes expansion of epicardial cells and endothelial cells.

In an embodiment the cardiomyogenesis is characterized by increased numbers of epicardial cells, vascular endothelial cells or both.

The subject may have a cardiac condition characterized by cardiomyocyte loss, such as a myocardial infarction, ischemic cardiomyopathy, dilated cardiomyopathy or heart failure.

In a second aspect there is provided a population of cardiomyocytes or proliferative cardiomyocytes produced by a method of the first aspect.

In a third aspect there is provided a composition comprising cardiomyocytes or proliferative cardiomyocytes produced by a method of the first aspect.

In a fourth aspect there is provided a method of treating a cardiac condition in a subject comprising administering to the subject the population of cardiomyocytes or proliferative cardiomyocytes of the second aspect, or the composition of the third aspect.

In a fifth aspect there is provided use of the population of cardiomyocytes or proliferative cardiomyocytes of the second aspect, or the composition of the third aspect in the manufacture of a medicament for the treatment of a cardiac condition.

Definitions

As used herein, unless the context clearly requires otherwise, the term 'KLF' refers to either or both of KLF1 and KLF2b.

Throughout this specification, unless the context clearly requires otherwise, the word 'comprise', or variations such as 'comprises' or 'comprising', will be understood to imply the inclusion of a stated element, integer or step, or group of elements, integers or steps, but not the exclusion of any other element, integer or step, or group of elements, integers or steps.

Throughout this specification, the term 'consisting of' means consisting only of.

Any discussion of documents, acts, materials, devices, articles or the like which has been included in the present specification is solely for the purpose of providing a context for the present technology. It is not to be taken as an admission that any or all of these matters form part of the prior art base or were common general knowledge in the field relevant to the present technology as it existed before the priority date of each claim of this specification.

Unless the context requires otherwise, or specifically stated to the contrary, integers, steps, or elements of the technology recited herein as singular integers, steps or elements clearly encompass both singular and plural forms of the recited integers, steps or elements.

In the context of the present specification the terms 'a' and 'an' are used to refer to one or more than one (i.e., at least one) of the grammatical object of the article. By way of example, reference to 'an element' means one element, or more than one element.

In the context of the present specification the term 'about' means that reference to a figure or value is not to be taken as an absolute figure or value, but includes margins of variation above or below the figure or value in line with what a skilled person would understand according to the art, including within typical margins of error or instrument limitation. In other words, use of the term 'about' is understood to refer to a range or approximation that a person skilled in the art would consider to be equivalent to a recited value in the context of achieving the same function or result.

As used herein, the terms 'treatment', 'treating' and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. 'Treatment', as used herein, covers any treatment of a disease in a mammal, particularly in a human, and includes: (a) preventing the disease from occurring in a subject who may be predisposed to the disease but has not yet been diagnosed as having it; (b) inhibiting the disease, i.e., arresting its development; and (c) relieving the disease, i.e., causing regression of the disease.

The terms 'individual', 'subject', and 'patient', are used interchangeably herein, refer to an animal, including, but not limited to, fish (e.g. zebrafish), rodents (rats, mice), non-human primates, humans, canines, felines, and ungulates (e.g., equines, bovines, ovines, porcines, caprines). In some embodiments the subject is a human.

A 'therapeutically effective amount' or 'efficacious amount' means the amount of a compound that, when administered to a mammal or other subject, is sufficient to effect such treatment for the disease. The 'therapeutically effective amount' will vary depending on the compound or the cell, the disease and its severity and the age, weight, etc., of the subject to be treated.

Those skilled in the art will appreciate that the technology described herein is susceptible to variations and modifications other than those specifically described. It is to be understood that the technology includes all such variations and modifications. For the avoidance of doubt, the technology also includes all of the steps, features, and compounds referred to or indicated in this specification, individually or collectively, and any and all combinations of any two or more of said steps, features and compounds.

Arrowheads, klf1 mRNAs in myocardium. Arrow, klf1 mRNA in a blood cell progenitor-like cell. ***p<0.005.

Figure 2:
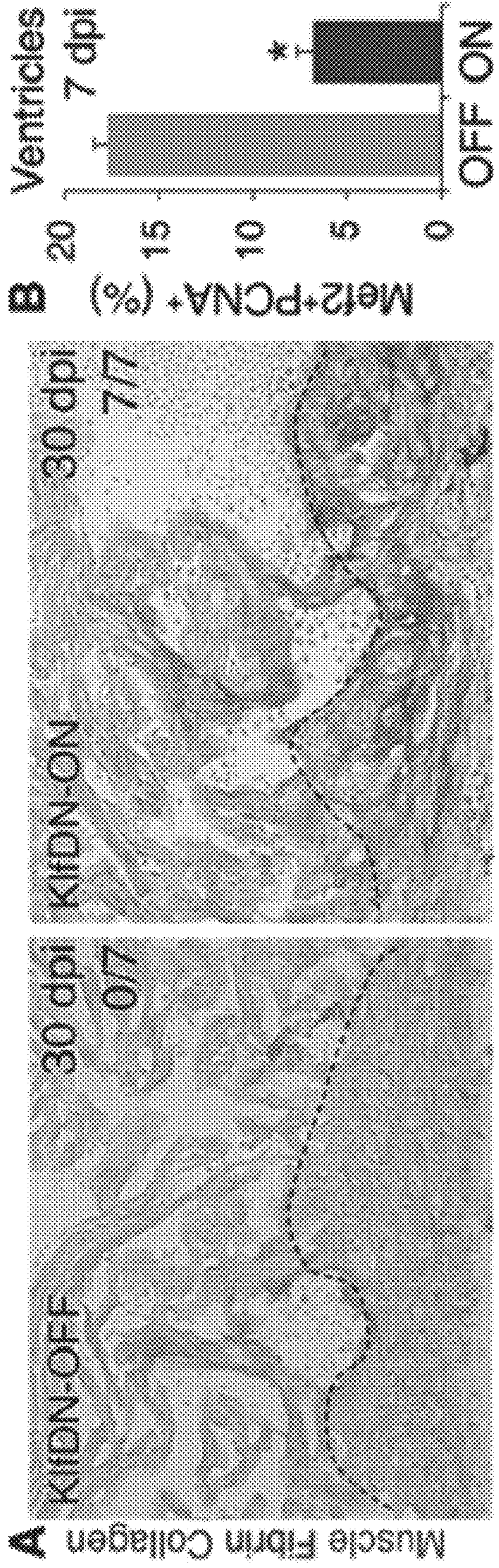

FIG. 2: Klf1 function in zebrafish heart regeneration. (A) Picro-Mallory staining of ventricles from control (KlfDN-OFF) or transgenic zebrafish expressing a dominant-negative Klf1 (KlfDN-ON). Dotted line, resection plane. dpi, days post-injury. Details of the transgenic line expressing KlfDN are described in FIG. 11A. (B) Quantification of proliferating CMs detected by immunofluorescence of the myocyte nuclear marker, myocyte enhancer factor 2 (Mef2), and proliferating cell nuclear antigen (PCNA). *P<0.05.

Figure 3:
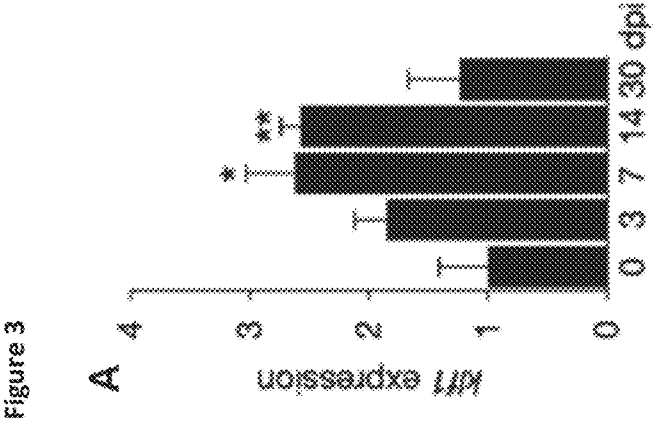
Figure 3:
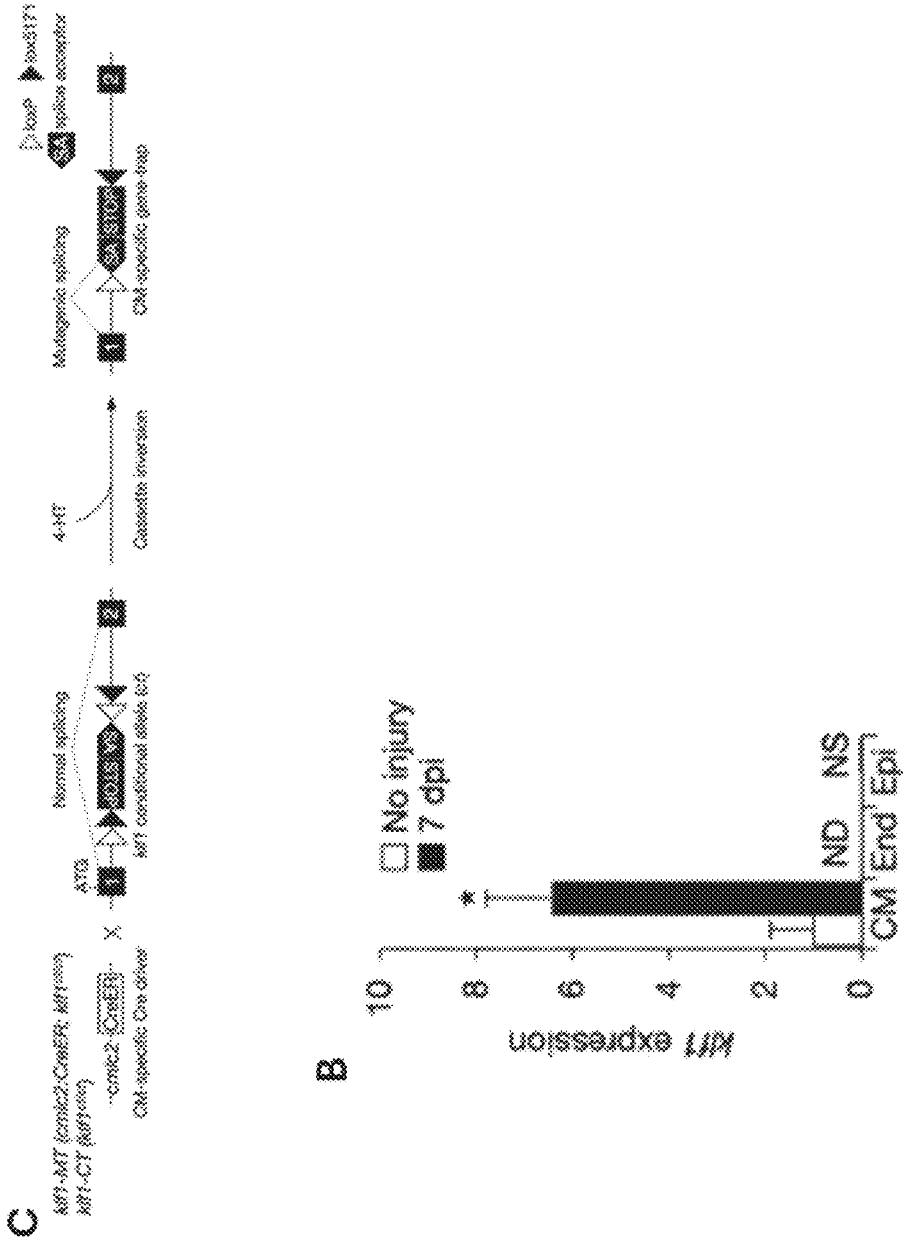
Figure 3:
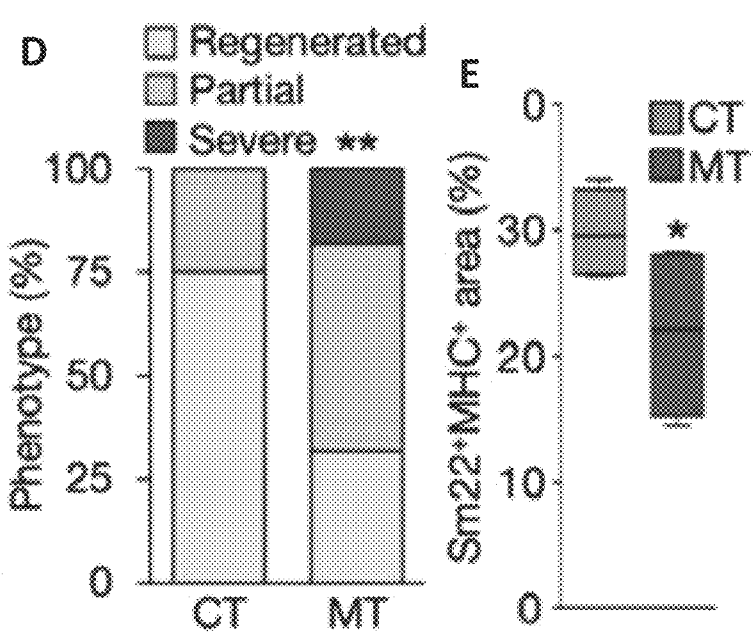
Figure 3:
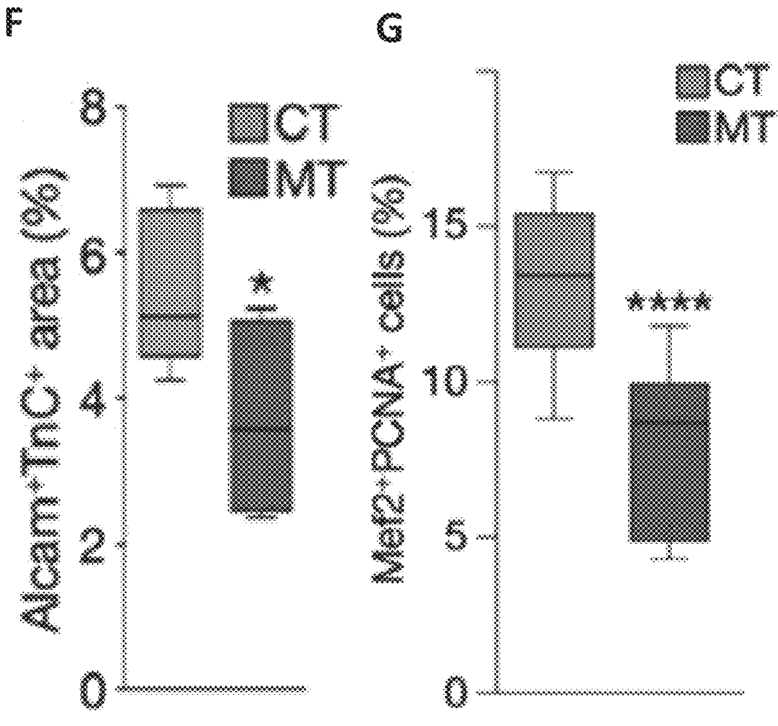

FIG. 3: Expression and functional analysis of klf1 in regenerating zebrafish hearts. (A) Quantitative reverse-transcription PCR (RT-qPCR) analysis of klf1 in injured ventricles (mean±SEM, n=5-6). Gene expression is shown relative to the level in uninjured controls, which are indicated as 0 dpi (days post-injury). (B) RT-qPCR analysis of klf1 in purified cardiac cells (mean±SEM). Cardiomyocytes (CM), endocardial cells (End), and epicardial cells (Epi) were purified using fluorescence-activated cell sorting (FACS) from uninjured and 7 dpi ventricles of Tg(cmlc2:EGFP), Tg(fli1a:EGFP), and TgBAC(tcf21:DsRed2) fish, respectively. Gene expression is shown relative to the level in uninjured cardiomyocytes. In situ hybridization of klf1 mRNA using RNAscope and immunofluorescence against TnC in regenerating hearts (not shown) indicated that klf1 mRNA was detected in hematopoietic cells and cardiac muscle. (C) Cre-dependent conversion from the non-mutagenic orientation to the mutagenic orientation of $klf1^{ct}$. See FIG. 9 for the details of construction and characterization of $klf1^{ct}$. (D) Picro-Mallory staining of ventricular sections from control (klf1-CT) and klf1-depleted hearts (klf1-MT) was performed and regeneration quantification (n=20-22). (E, F) Immunofluorescence of myosin heavy chain (MHC) or cardiac troponin C (TnC) together with either smooth muscle protein 22α (Sm22) or Alcam, and box plots prepared to show quantification of $Sm22^+MHC^+$ (E) or $Alcam^+ TnC^+$ areas (F) (n=5-6). (G) Immunofluorescence of the myocyte nuclear marker, myocyte enhancer factor 2 (Mef2), and proliferating cell nuclear antigen (PCNA). Box plots were prepared to show quantification of $Mef2^+PCNA^+$ cells (n=7-9). *p<0.05, p<0.01, **p<0.001 by unpaired t-test (E, F, G).

Figure 4:
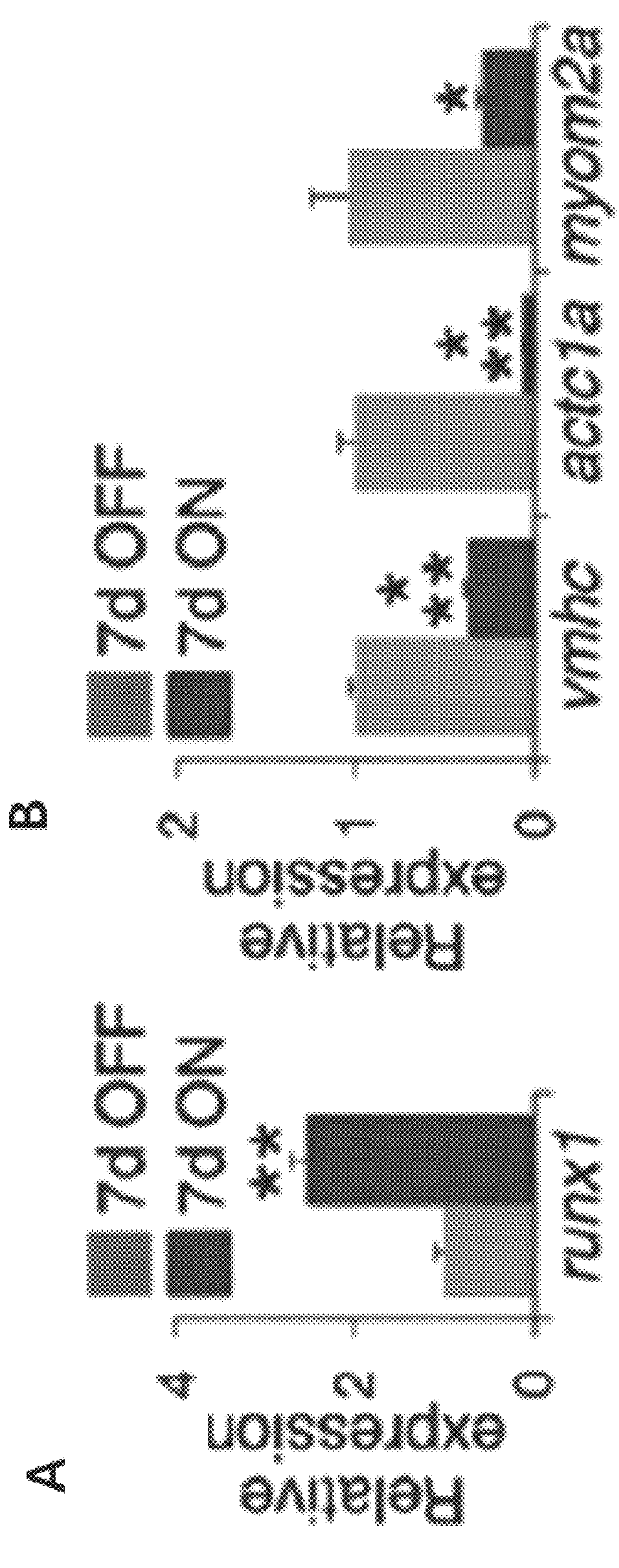

FIG. 4: Zebrafish Klf1-induced CM dedifferentiation. Induced expression of a dedifferentiation marker (runx1; A) and suppression of differentiated muscle markers (vmhc, actc1a, myom2a; B) with Klf1 overexpression. qPCR analysis of Klf1-ON and OFF ventricles at 7 days post Klf1 overexpression (ON). Details of the transgenic line used for Klf1 overexpression are described in FIG. 12A. *P<0.05; P<0.01; *P<0.005.

Figure 5:
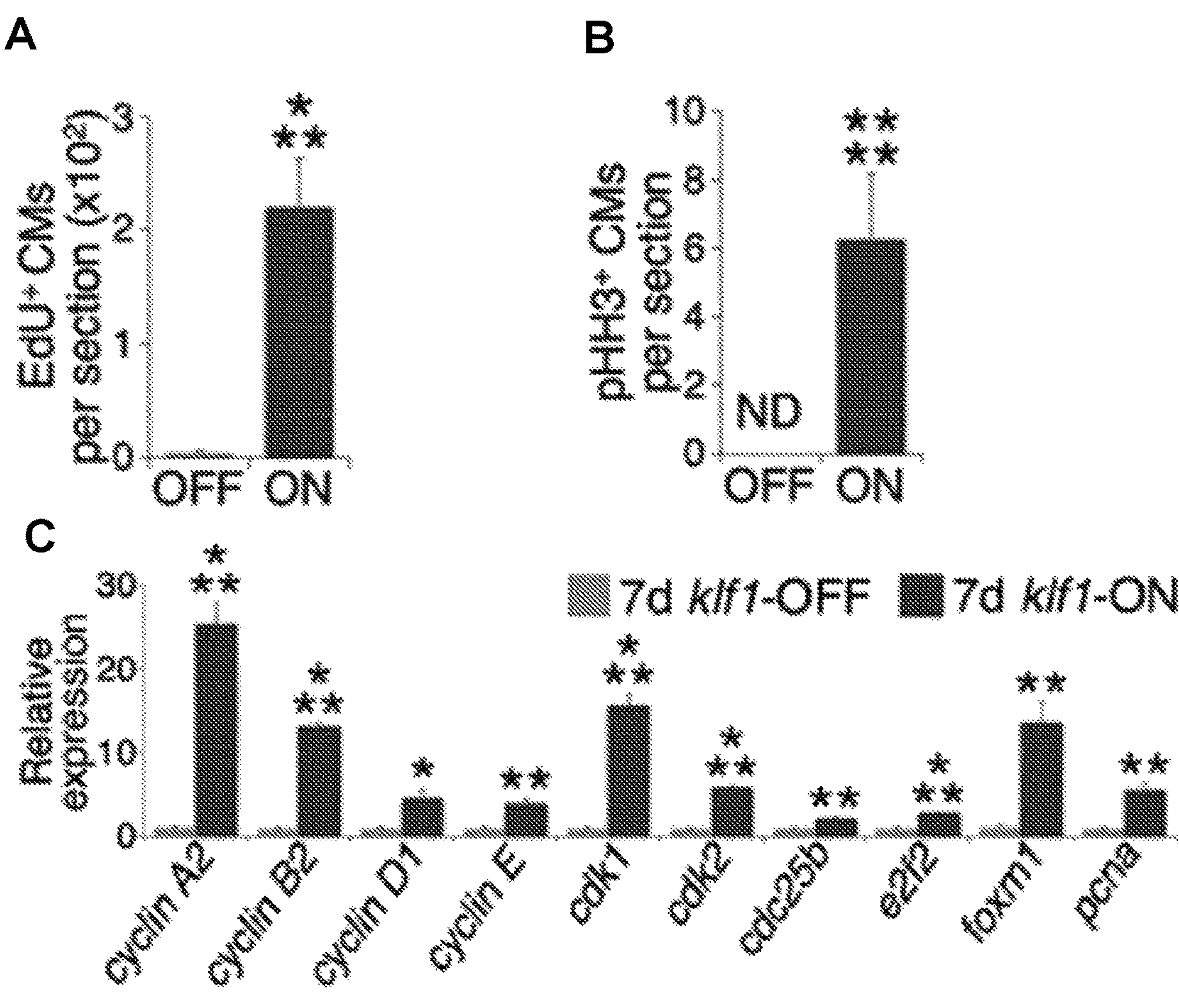

FIG. 5: Zebrafish Klf1 function in CM proliferation. (A) EdU was injected once daily from 9 to 11 days post-ON and S-phase CMs were quantified as $EdU^+$CMs at 12 days post-ON. (B) Mitotic CMs were quantified as phospho-histone H3 $(pHH3)^+$CMs at 12 days post-ON. (C) qPCR analysis of cell proliferation markers. Details of the transgenic line used for Klf1 overexpression are described in FIG. 12A. *P<0.05; P<0.01; *P<0.005; ****P<0.001. ND, not detectable.

Figure 6:
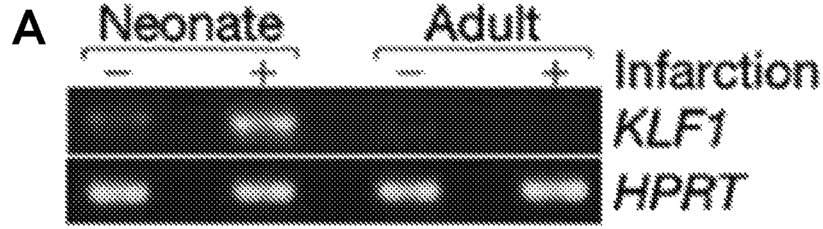
Figure 6:
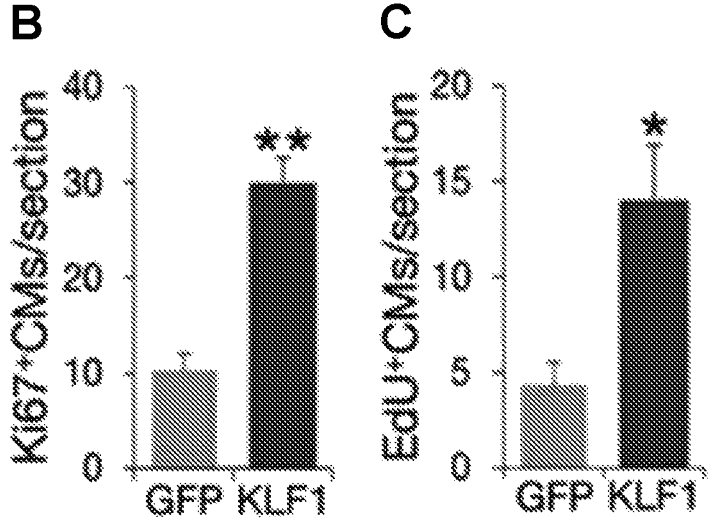

FIG. 6: Mouse Klf1 function. (A) Semi-qPCR analysis. Neonatal mouse hearts were injured at postnatal day 3 and collected at day 6. (B) CM proliferation was assessed by co-labeling of cardiac troponin T (TnT) with Ki67 and quantified in uninjured adult mouse hearts injected with control (GFP) or KLF1 adenovirus (KLF1). Colabeling was confirmed in the xz and yz planes. (C) Analysis of S-phase CM. $EdU^+$ nuclei were encompassed with WGA were quantified. *P<0.05; **P<0.01. dpt, days post-transfection; LV, left ventricle.

Figure 7:
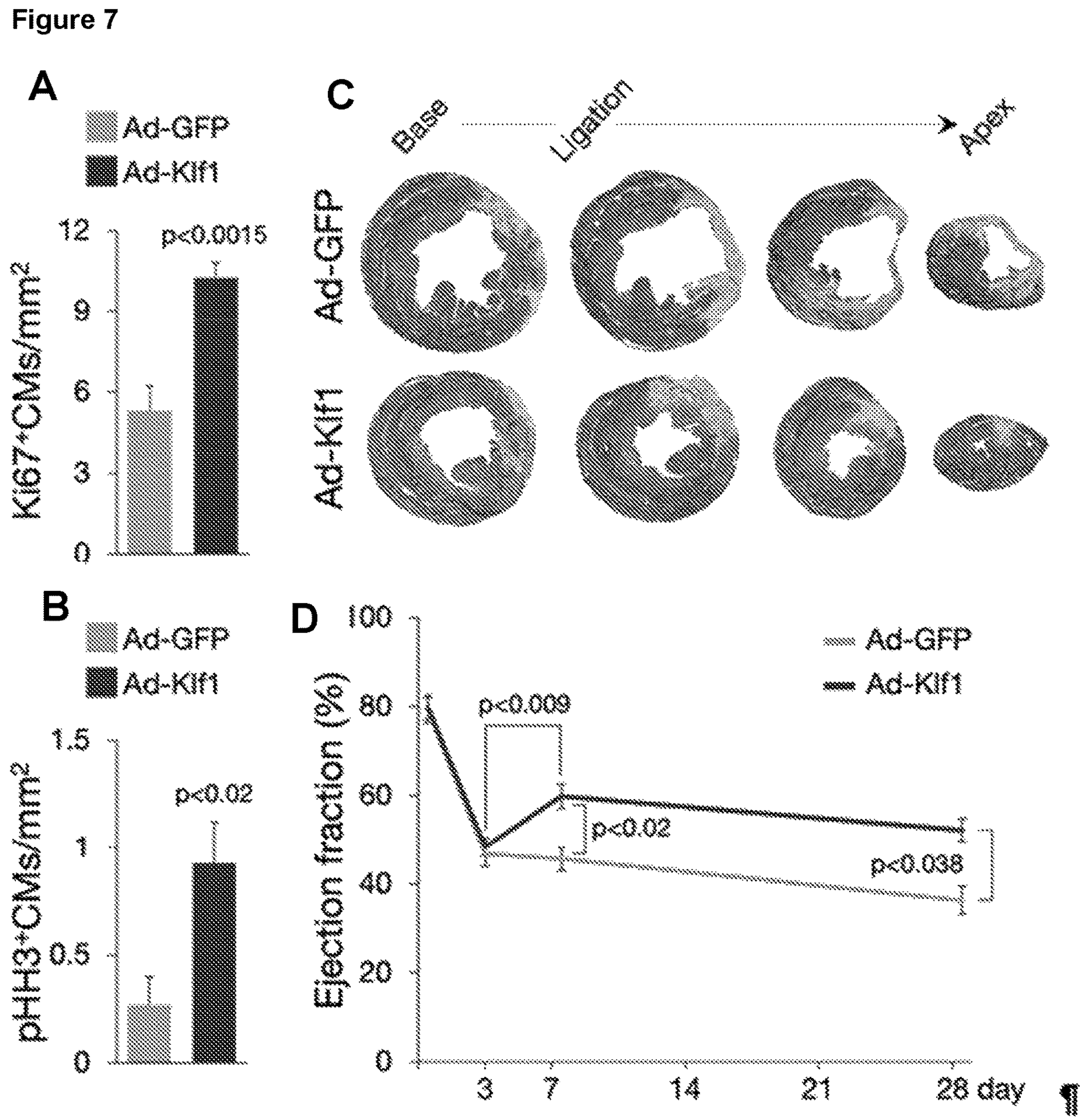

FIG. 7: Mouse Klf1 function in myocardial repair. (A) CM proliferation was assessed by co-labeling of TnT with Ki67 and quantified at 14 days post-myocardial infarction (MI). (B) CM mitosis was assessed by co-labeling of TnT with pHH3 and quantified at 14 days post-MI. (C) Analysis of hearts treated with control (Ad-GFP) or KLF1 adnovirus (Ad-Klf1) by Gomori-trichrome staining at 28 days post-MI. (D) Echo analysis of hearts treated with Ad-GFP or Ad-Klf1.

Figure 8:
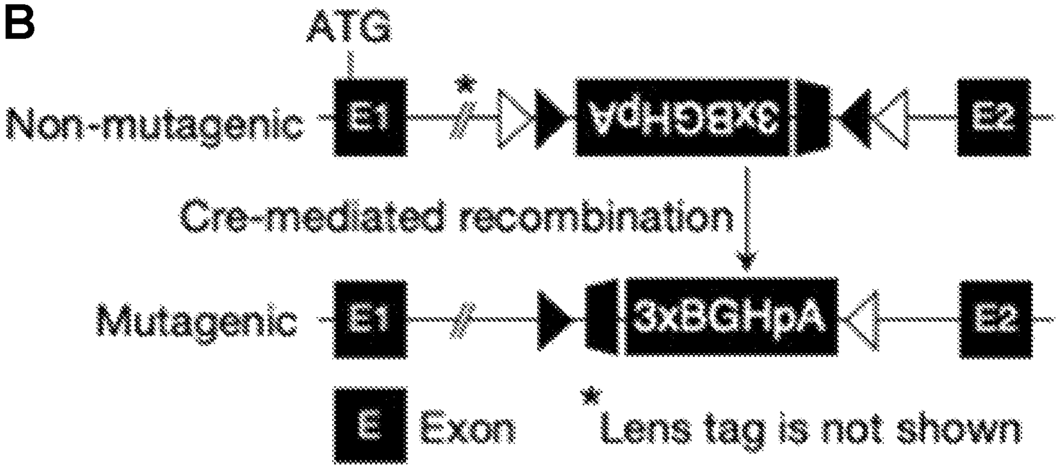
Figure 8:
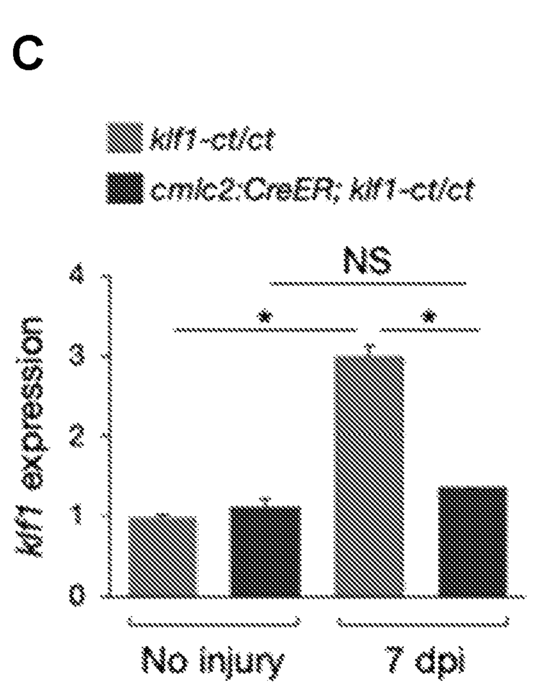
Figure 8:
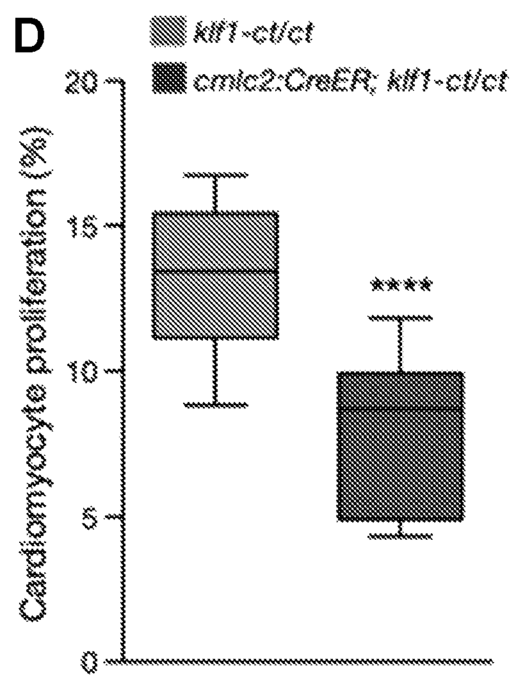
Figure 8:
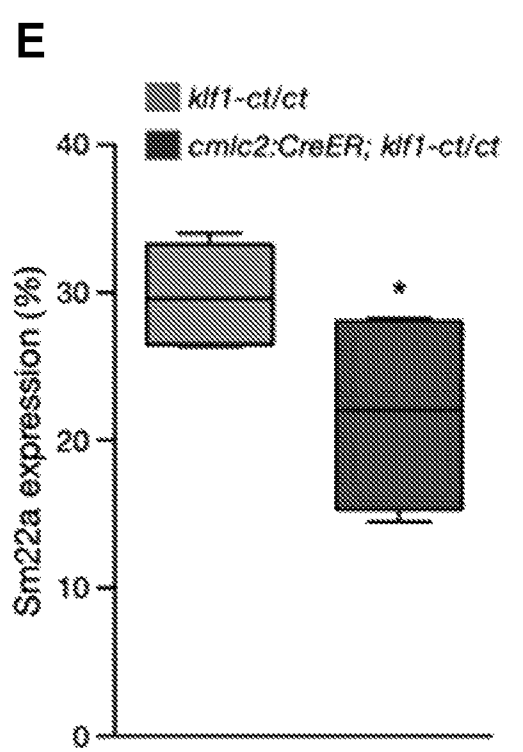
Figure 8:
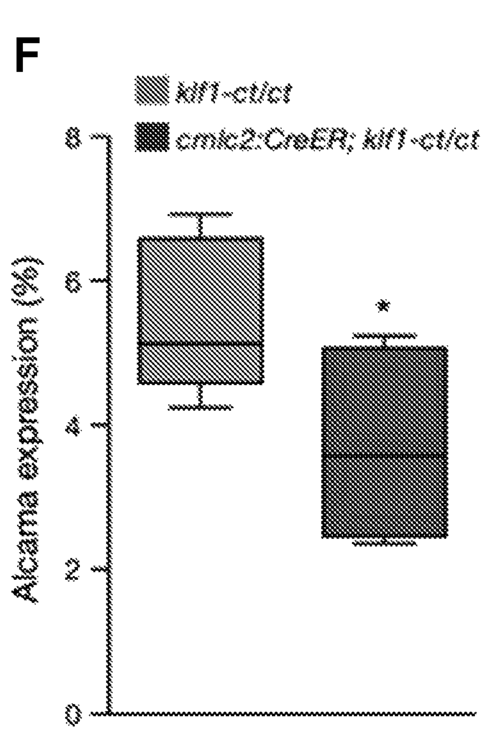

FIG. 8: (A) Zwitch2 gene trap cassette. (B) Schematic of Cre-mediated inactivation of klf1 gene. (C) Cardiac muscle specific inactivation of klf1 gene expression. (D) Attenuation of CM proliferation by cardiac muscle specific inactivation of klf1 gene expression. (E, F) Reduction of CM dedifferentiation makers by cardiac muscle specific inactivation of klf1 gene expression.

Figure 9:
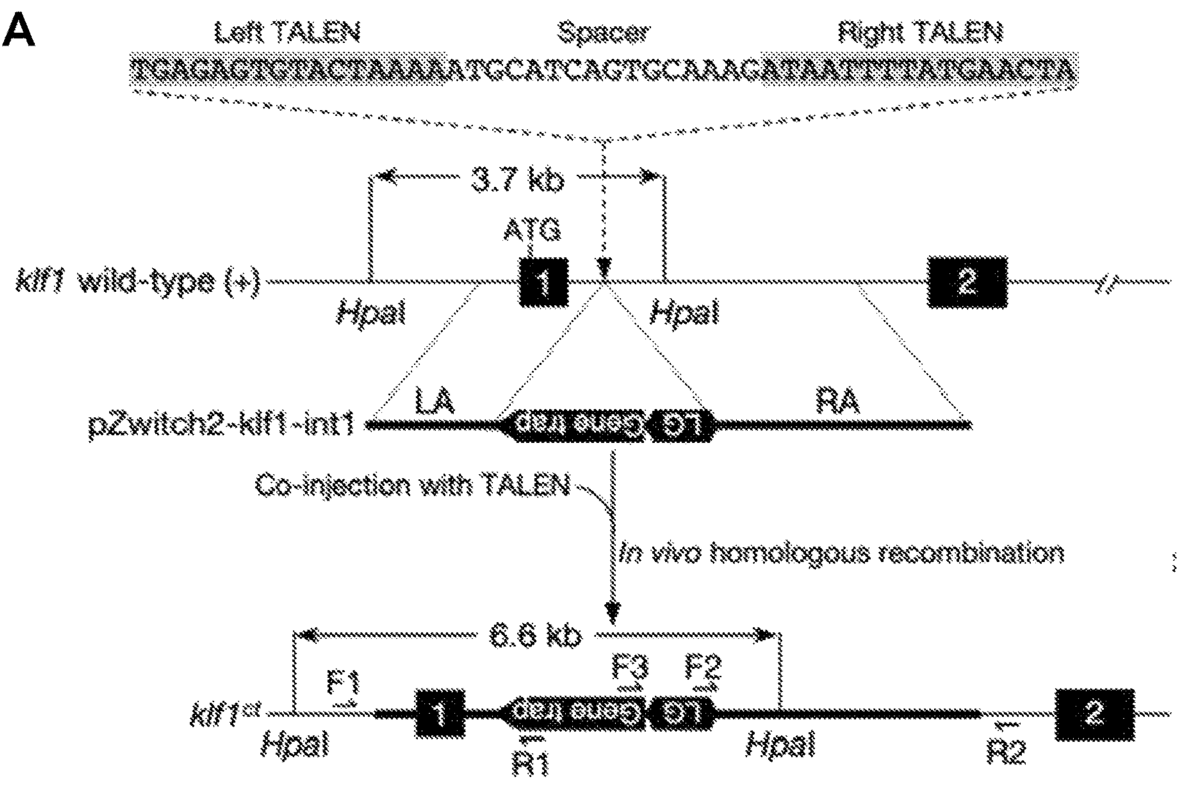
Figure 9:
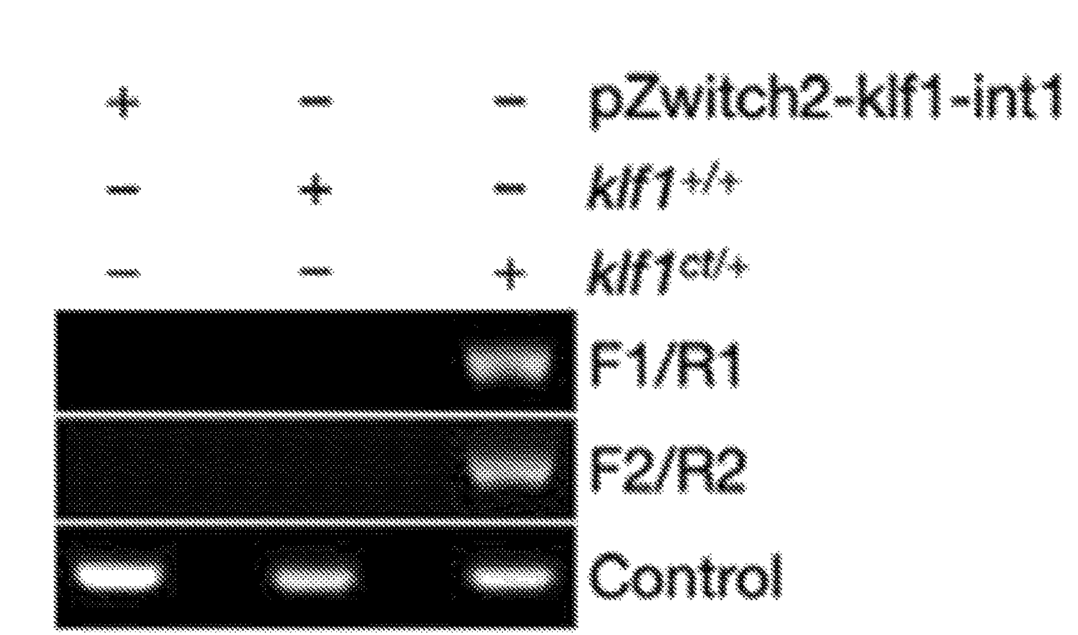
Figure 9:
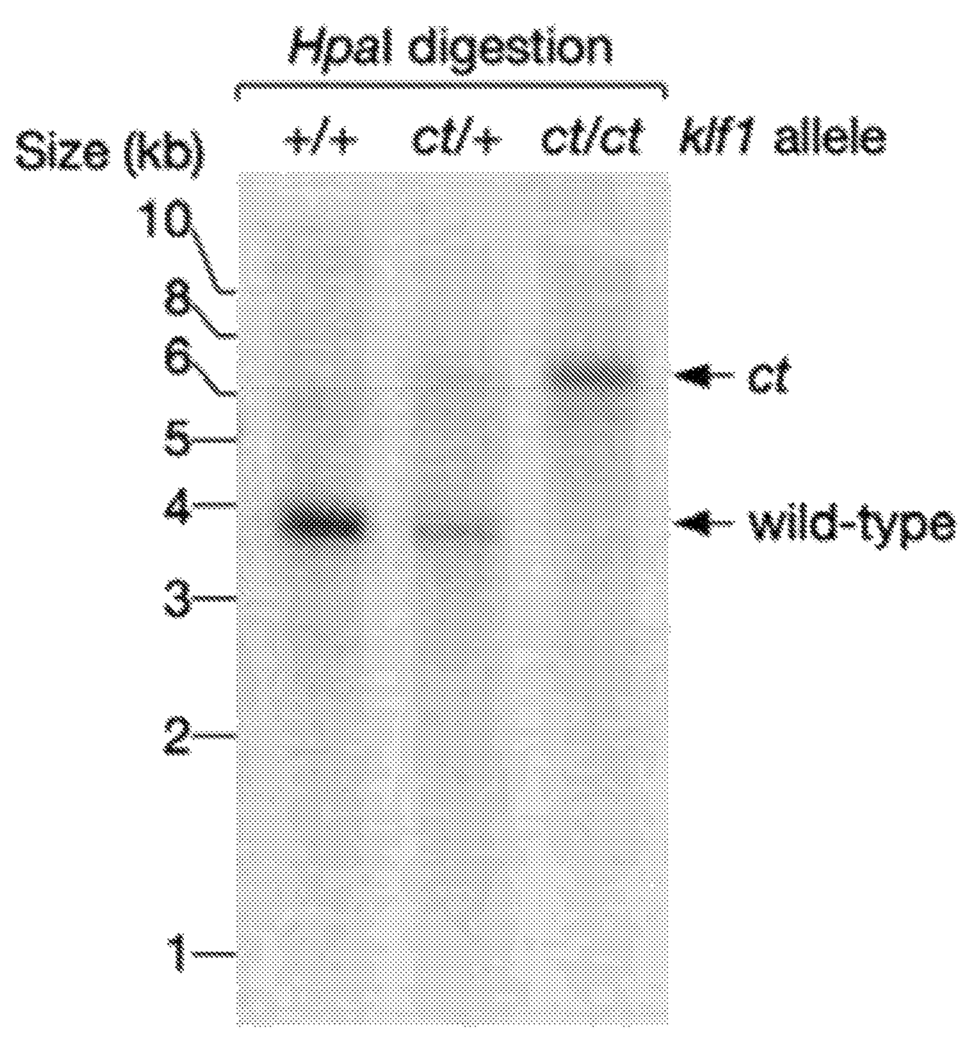
Figure 9:
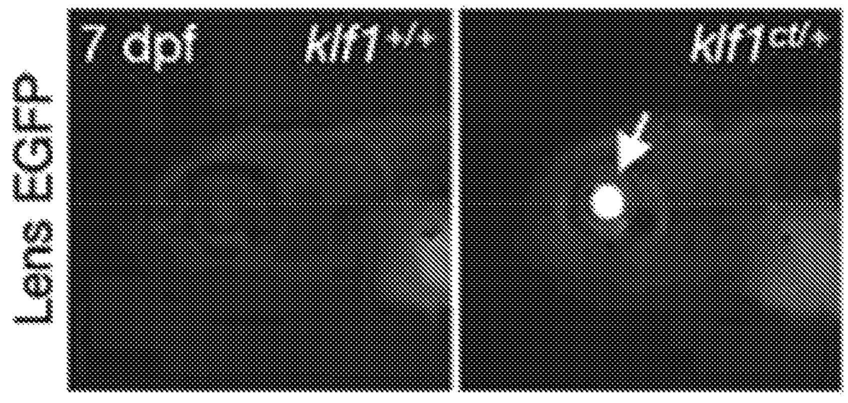
Figure 9:
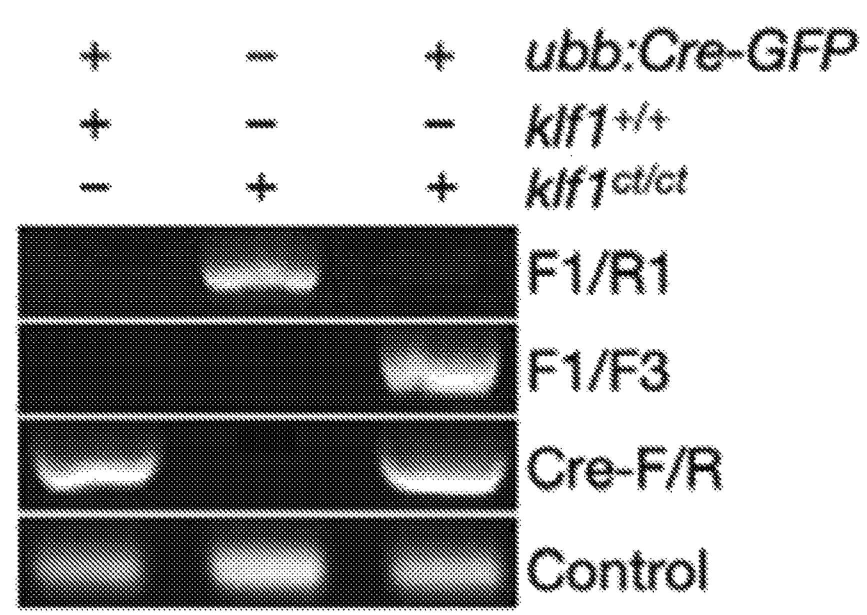
Figure 9:
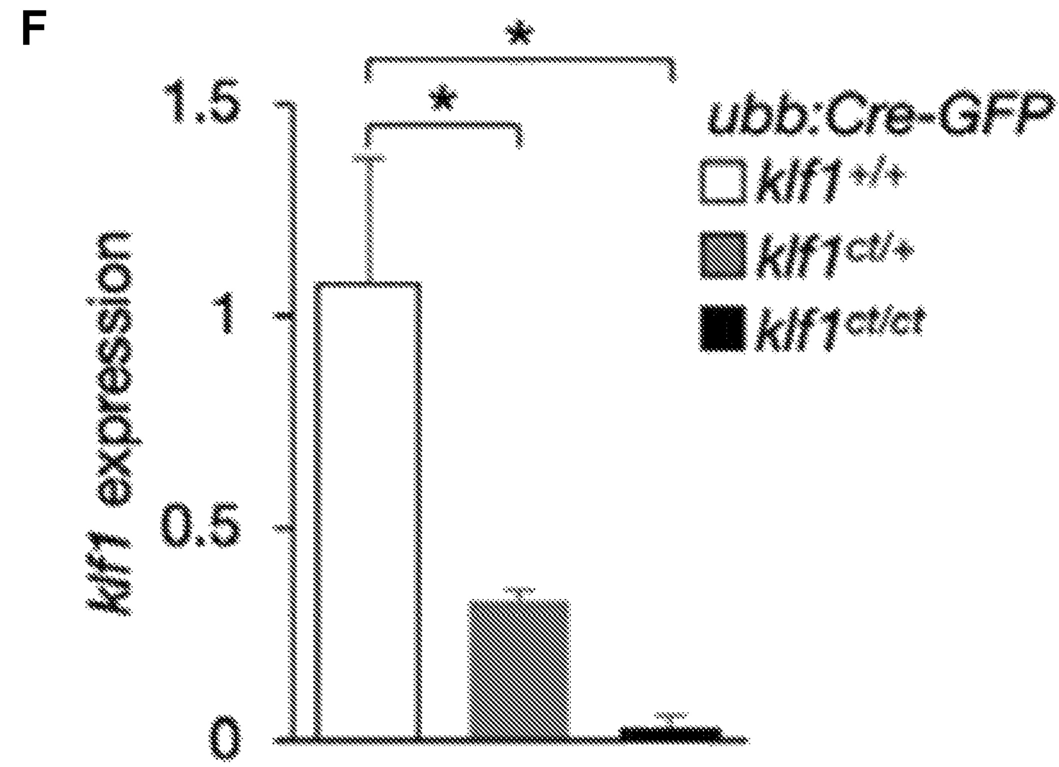
Figure 9:
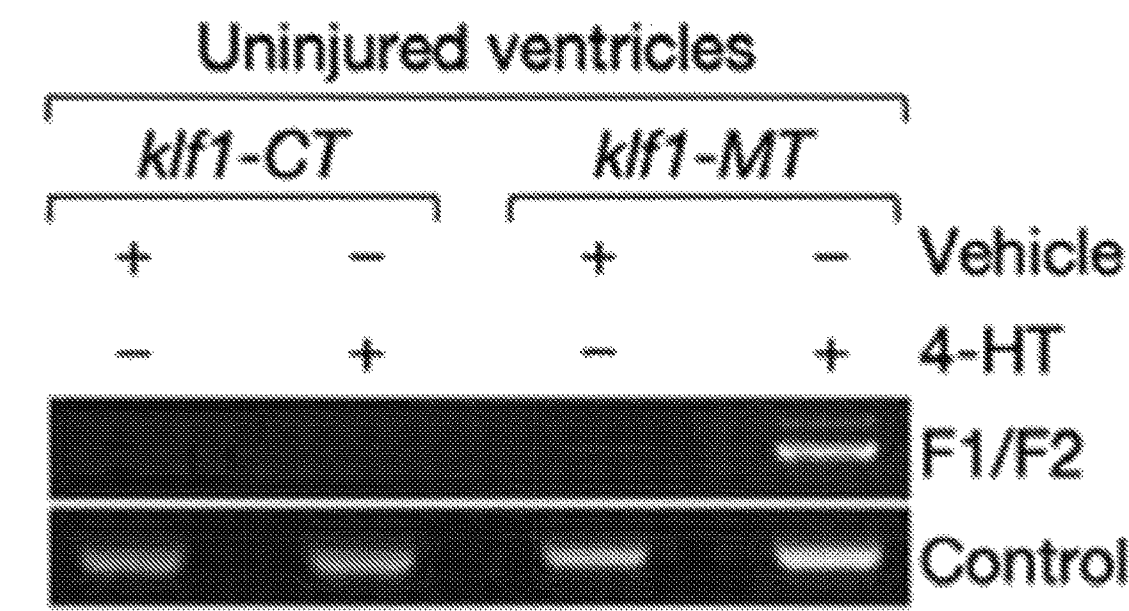
Figure 9:
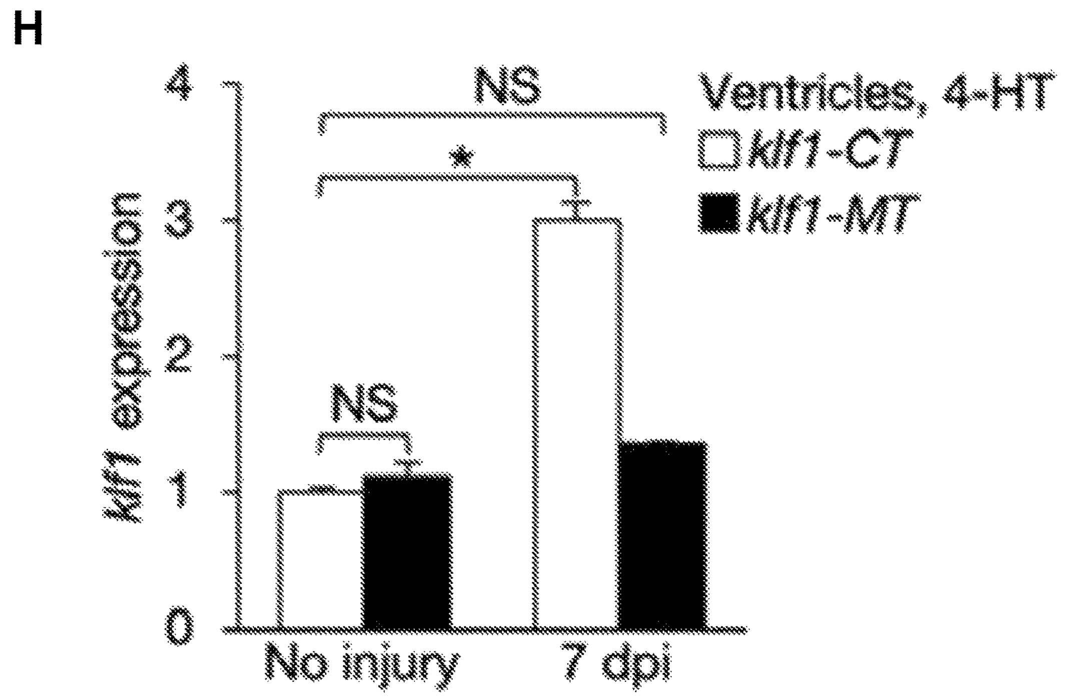

FIG. 9: Generation and characterization of a zebrafish klf1 conditional allele. Zwitch2 consists of a splice acceptor site followed by triplet poly-A sequences (3×BGHpA) and a flippase recognition target (FRT)-flanked, removable cassette (LG-tag), in which expression of enhanced green fluorescence protein (EGFP) under the control of the lens-specific alpha A-crystallin (cryaa) promoter is used for screening. The segment containing a splice acceptor site, P2A peptide sequence, and 3×BGHpA is flanked by tandem IoxP and Iox5171 sites in opposite orientations at each end. Cre-mediated recombination on this arrangement of Cre target sites permanently inverts the cassette, and the splice acceptor interferes with normal splicing patterns. (A) Schematic of the zebrafish klf1 wild-type (+) allele, transcription activator-like effector nucleases (TALEN) used to induce DNA double-strand breaks in intron 1, and the resulting conditional $klf1^{ct}$ allele. Exons are indicated by filled boxes with numbers. Binding sites for the TALEN pair are highlighted in blue, and the TALEN target site is indicated by the dashed arrow. (B) Genomic PCR analysis of the correct insertion of Zwitch2 was performed using primers indicated in (A). Primers within the LA were used as a control. (C) Southern blot analysis of the Zwitch2-modified klf1 allele. HpaI recognition sites are indicated in (A). (D) Representative image of embryos with the correct insertion of Zwitch2, showing EGFP expression in lens (arrow). (E) Genomic PCR analysis of the Zwitch2 inversion in embryos. $klf1^{ct/+}$ fish were crossed with Tg(ubb:Cre-GFP), and genomic DNA from 4-7 dpf embryos of each genotype was analyzed using PCR with primers indicated in (A). Control primers were the same as those used in (B). Cre-F and Cre-R primers were used to confirm Cre-GFP. (F) RT-qPCR analysis of 7 dpf embryos of each genotype (mean±SEM, n=3-4). A single embryo per sample was used for RT-qPCR analysis. (G) Genomic PCR analysis of the 4-hydrotamoxifen (4-HT)-dependent Zwitch2 inversion in adult hearts. klf1-CT and klf1-MT indicate zebrafish harboring $klf1^{ct/ct}$ and cmlc2:CreER; $klf1^{ct/ct}$ transgenes, respectively. The same control primers as those in (B) were used. (H) RT-qPCR analysis of 4-HT-treated, uninjured, and 7 dpi ventricles of klf1-CT and klf1-MT fish (mean±SEM, n=4). BGHp(A), bovine growth hormone polyadenylation signal; cryaa, alpha A-crystallin; dpf, days post-fertilization; dpi, days post-injury; $klf1^{+/+}$, clutch-mate control; LA, left arm; NS, not significant; RA, right arm. *p<0.05, unpaired t-test.

Figure 10:
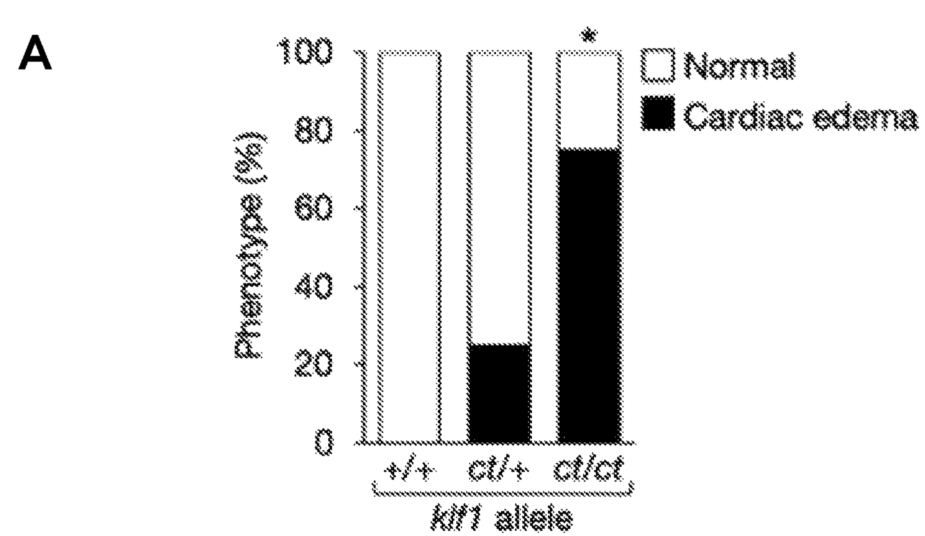
Figure 10:
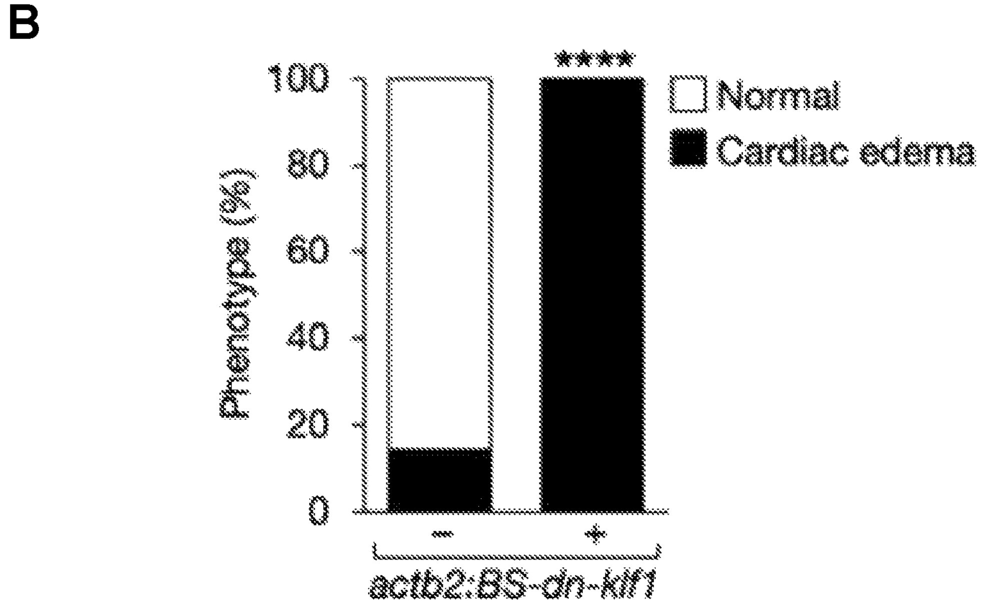
Figure 10:
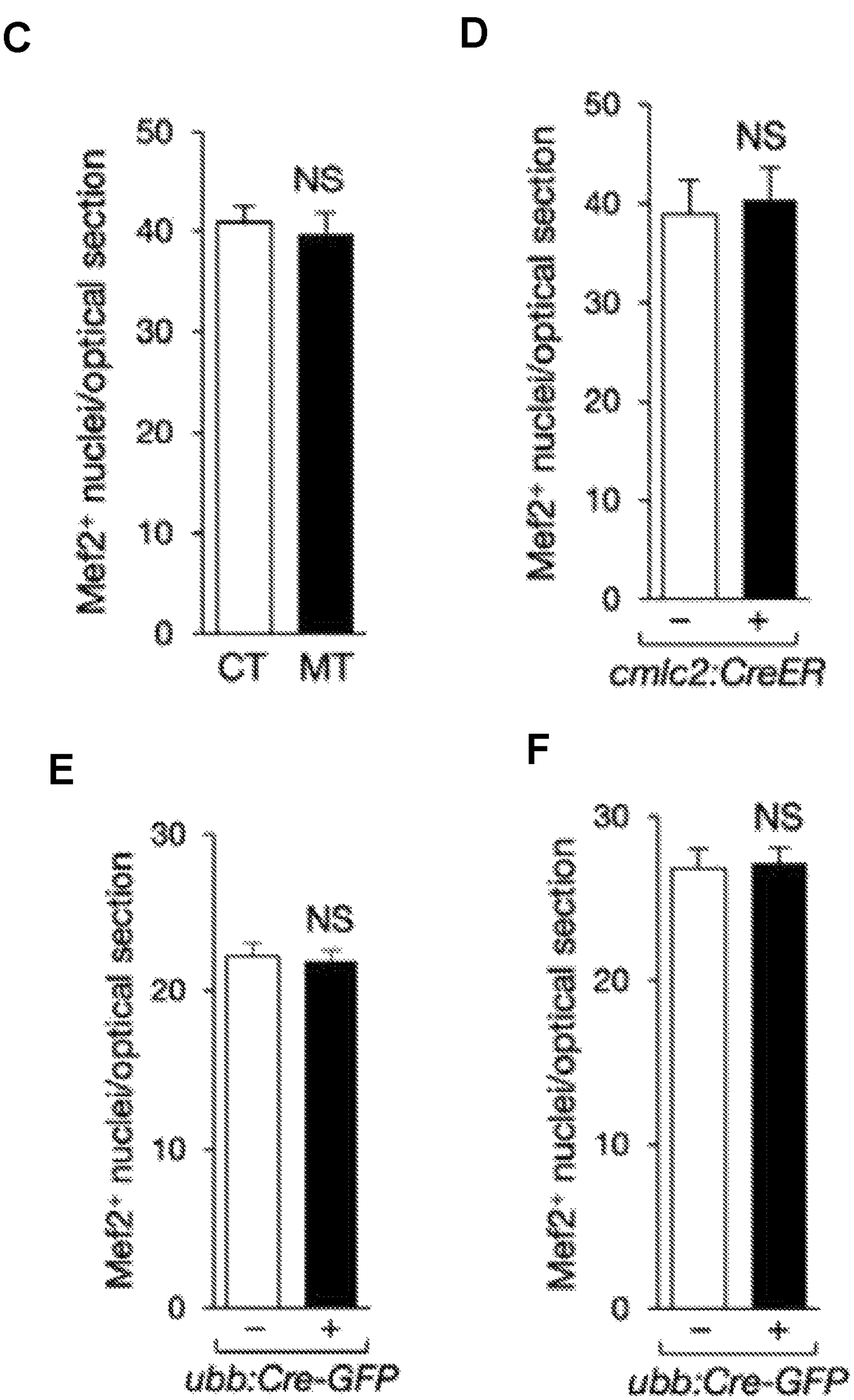

FIG. 10: Klf1 function during zebrafish development. (A) Severe cardiac edema was observed in ubb:Cre-GFP; $klf1^{ct/ct}$ embryos at 7 dpf but not in ubb:Cre-GFP; $klf1^{+/+}$ embryos (clutch-mate controls). n=3 (+/+), 4 (ct/+), or 4 (ct/ct). (B)

Severe cardiac edema was observed in ubb:Cre-GFP; actb2-BS-dn-klf1 embryos at 7 dpf (arrowheads) but not in ubb: Cre-GFP embryos (clutch-mate control). (n=7). Details of actb2-BS-dn-klf1 are described in FIG. 11A. (C) Immunofluorescence of myocyte enhancer factor 2 (Mef2) and myosin heavy chain (MHC) using ventricular sections of klf1-CT and klf1-MT embryos. The embryos were treated with 4-hydroxytamoxifen (4-HT) from 1 to 3 dpf and analyzed at 7 dpf. Quantification of Mef2$^+$ nuclei in single optical plane (mean±SEM, n=7-9). (D) Immunofluorescence of Mef2 and MHC using ventricular sections of actb2:BS-dn-klf1 (clutch-mate control) and cmlc2:CreER; actb2:BS-dn-klf1 embryos. Embryos were treated with 4-HT from 1 to 3 dpf and analyzed at 7 dpf. Quantification of Mef2$^+$ nuclei in single optical plane (mean±SEM, n=6-8). (E) Immunofluorescence of Mef2 and MHC using ventricular sections of klf1$^{ct/ct}$ (clutch-mate controls) and ubb:Cre-GFP; klf1$^{ct/ct}$ embryos at 4 dpf. Quantification of Mef2$^+$ nuclei in single optical plane (mean±SEM, n=5-7). (F) Immunofluorescence of Mef2 and MHC using ventricular sections of actb2:BS-dn-klf1 (clutch-mate controls) and ubb:Cre-GFP; actb2:BS-dn-klf1 embryos at 4 dpf. Quantification of Mef2$^+$ nuclei in single optical plane (mean±SEM, n=8-9). Note that cardiac edema was evident from 5 dpf onwards but not at 4 dpf. dpf, day post-fertilization. *p<0.05, ****p<0.001 by $\chi^2$ test (A), Fisher's exact test (B), or unpaired t-test (C-F).

Figure 11:
Figure 11:
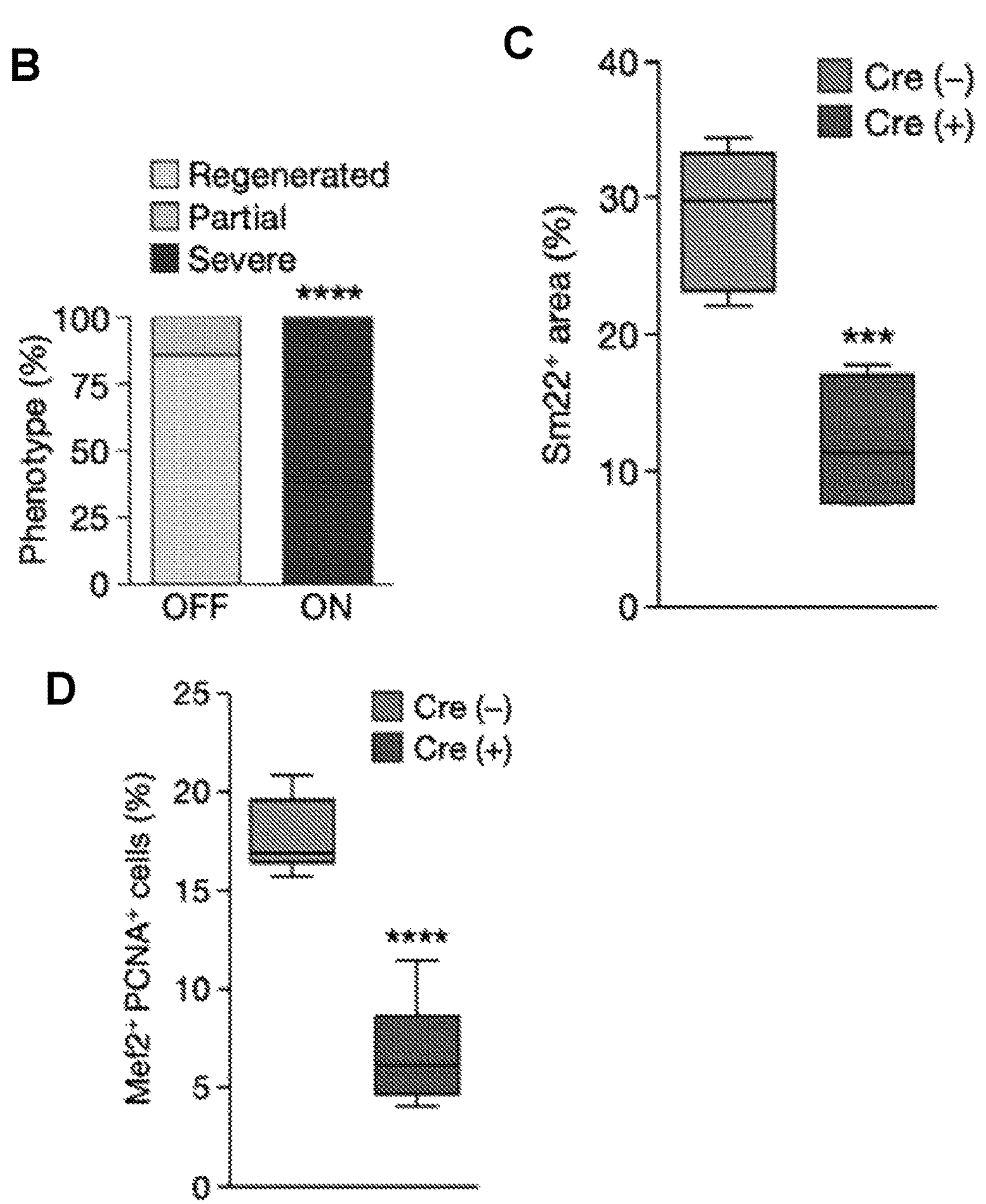

FIG. 11: Impaired cardiac regeneration with the expression of dominant-negative Klf1 in zebrafish. (A) The Tg(actb2:IoxP-TagBFP-STOP-IoxP-dn-klf1)$^{vcc22}$ zebrafish line (hereafter actb2:BS-dn-klf1) was established and crossed with cmlc2:CreER for cardiomyocyte-specific expression of dn-Klf1 with 4-hydroxytamoxifen (4-HT) treatments. EnR, engrailed repressor domain. (B) Picro-Mallory staining was performed and regeneration quantified (n=5-7). (C) Immunofluorescence of smooth muscle protein 22α (Sm22) and myosin heavy chain (MHC) was performed and box plots prepared to show the quantification of Sm22$^+$ MHC$^+$ areas from (n=4-5). (D) Immunofluorescence of the myonuclear marker Mef2 and proliferation cell nuclear antigen (PCNA) was performed and box plots prepared to show the quantification of Mef2$^+$PCNA$^+$ cells (n=9-10). *p<0.005, **p<0.001 by Fisher's exact test (B) or unpaired t-test (C, D). Scale bars, 50 μm.

Figure 12:
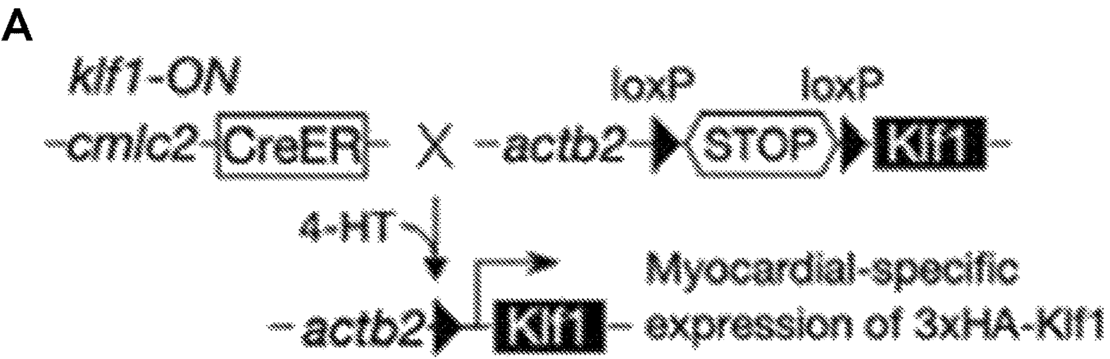
Figure 12:
Figure 12:
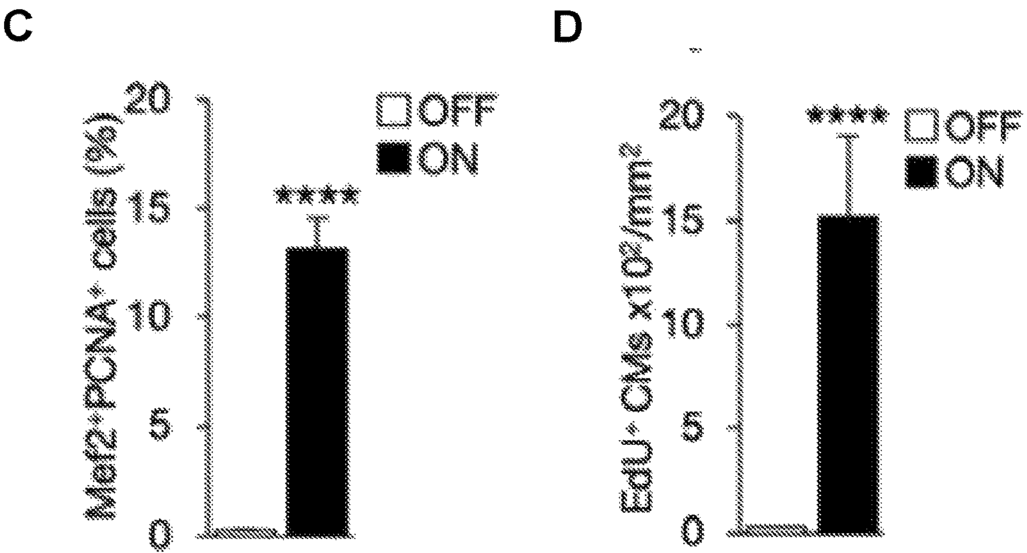
Figure 12:
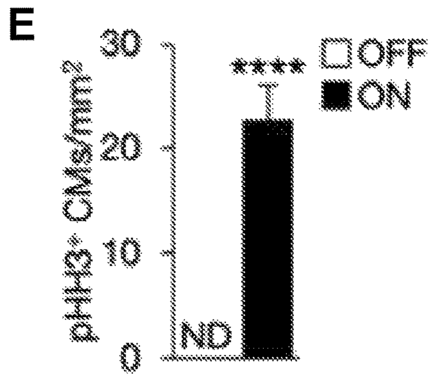
Figure 12:
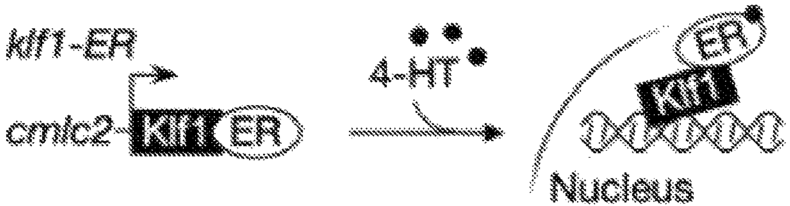
Figure 12:
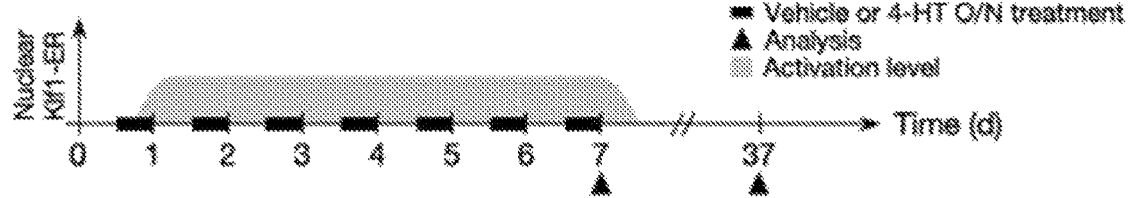
Figure 12:
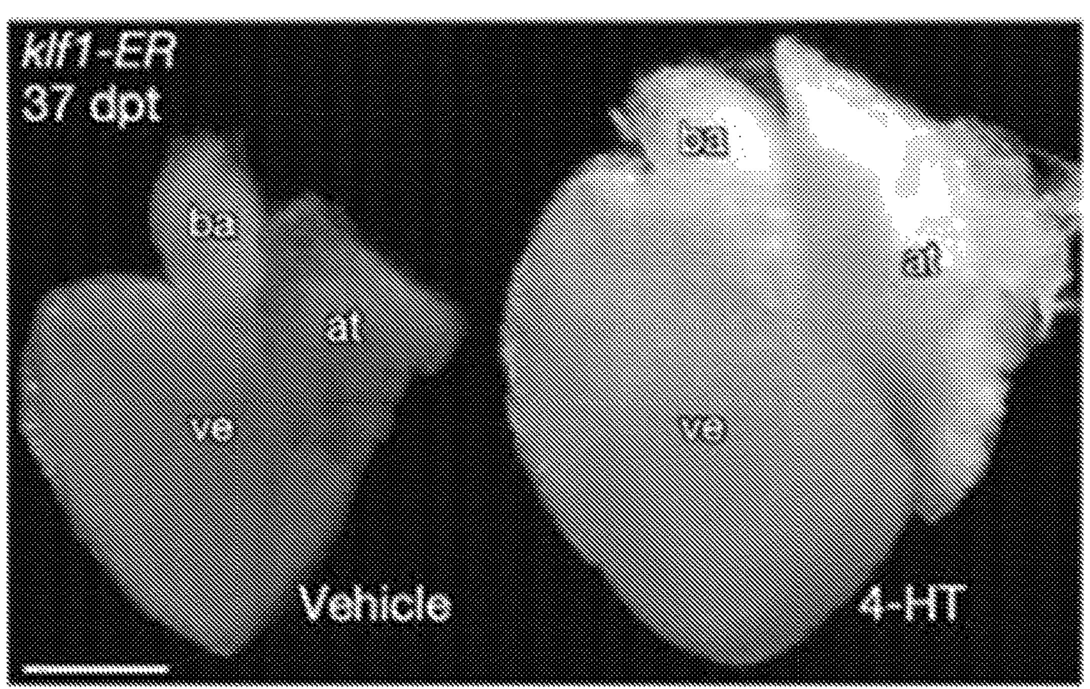
Figure 12:
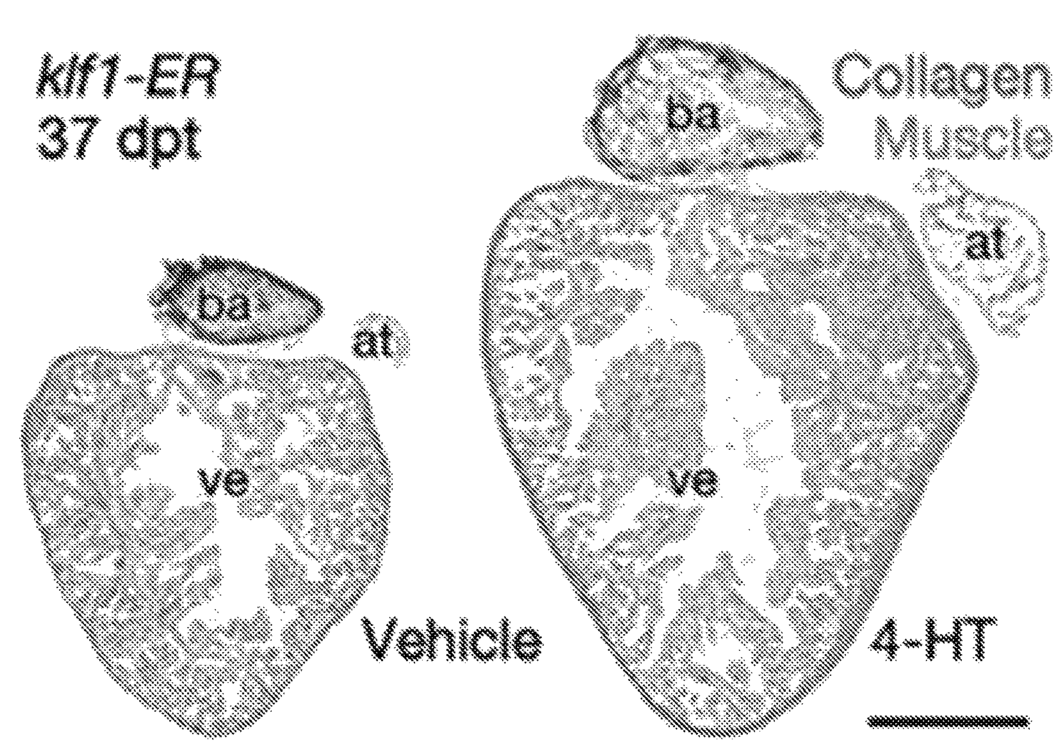
Figure 12:
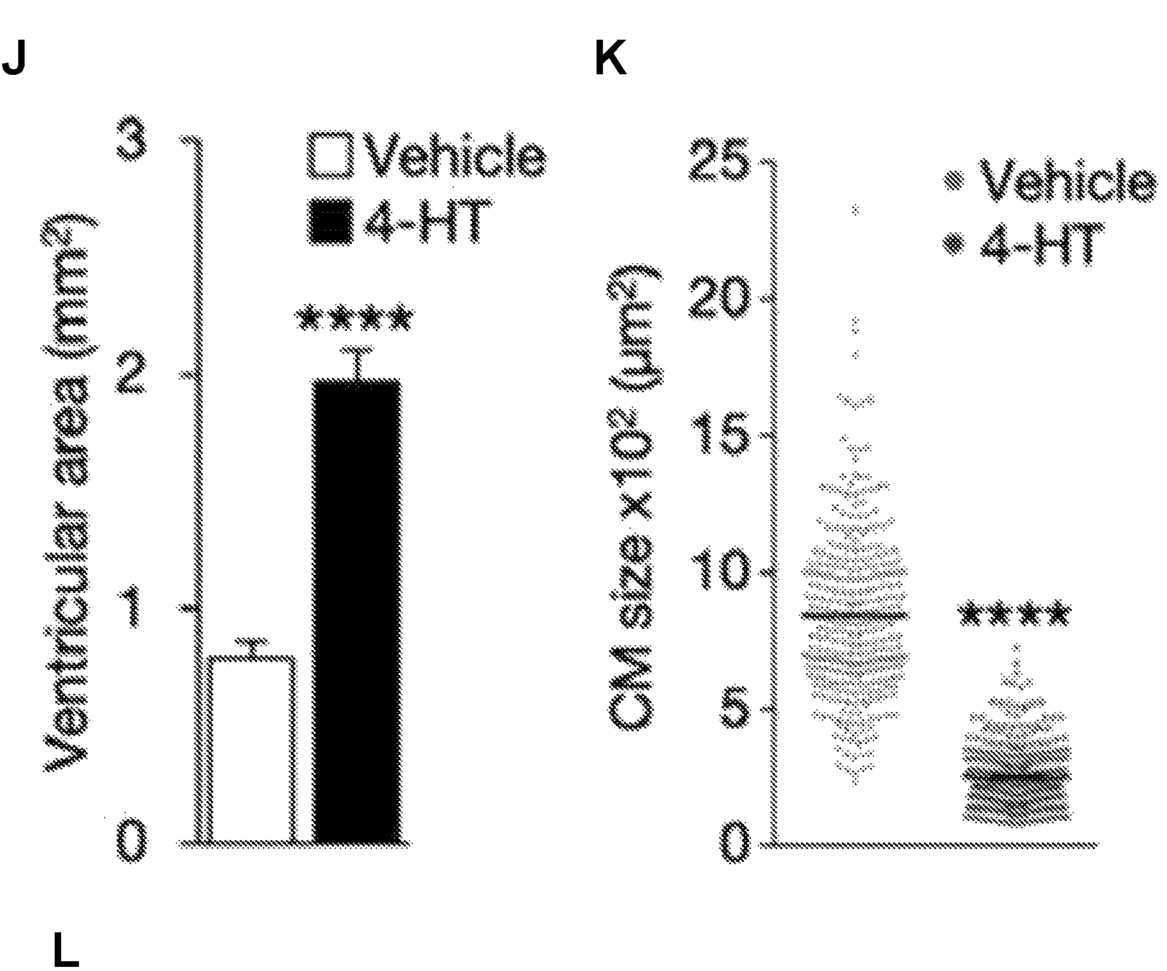
Figure 12:
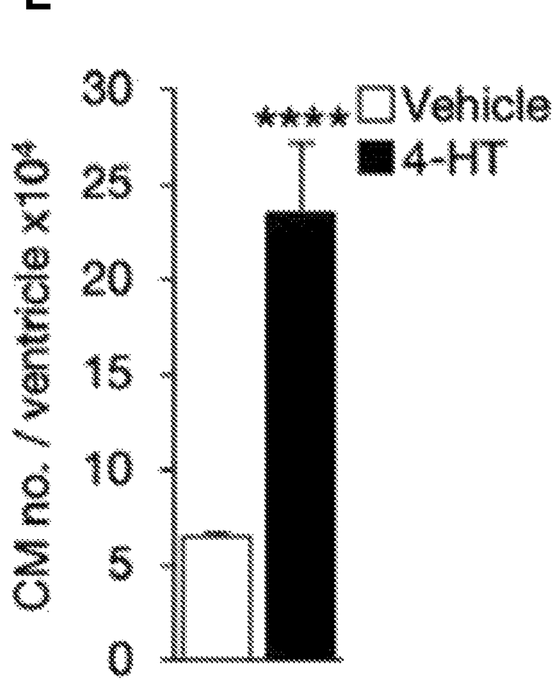

FIG. 12: Gain-of-function analysis of zebrafish myocardial Klf1. (A) Tg(actb2:IoxP-TagBFP-STOP-IoxP-3×HA-klf1)$^{vcc29}$ fish were crossed with cmlc2:CreER fish, and double-transgenic fish and Cre-negative clutch-mates were referred to as klf1-ON and klf1-OFF, respectively. (B) The 4-hydroxytamoxifen (4-HT) treatment regimen used for klf1-OFF and klf1-ON fish. Immunofluorescence of myosin heavy chain (MHC) and smooth muscle protein 22α (Sm22), troponin C (TnC) or Alcam was performed. Sarcomere disassembly was detected from day 7 onward by immunofluorescence of Actinin and TEM. (C) Immunofluorescence of the myocyte nuclear marker myocyte enhancer factor 2 (Mef2) and proliferating cell nuclear antigen (PCNA) was performed and quantified (mean±SEM, n=7). (D) EdU incorporation assay. Images were collected on the xz and yz planes of magnified, demarcated regions and quantified (mean±SEM, n=8). EdU$^+$ cardiomyocytes were counted only when EdU$^+$ nuclei were cmlc2:GFP$^+$ myocardium in z planes. (E) Immunofluorescence of phosphohistone H3 (pHH3) was performed and quantified (mean±SEM, n=6). pHH3$^+$ cardiomyocytes were counted only when pHH3$^+$ nuclei were in cmlc2:GFP$^+$ myocardium in z planes. (F) Tg(cmlc2:3×HA-klf1-ER; cryaa:TagBFP)$^{vcc32}$ (hereafter, klf1-ER), a transgenic system allowing transient nuclear translocation of Klf1 in cardiomyocytes. (G), The 4-HT treatment regimen used for klf1-ER fish. klf1-ER fish were treated with Vehicle or 4-HT O/N for 7 days, followed by a recovery period for 30 days under normal aquarium conditions. (H) Gross morphology of klf1-ER hearts analyzed 30 days after the 7-day treatment with Vehicle or 4-HT. (I) Picro-Mallory staining of heart sections of (H). (J) Quantification of (I). (K, L) Cell size quantification (K) [n=332 (Vehicle), 326 (4-HT)], and cell number counted (L) (mean±SEM, n=3) of dissociated CMs of (H). Representative data from two independent analysis are shown in (K) and (L). at, atrium; ba, bulbus arteriosus; DAPI, 4',6-diamidino-2-phenylindole; dpt, days post-treatment; EdU, 5-ethynyl-2'-deoxyuridine; O/N, overnight; TEM, transmission electron microscope; Veh, vehicle; vt, ventricle. *p<0.05, p<0.01, **p<0.001 by Mann-Whitney U test (C, D, E) or unpaired t-test (K, L). Scale bars 500 μm in (H, I).

Figure 13:
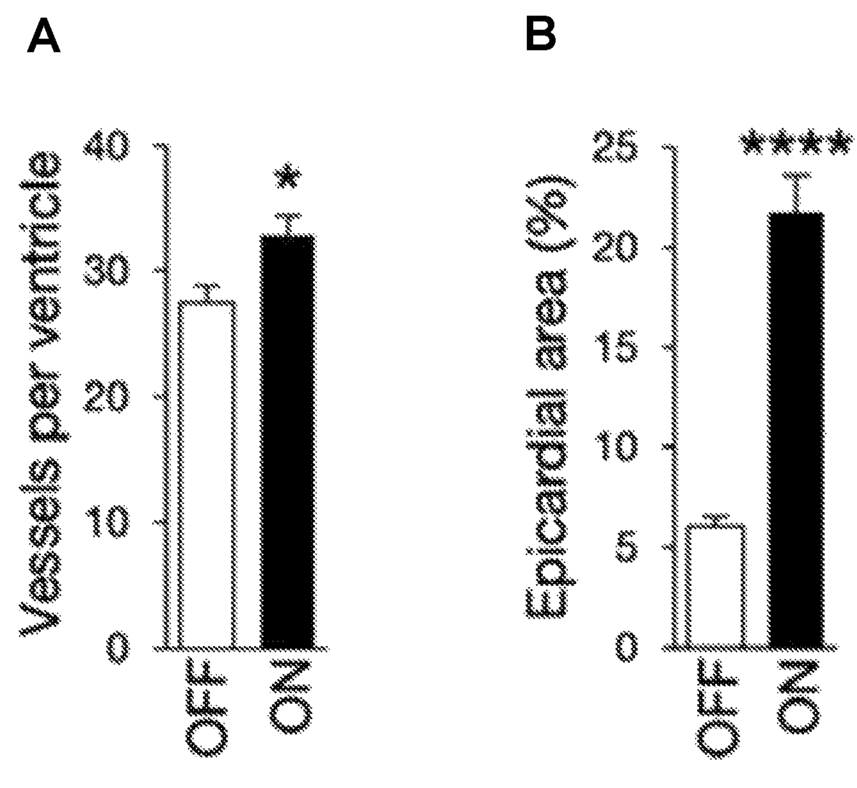
Figure 13:
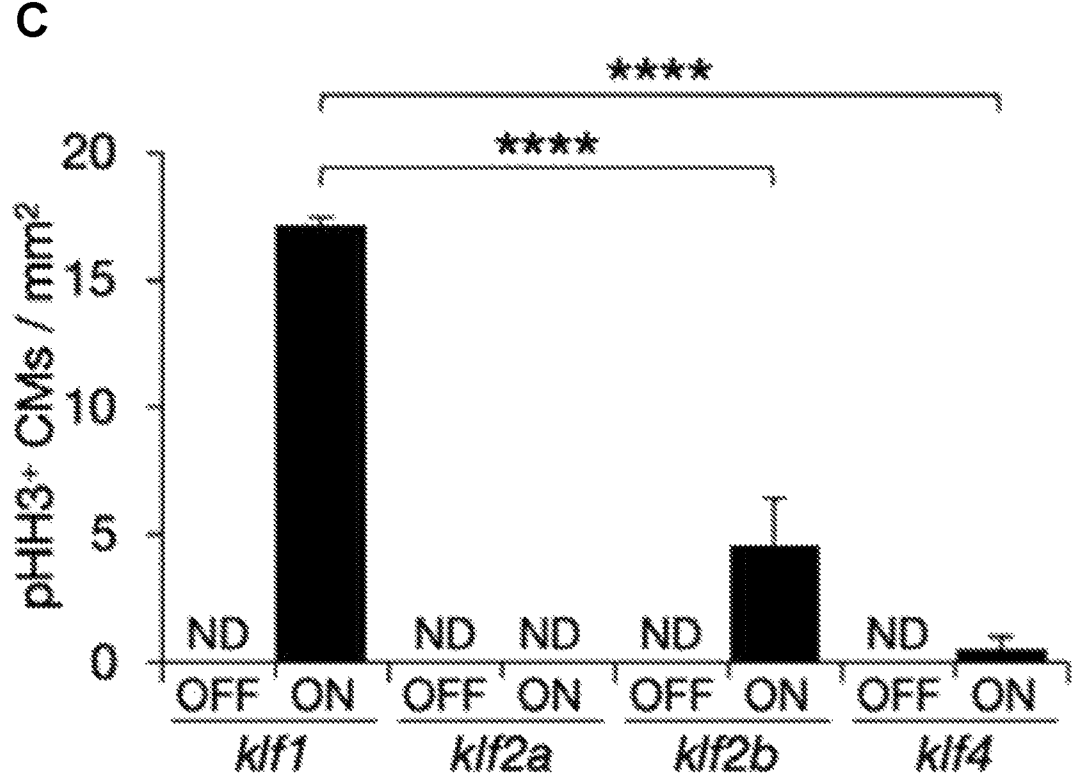

FIG. 13: Functional analysis of Klf1-related family members and non-myocardial effects of Klf1 expression. Quantification of vasculature (A) (mean±SEM, n=4) and epicardial cell areas (B) (mean±SEM, n=3-4) was performed using heart tissue sections of klf1-ON or klf1-OFF. (C) Quantification of pHH3$^+$Actinin$^+$ cardiomyocytes in sections of hearts expressing Klf1, Klf2a, Klf2b, and Klf4 (mean±SEM, n=4). Klf2a, Klf2b, and Klf4 were expressed in cardiomyocytes in an inducible manner as described for klf1-ON (FIG. 12A). pHH3$^+$ nuclei within Actinin$^+$ myocardium in z planes were counted as mitotic cardiomyocytes. pHH3, phosphohistone H3. *p<0.05, ****p<0.001 by unpaired t-test.

Figure 14:
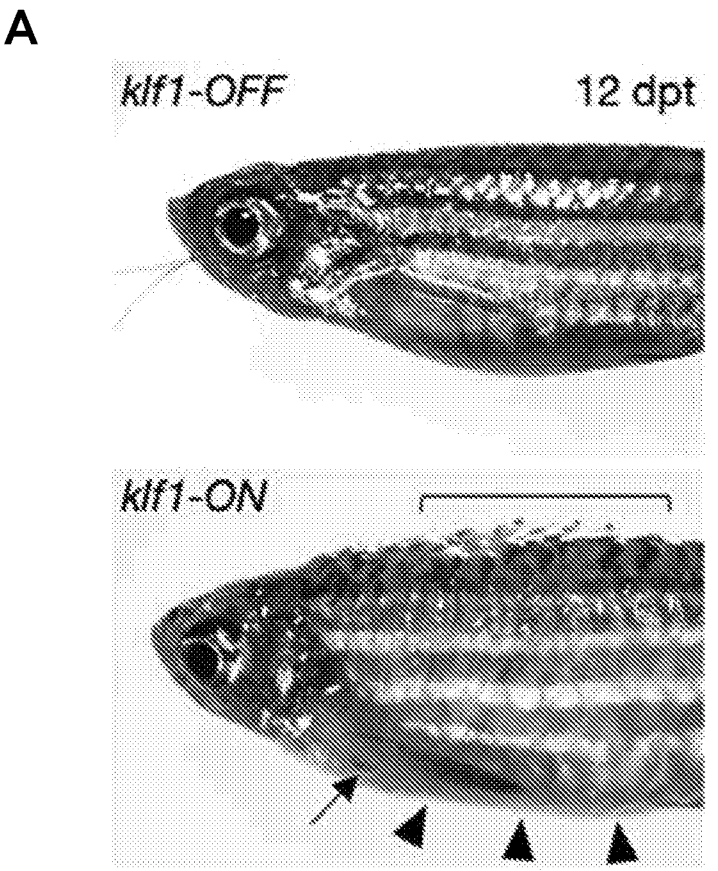
Figure 14:
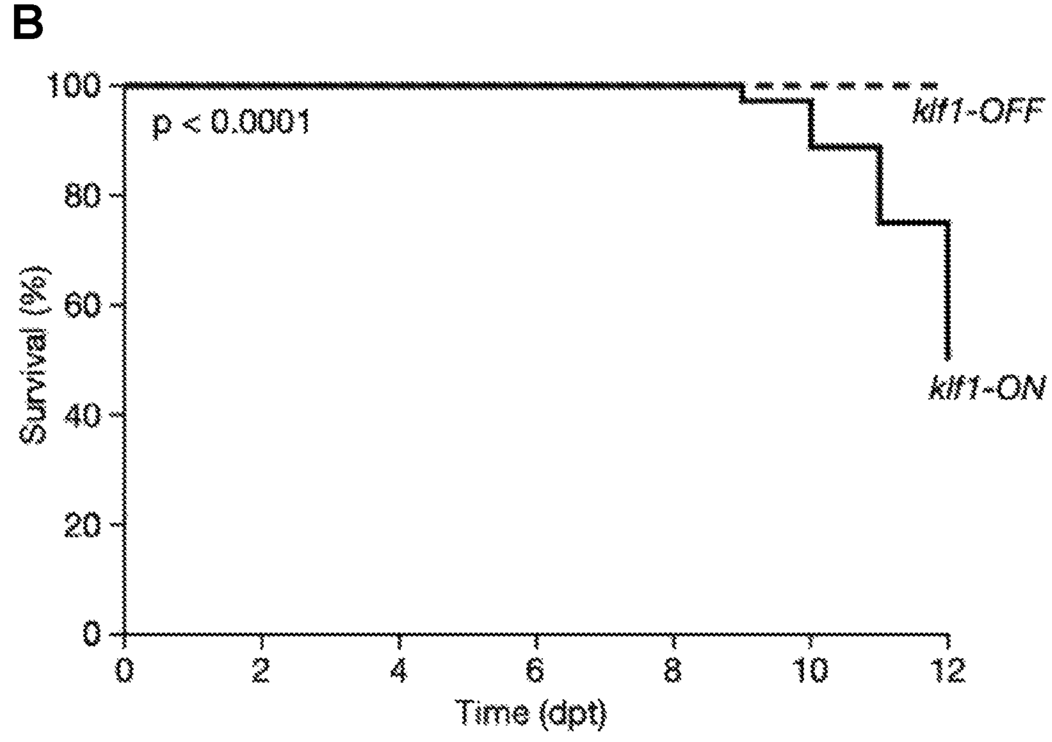

FIG. 14: Cardiac dysfunction in klf1-ON zebrafish. (A) Heart failure-like phenotypes such as raised scale (bracket), blood congestion (arrow), and abdominal edema (arrowheads), in klf1-ON fish at 12 dpt. (B), Kaplan-Meier survival curves demonstrating a significant reduction in survival in klf1-ON fish (n=10; p<0.0001, log-rank test).

Figure 15:
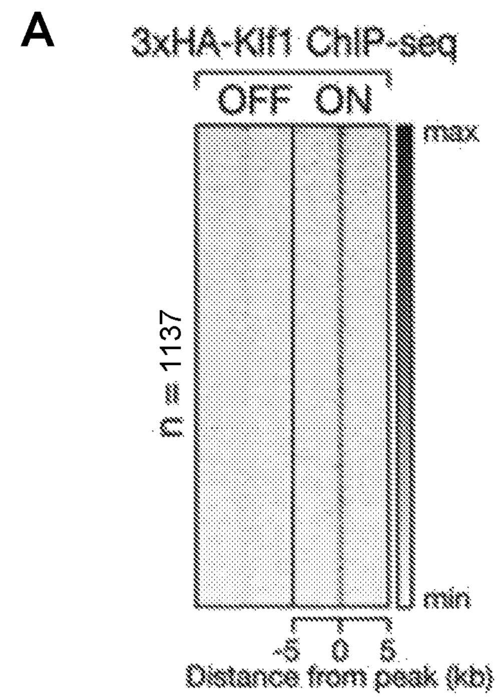
Figure 15:
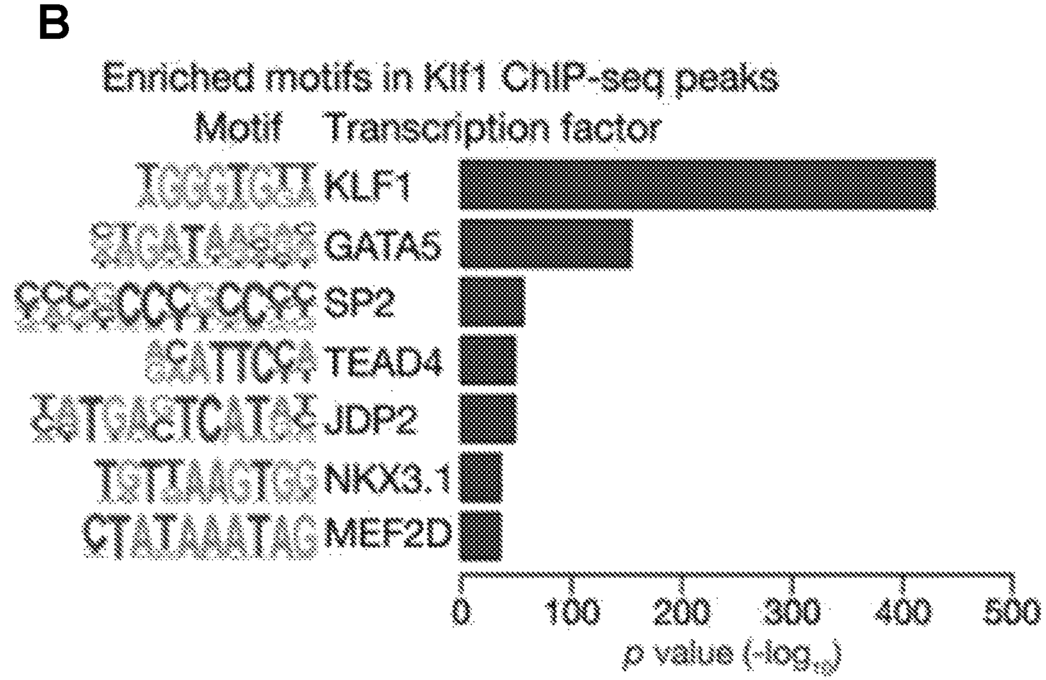
Figure 15:
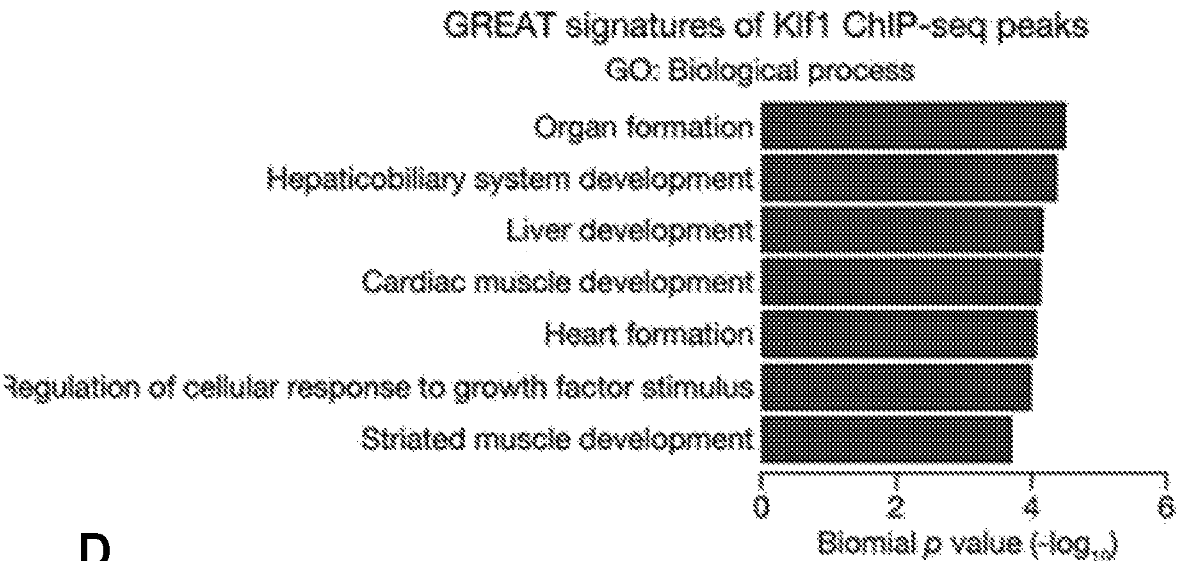
Figure 15:
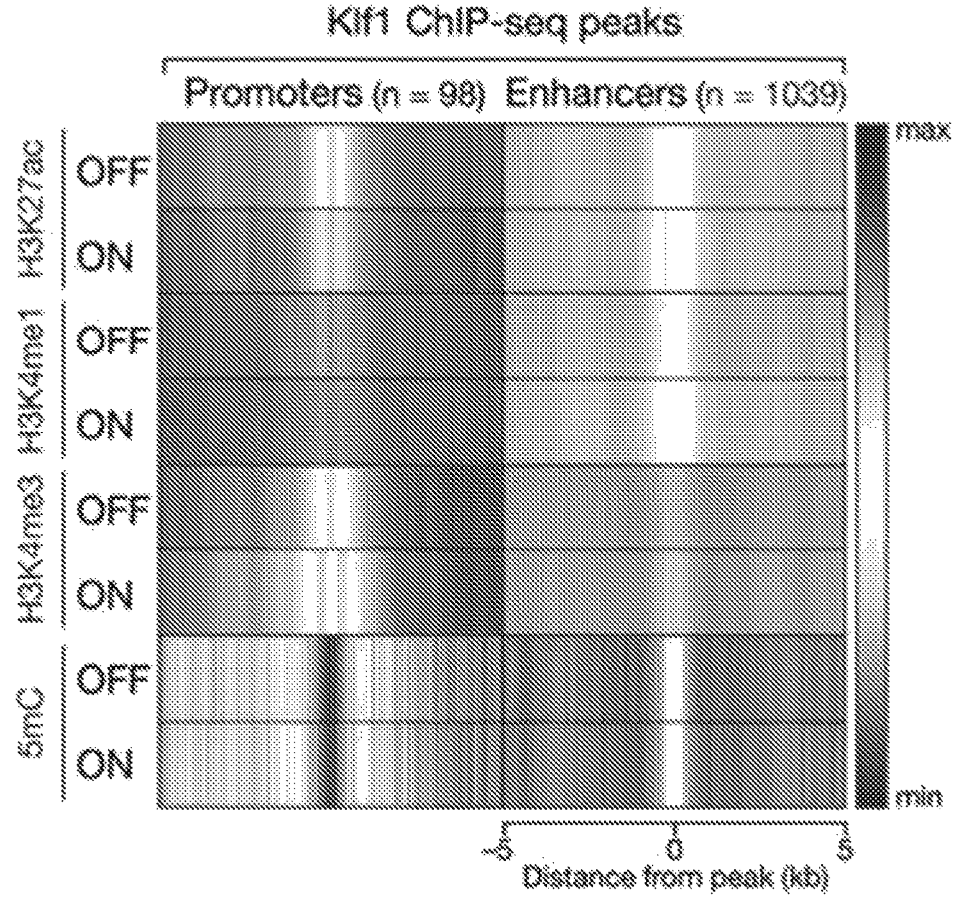
Figure 15:
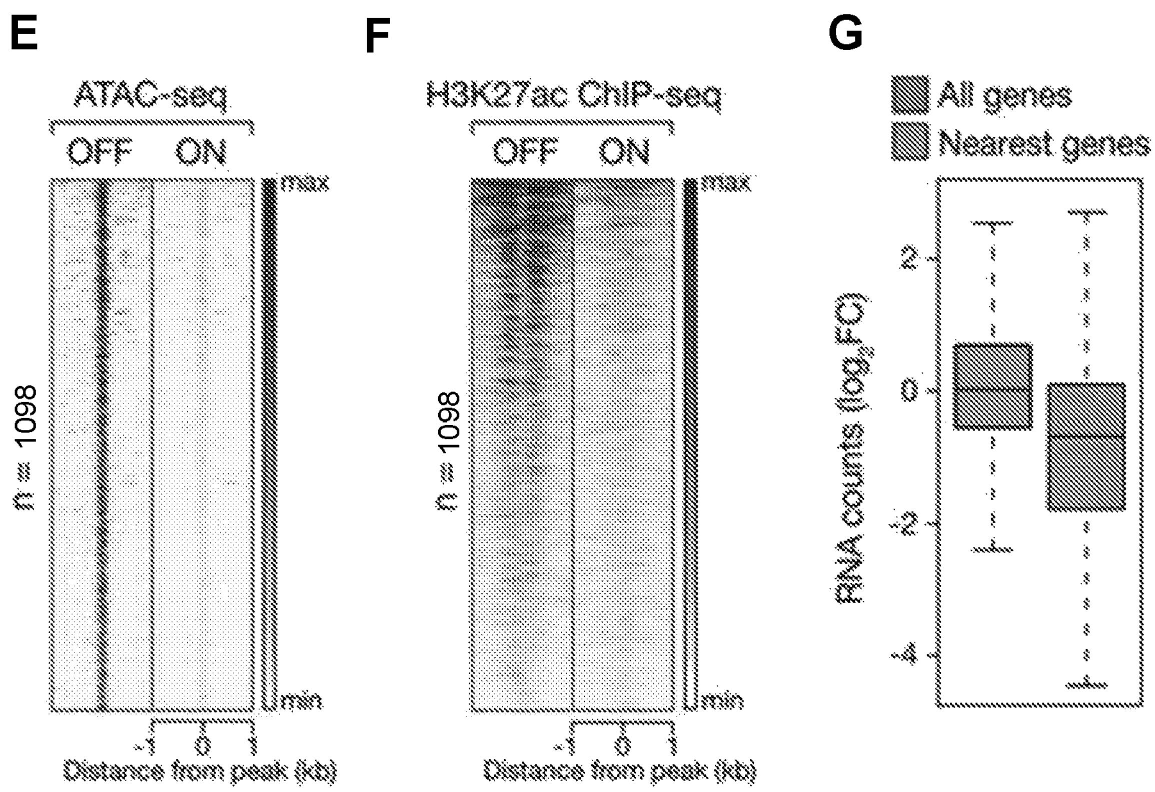
Figure 15:
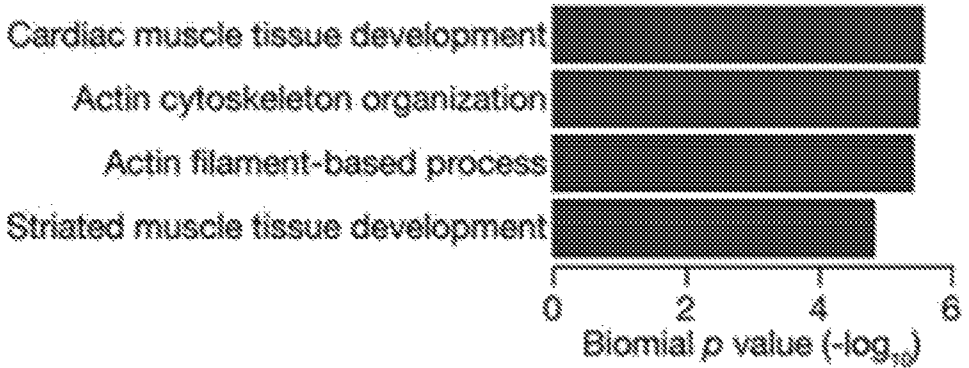
Figure 15:
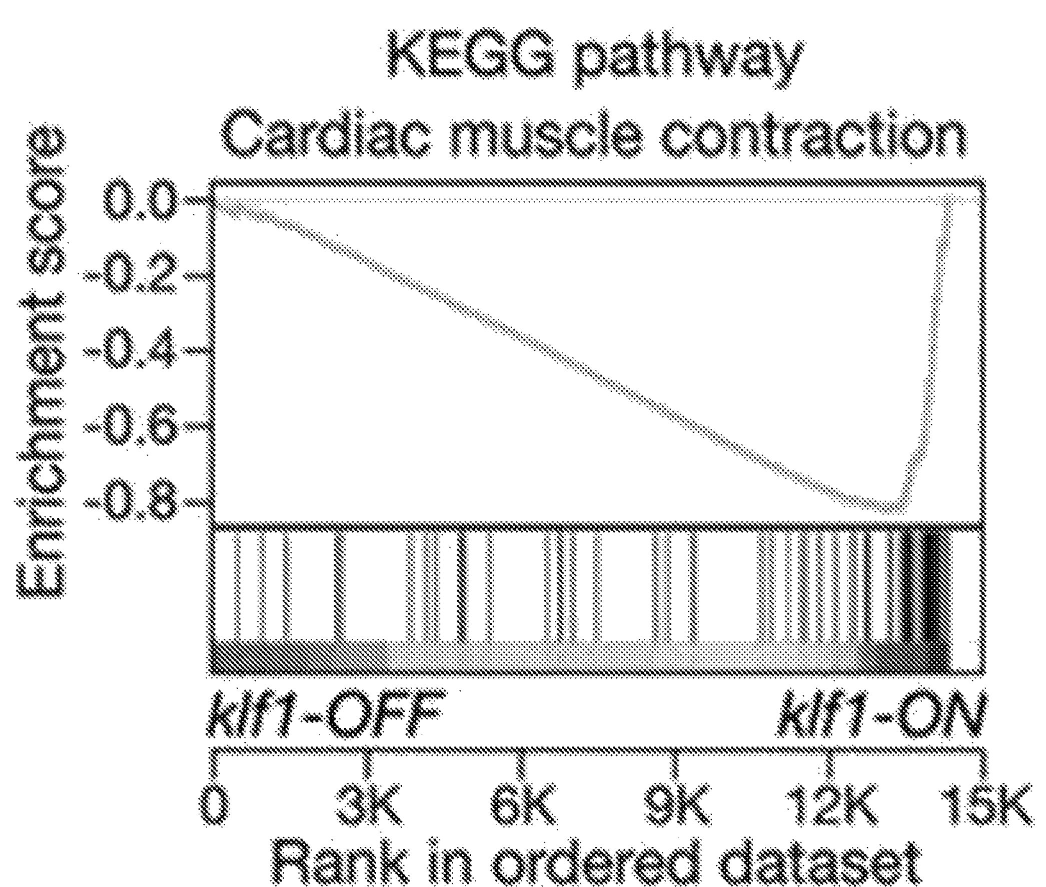

FIG. 15: Epigenetic analysis of Klf1-induced cardiac regrowth in zebrafish. (A, B) Heatmaps of 3×HA-Klf1 ChIP-seq read density from klf1-OFF and ON ventricles at 7 dpt were generated (A) and enriched motifs within ±100 bp of the summits of the Klf1 peaks (B). (C) Functional annotation of the Klf1 peaks using GREAT. (D) Sorted heatmaps of 5-methylcytosine (5mC) levels and normalized ChIP-seq read densities for H3K27ac, H3K4me1, or H3K4me3 at Klf1 ChIP-seq peaks in klf1-OFF and ON ventricles at 7 dpt. The Klf1 ChIP-seq peaks were divided into two categories based on the H3K27ac/H3K4me1 (enhancers) and H3K4me3 profiles (promoters), and the heatmaps are presented accordingly. (E) Heatmaps of ATAC-seq reads obtained from klf1-OFF and ON ventricles at 7 dpt. (F) Heatmaps of H3K27ac ChIP-seq peaks centered around the differentially enriched ATAC-seq peaks from (E). (G) Box plots showing mRNA expression of all genes and genes nearest the reduced ATAC-seq peaks in klf1-ON hearts from (E). (H) Functional annotation of the reduced ATAC-seq peaks in klf1-ON hearts using GREAT. (I) A GSEA plot demonstrating enrichment scores of the KEGG gene set of cardiac muscle contraction transcripts in RNA-seq data of klf1-OFF and ON hearts at 7 dpt (FDR<$1.0\times10^{-6}$). bp, base pairs; ChIP, chromatin immunoprecipitation; dpt, day post-treatment; FC, fold-change; FDR, false discovery rate; GREAT, genomic regions enrichment of annotations tool; GSEA, gene set enrichment analysis; KEGG, Kyoto Encyclopedia of Genes and Genomes.

Figure 16:
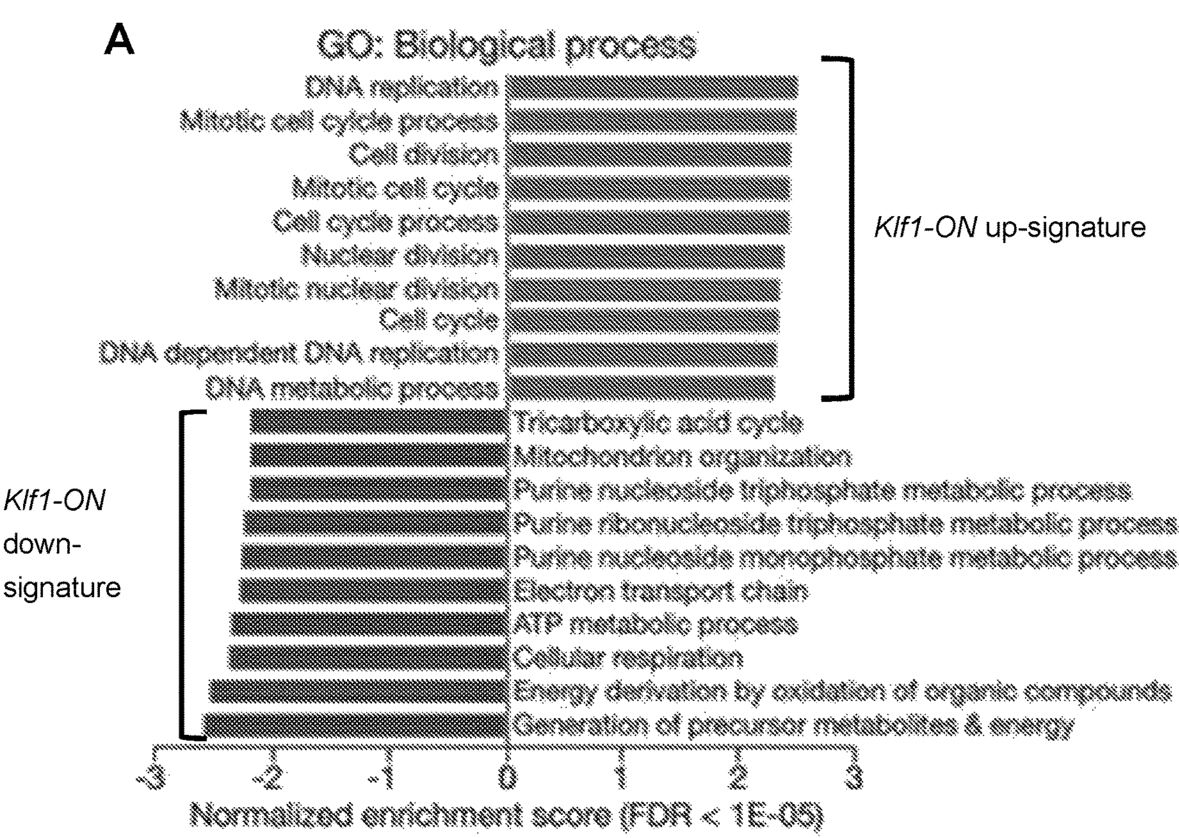
Figure 16:
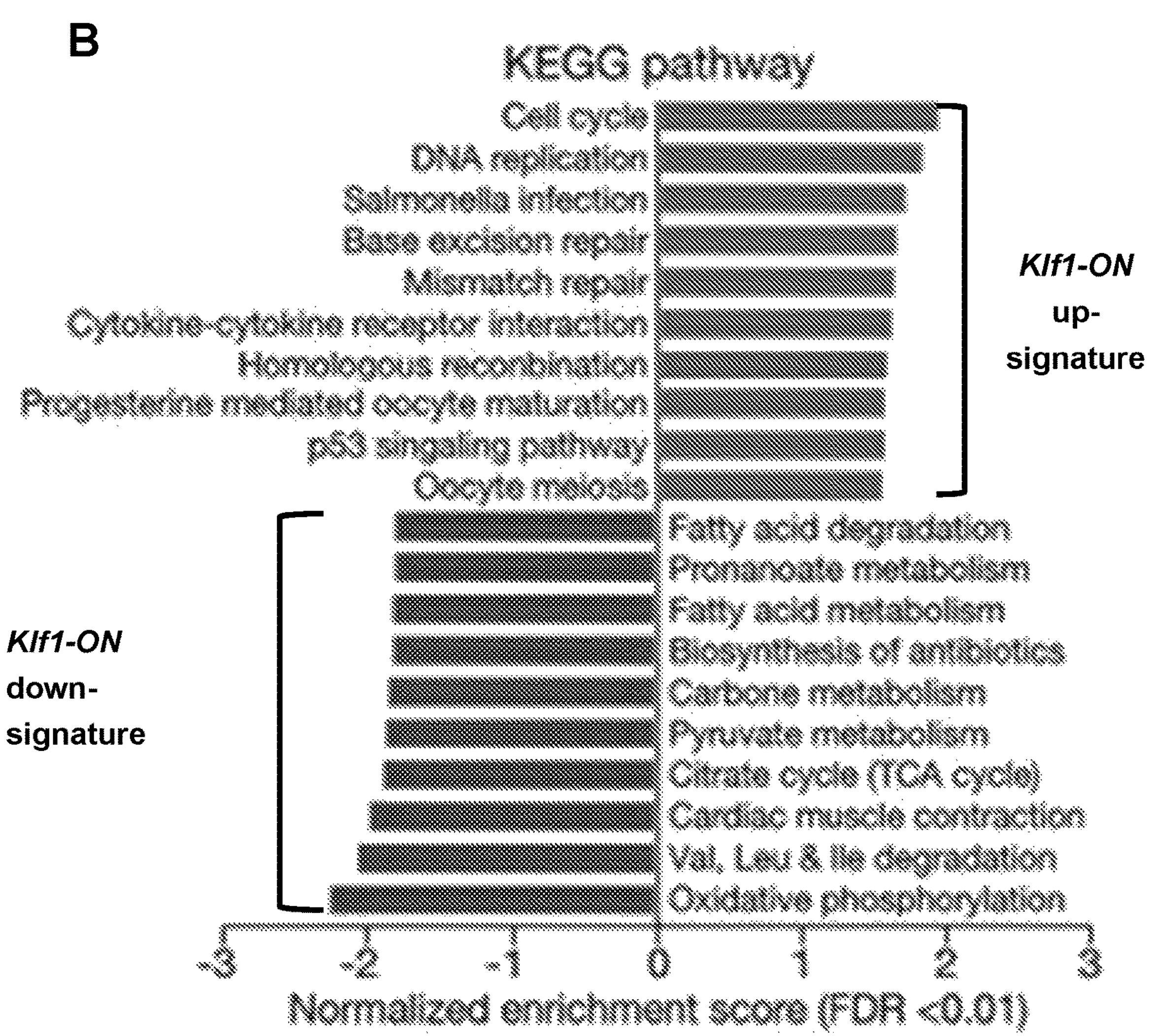
Figure 16:
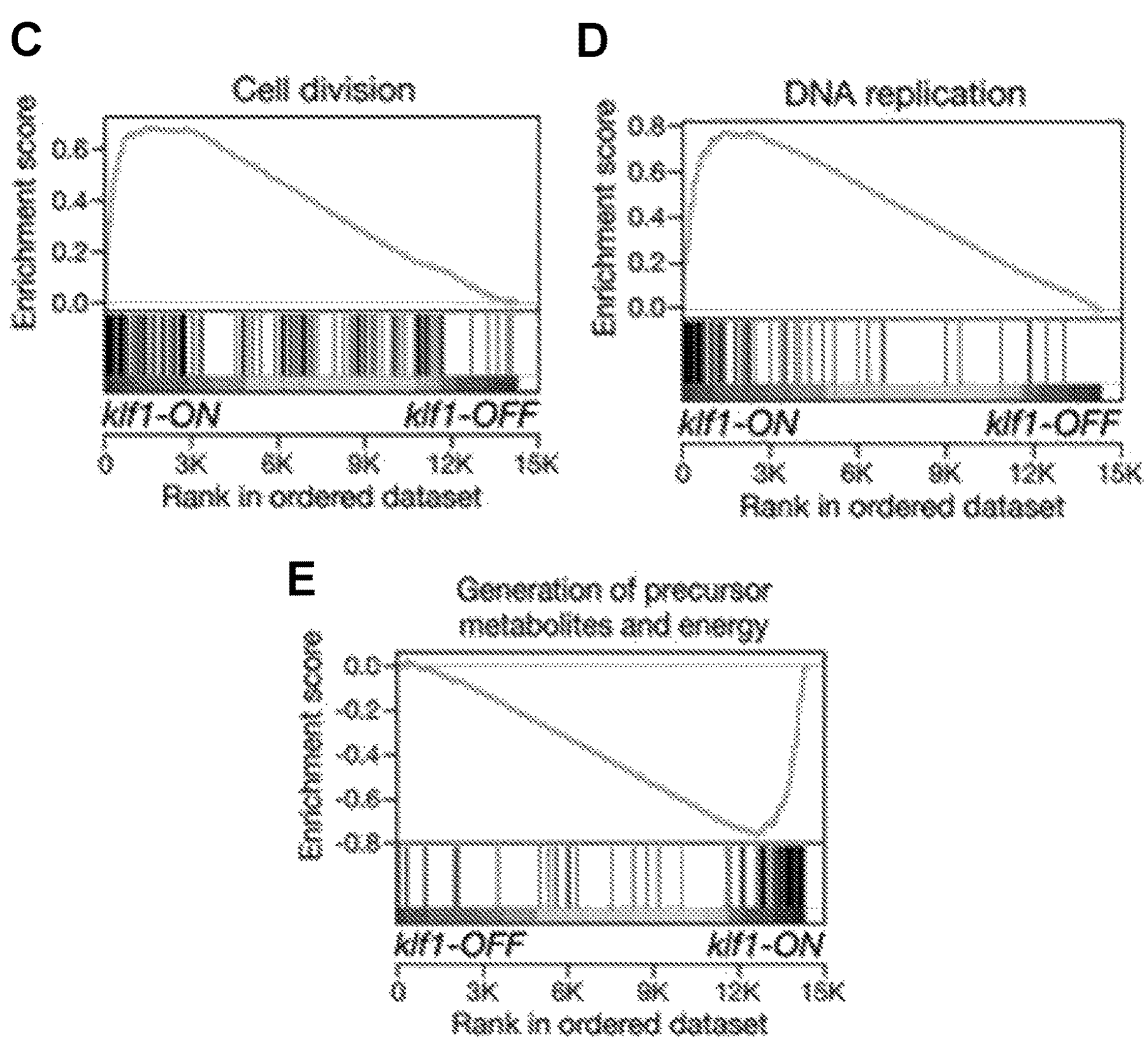
Figure 16:
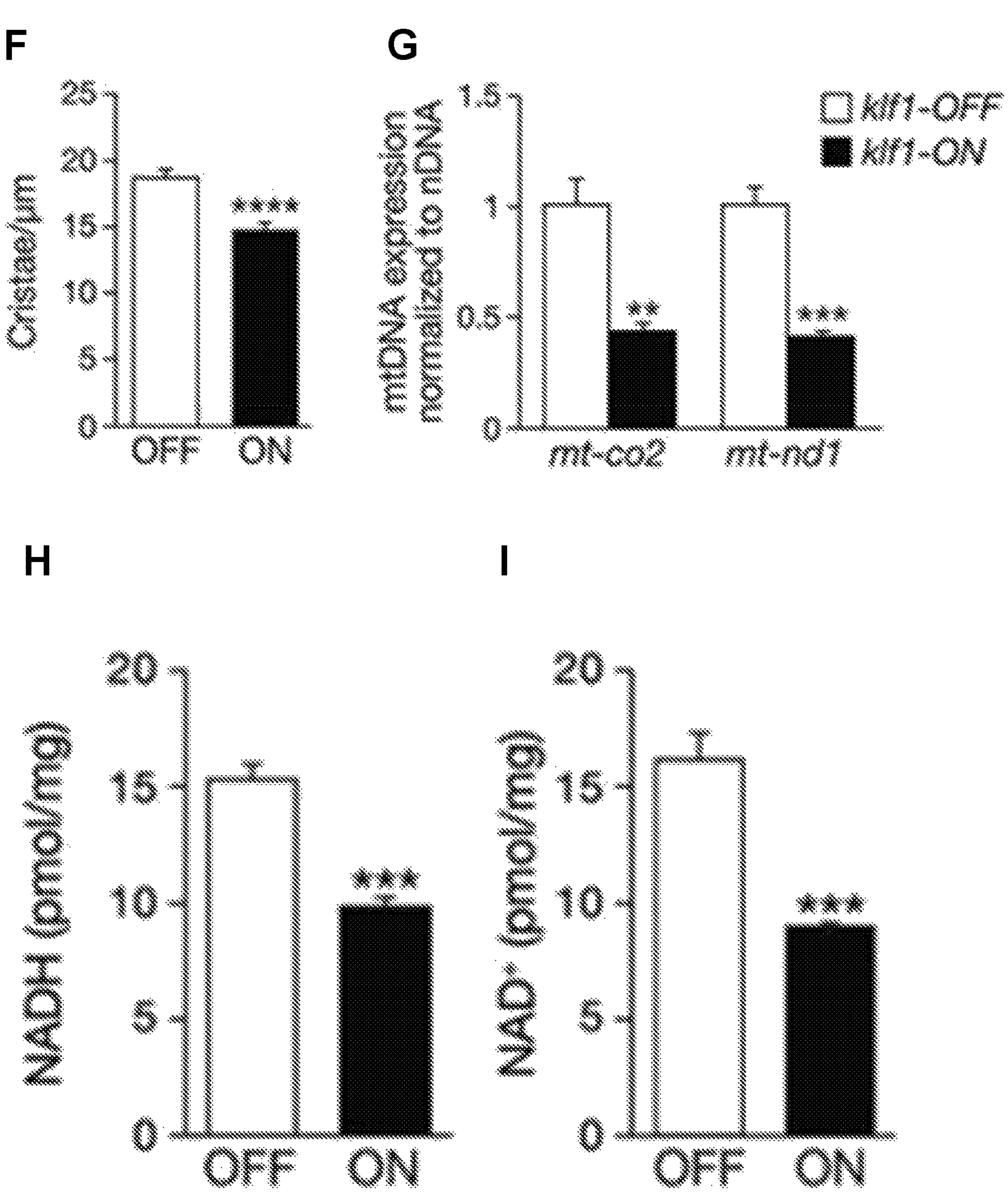
Figure 16:
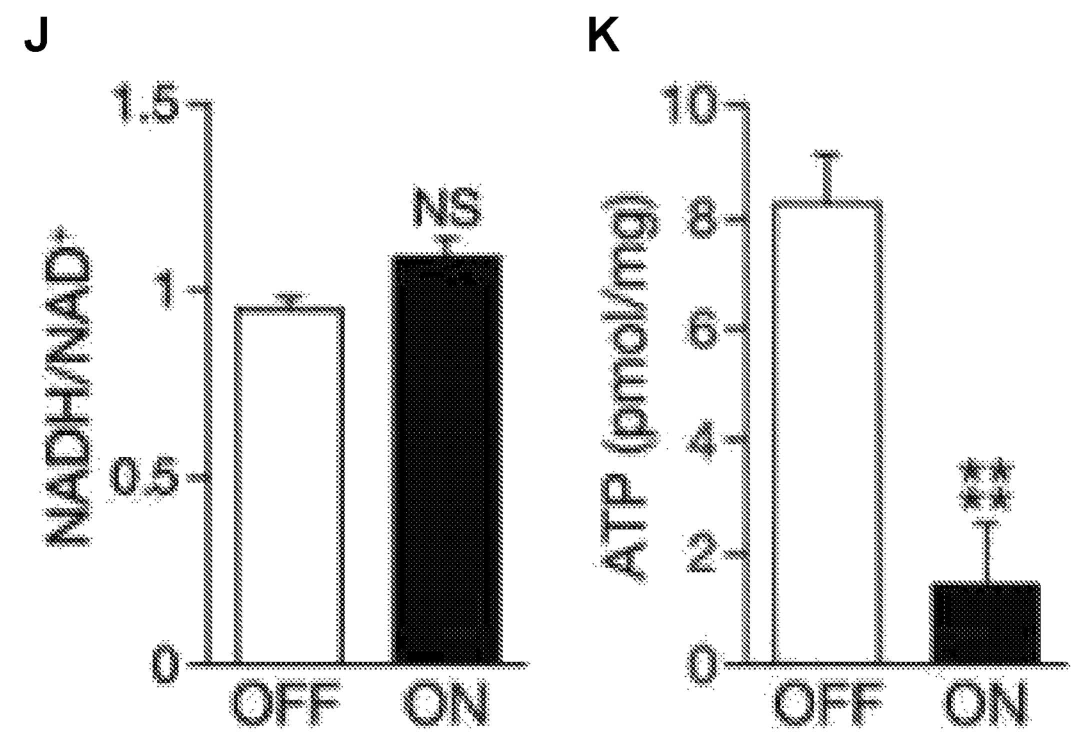
Figure 16:
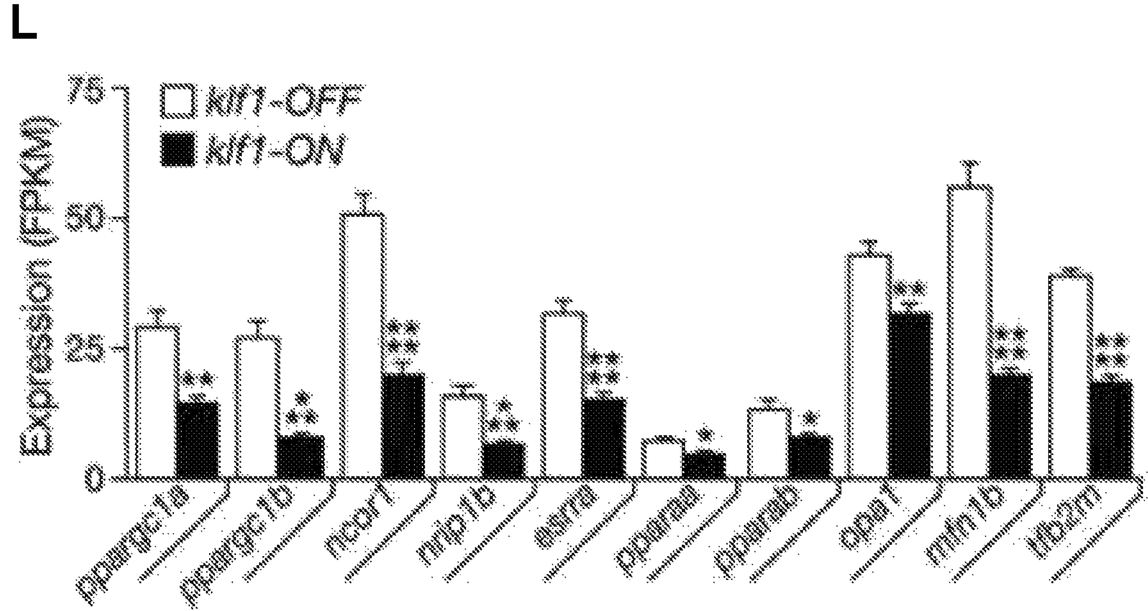
Figure 16:
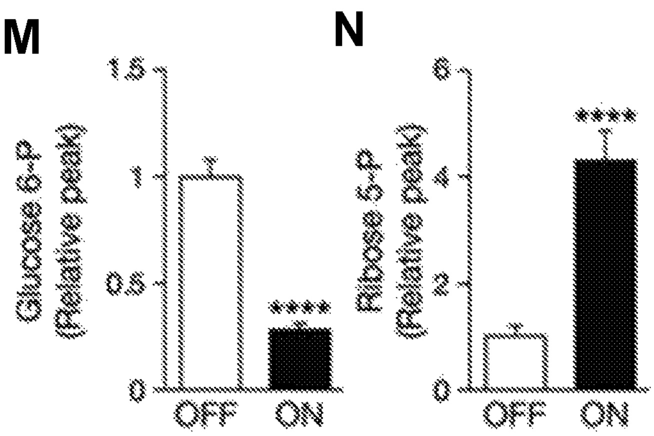
Figure 16:
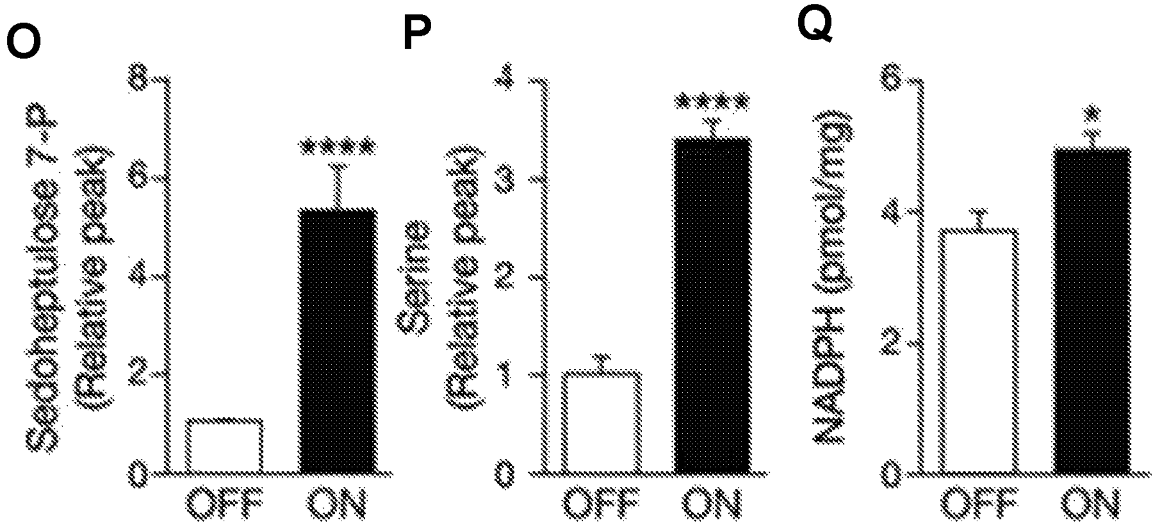
Figure 16:
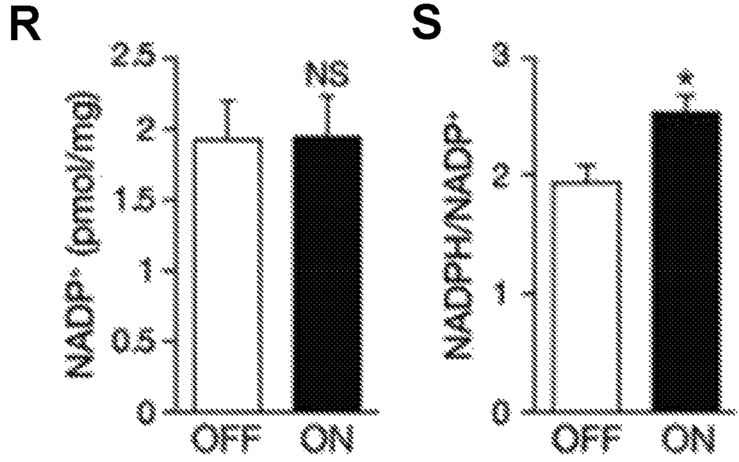

FIG. 16: Transcriptomic and metabolomic analysis of Klf1-induced cardiac regrowth in zebrafish. (A, B) Enrichment analysis of RNA-seq data of klf1-OFF and ON hearts at 7 dpt demonstrating upregulated and downregulated gene sets from GO biological process (A) and KEGG pathways (B). (C-E), GSEA plots from the analysis in the RNA-seq data of klf1-OFF and ON hearts at 7 dpt demonstrating enrichment scores of gene signatures such as Cell division (C), DNA replication (D), and Generation of precursor metabolites and energy (E). (F) Ultrastructure of mitochondria was analyzed with TEM in klf1-OFF and ON ventricular myocardium at 7 dpt, and cristae numbers were quantifed (mean±SEM, n=30-32). (G) Quantification of mitochondrial DNA content (mtDNA) of klf1-OFF and ON ventricles at 7 dpt using qPCR (mean±SEM, n=3). Expression of mtDNA (mt-co1, mt-nd1) was normalized to nuclear DNA (nDNA; actb2) expression and shown relative to the levels in klf1-OFF controls. (H-K) Quantification of NADH (H), $NAD^+$ (I), NADH/$NAD^+$ ratio (J), and ATP (K) in klf1-OFF and ON ventricles at 7 dpt (mean±SEM, n=3-4). (L) Expression values (in FPKM) of genes regulating mitochondrial biogenesis and function obtained from RNA-seq data of klf1-OFF and ON ventricles at 7 dpt (mean±SEM, n=4). (M-P) Mass spectrometry-based quantification of glucose 6-phosphate (M), ribose 5-phosphate (N), sedoheptulose 7-phosphate (O), and serine (P) in klf1-OFF and ON ventricles at 7 dpt (mean±SEM, n=5). Quantified value is shown relative to the levels in klf1-OFF controls. (Q-S) Quantification of NADPH (Q), $NADP^+$ (R), and NADPH/$NADP^+$ ratio (S) in klf1-OFF and ON ventricles at 7 dpt (mean±SEM, n=3). FDR, false discovery rate; FPKM, fragments per kilobase of exon per million mapped reads; GO, gene ontology; GSEA, gene set enrichment analysis; KEGG, Kyoto Encyclopedia of Genes and Genomes. *p<0.05, p<0.01, *p<0.005, and ****p<0.001 by unpaired t-test.

Figure 17:
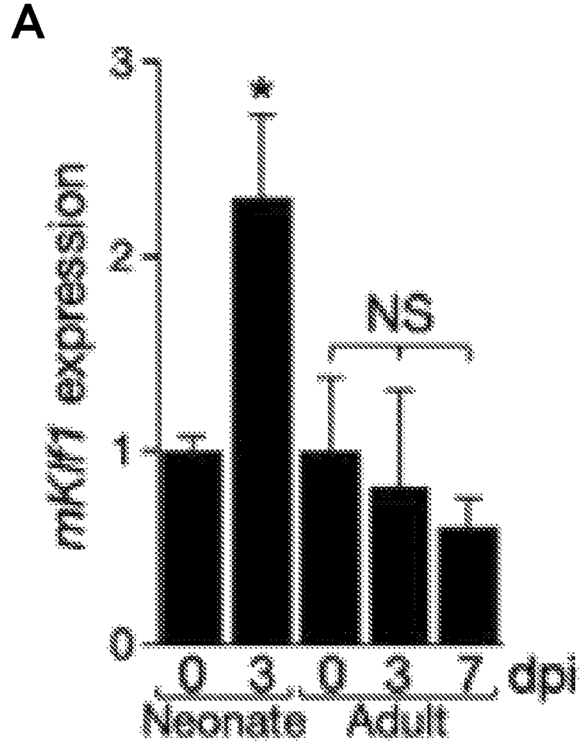
Figure 17:
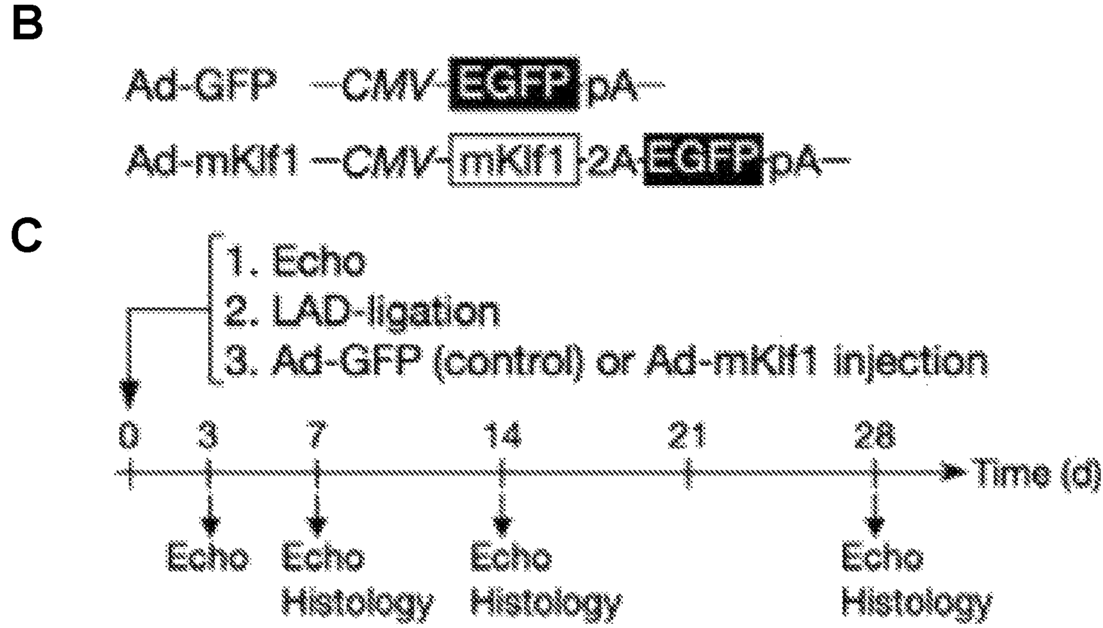
Figure 17:
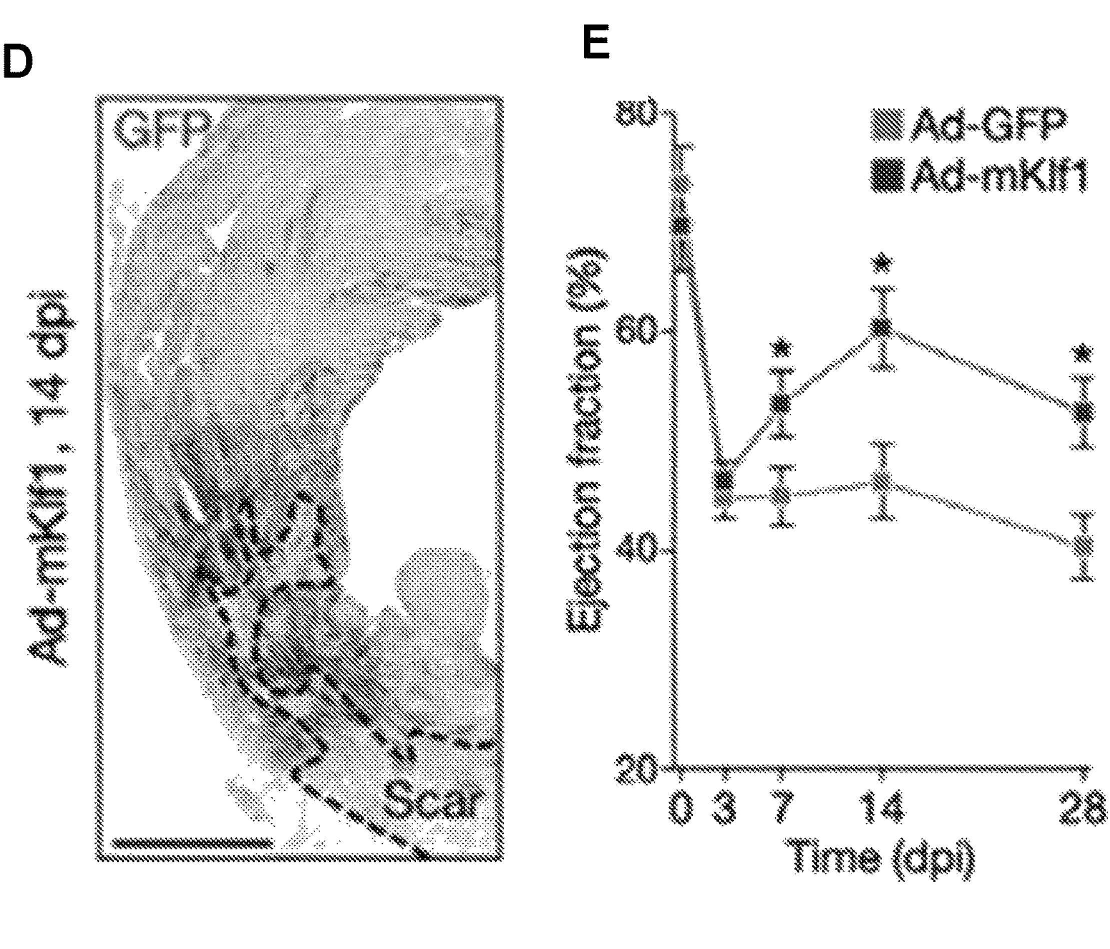
Figure 17:
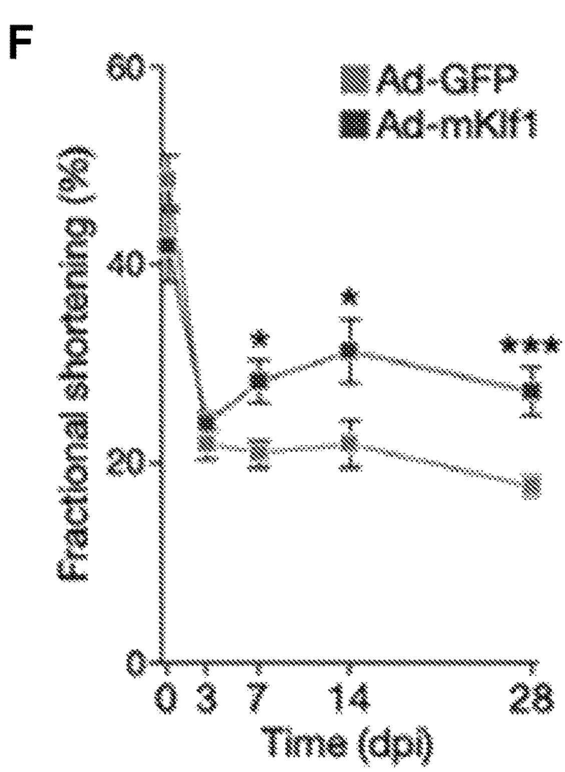
Figure 17:
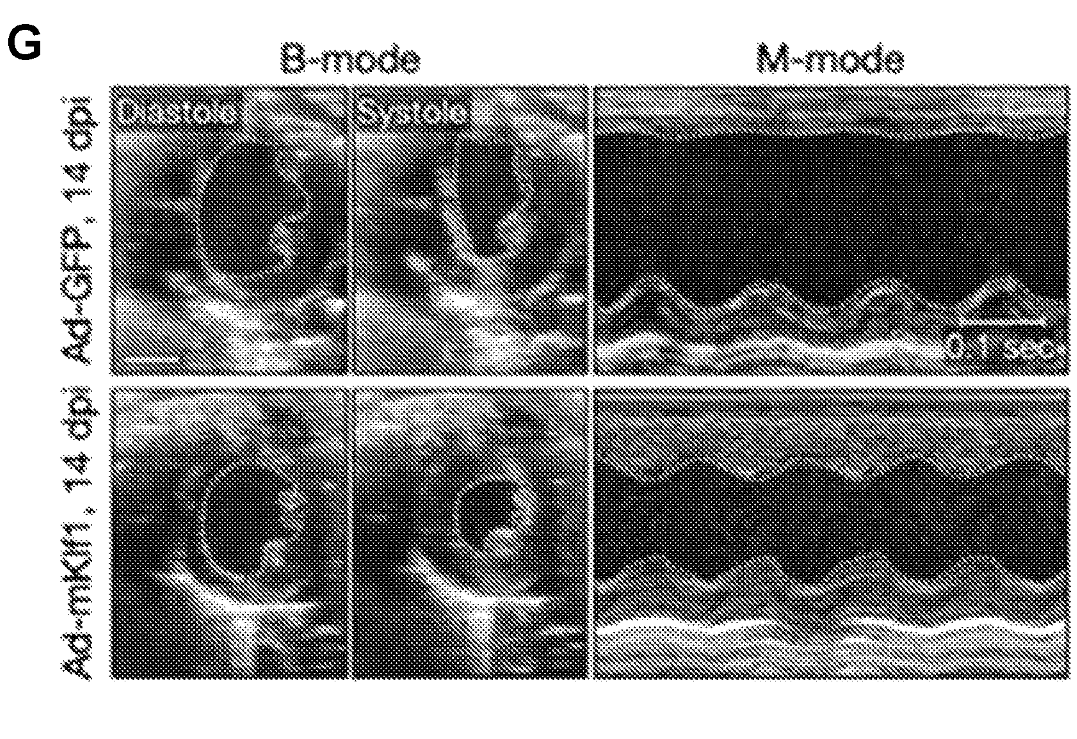
Figure 17:
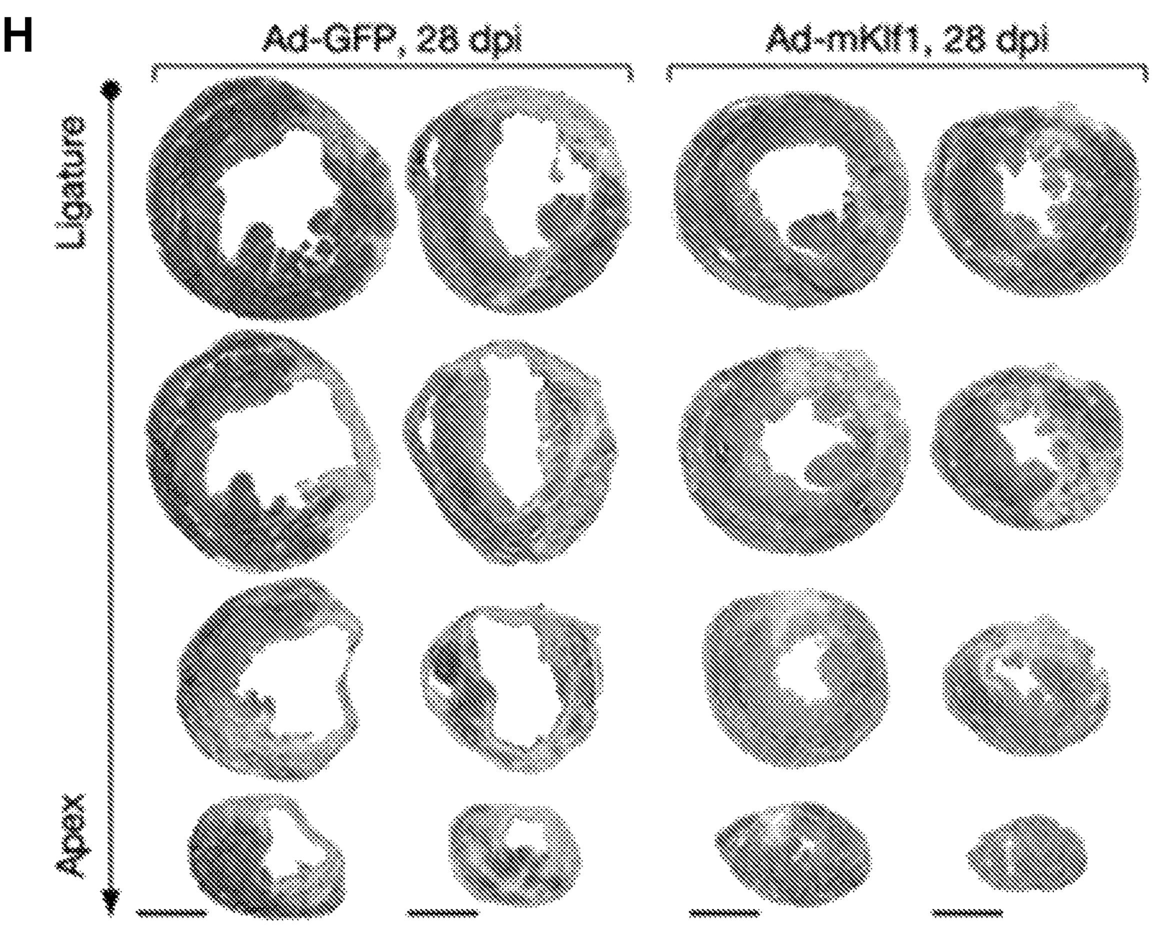
Figure 17:
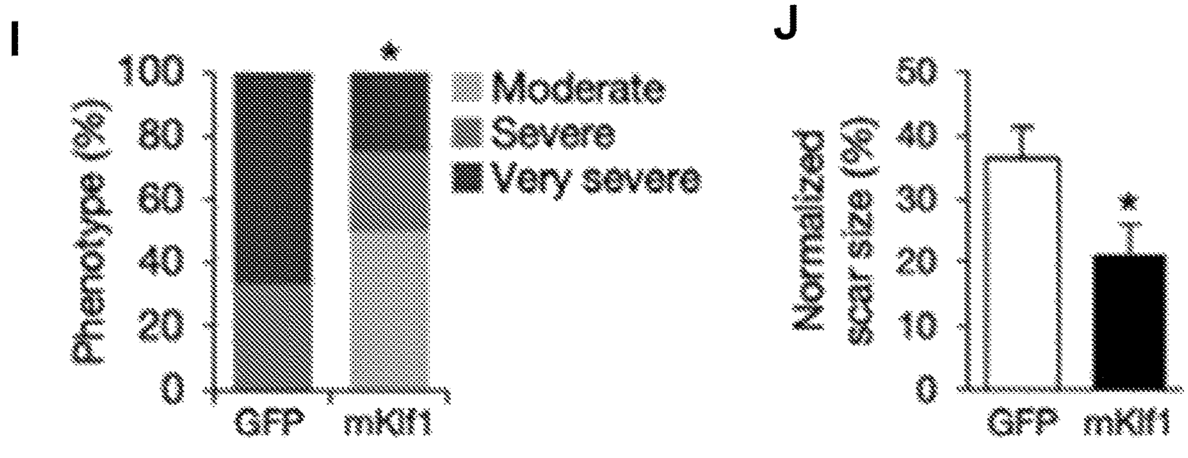
Figure 17:
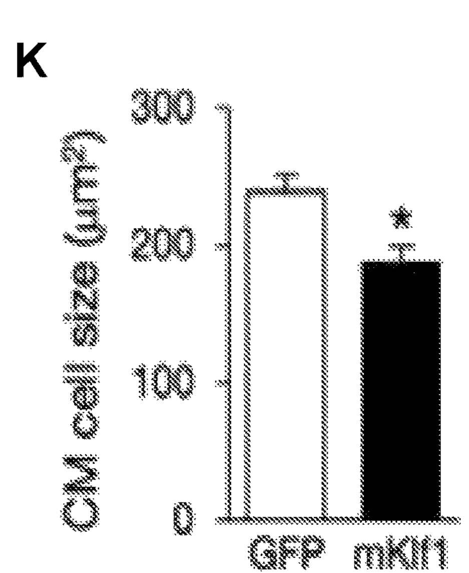
Figure 17:
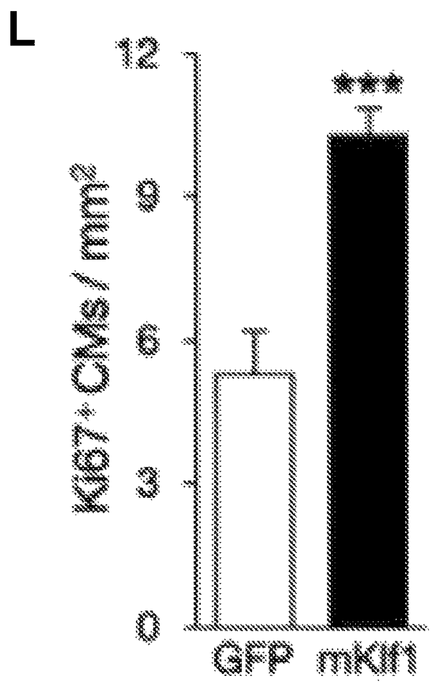
Figure 17:
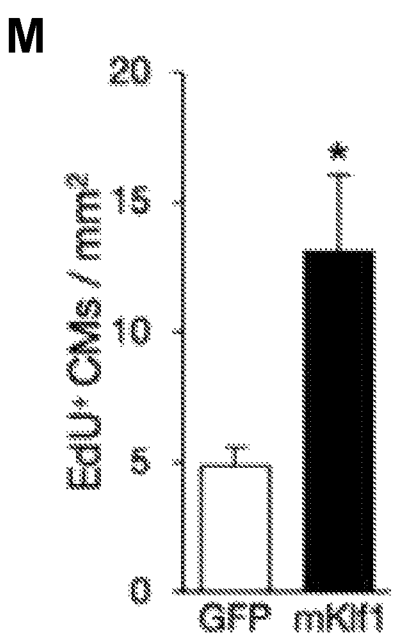
Figure 17:
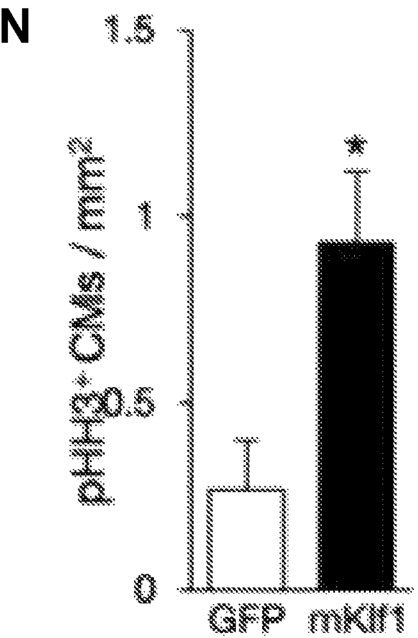

FIG. 17: Extensive analysis of Klf1 function in mouse hearts. (A) Time course qRT-PCR analysis of mouse Klf1 (mKlf1) expression in neonatal and adult mouse hearts after myocardial infarction (mean±SEM, n=3-4). Gene expression is shown relative to the levels in uninjured controls (0 dpi). MI was induced by permanent ligation of the left anterior descending (LAD) coronary artery in adult mice and neonatal mice at postnatal day 2. (B) Adenovirus vectors used in the study. (C) Experiments and analyses performed in the study. Echo, echocardiography. (D) Immunohistochemistry of enhanced green fluorescence protein (EGFP) reporter expression from Ad-mKlf1. Dotted line outlines the infarcted area. (E-G) Time course echocardiography of Ad-GFP (control) and Ad-mKlf1 injected hearts (mean±SEM, n=7-11). Ejection fraction (E) and fractional shortening (F), and representative B-mode and M-mode images (G) are shown. Baseline cardiac function was measured before MI and indicated as 0 dpi (E, F). (H) Gomori-trichrome staining of tissue sections from Ad-GFP-treated or Ad-mKlf1-treated hearts. Two independent hearts are shown for each treatment group. (I, J) Quantification of cardiac repair (I) and scar tissue sizes (J) in (H) (mean±SEM, n=8). (K) Immunofluorescence of TnT and WGA in the injury border zone myocardium in cross-sectional planes was performed and quantified (mean±SEM, n=5). (L-N) Quantification of $Ki67^+TnT^+$ cardiomyocytes (L; mean±SEM, n=5), $EdU^+TnT^+$ cardiomyocytes (M; mean±SEM, n=3-4), $pHH3^+TnT^+$ cardiomyocytes (N; mean±SEM, n=5) in Ad-GFP (control) and Ad-mKlf1 injected hearts. dpi, days post-injury; EdU, 5-ethynyl-2'-deoxyuridine; pHH3, phospho-histone H3; WGA, wheat germ agglutinin. *p<0.05, *** p<0.005 by unpaired t-test in all panels except (I) which was analyzed by $x^2$ test.

Figure 18:
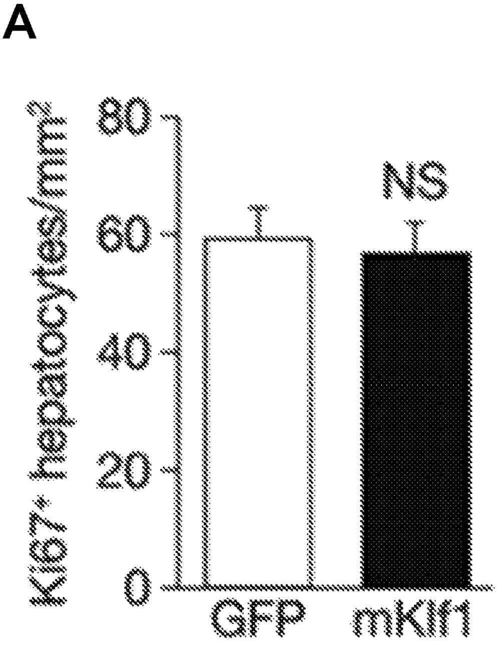
Figure 18:
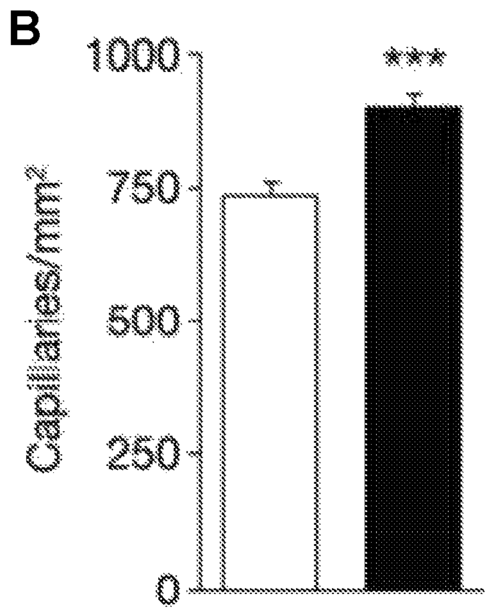

FIG. 18: Effects of mKlf1 overexpression on survival and in non-myocardial tissues in mice. (A) Immunofluorescence of Ki67 in liver tissue sections from mice injected intravenously with Ad-GFP or Ad-mKlf1 was performed and showed immunostaining of EGFP for the verification mKlf1 expression. $Ki67^+$ hepatocytes were visualized by autofluorescence and morphologically identified in the image and quantified (mean±SEM, n=10). (B) Immunofluorescence of CD31 in ventricular sections of post-MI mice injected with Ad-GFP and Ad-mKlf1 was performed and capillaries quantified (mean±SEM, n=5). Ad-GFP, adenovirus vector containing green fluorescent protein construct (control); Ad-mKlf1, adenovirus vector containing mKlf1 construct; ***p<0.005 by unpaired t-test (A, B).

Figure 19:
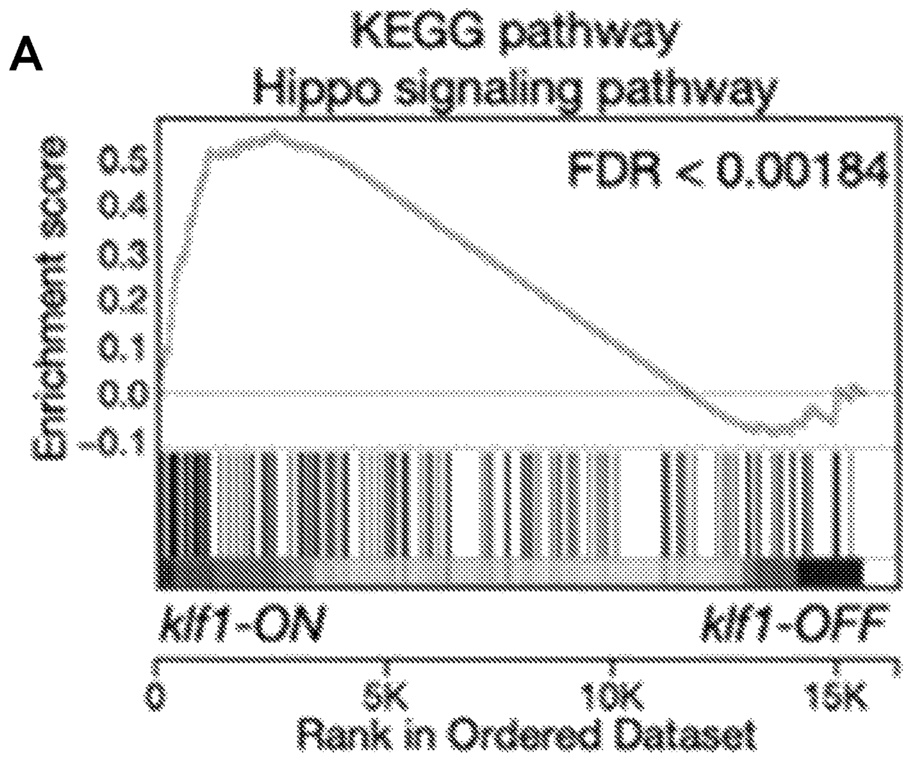
Figure 19:
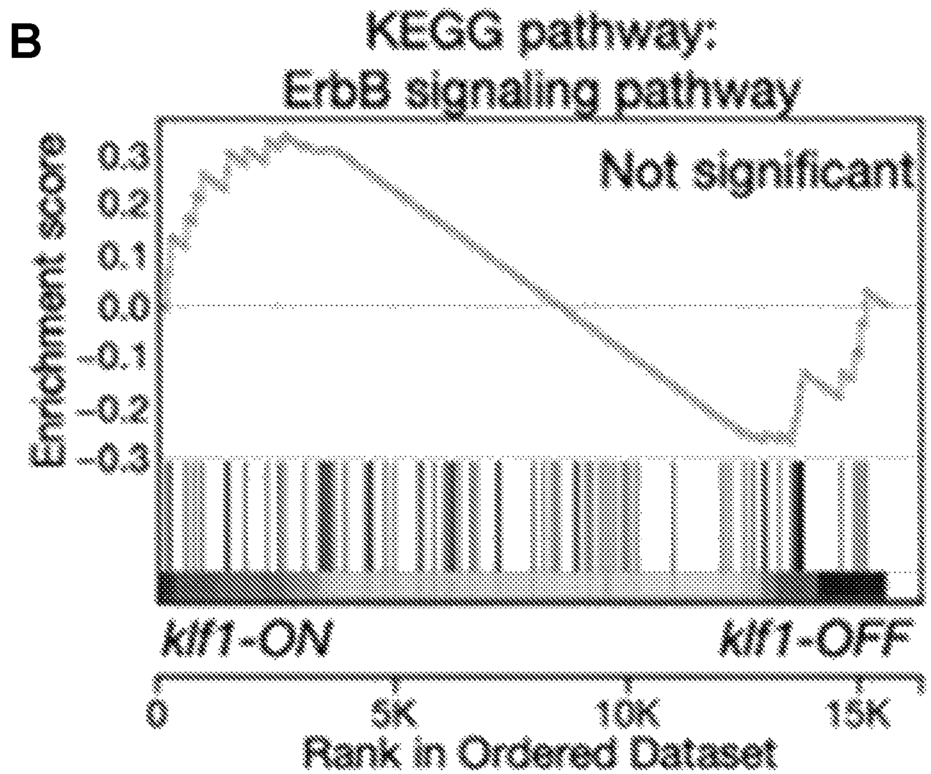
Figure 19:
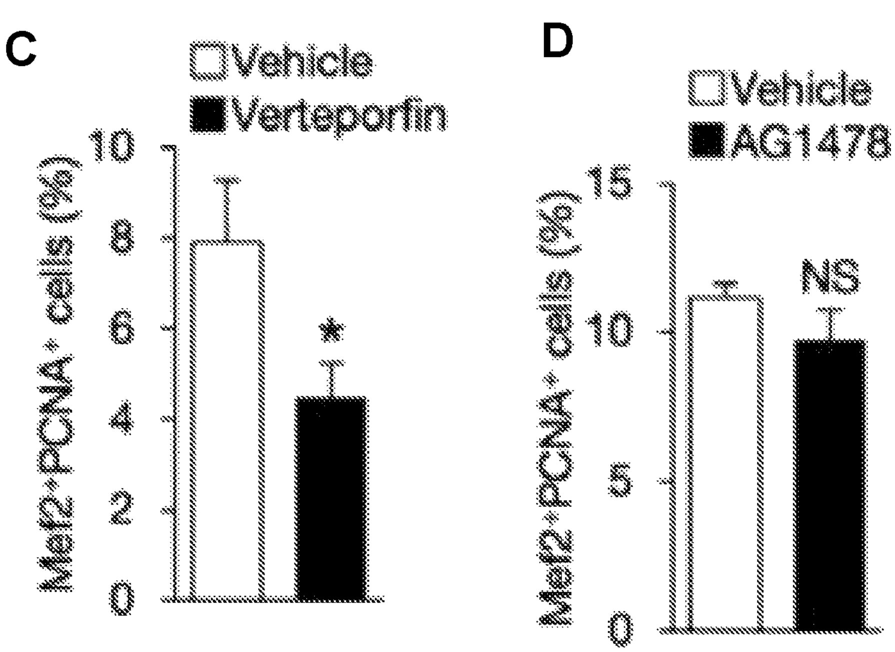

FIG. 19: Roles of Hippo and ErbB signaling pathways in Klf1-induced cardiomyogenesis. (A, B) GSEA plots demonstrating enrichment scores of the KEGG gene sets associated with Hippo signaling (A) and ErbB signaling (B) pathways in the RNA-seq data of klf1-OFF and ON hearts at 7 dpt. (C, D) Immunofluorescence of myocyte enhancer factor 2 (Mef2) and proliferating cell nuclear antigen (PCNA) in 7 dpt klf1-ON hearts with pharmacological inhibition of YAP or ErbB indicated proliferating cardiomyocytes co-labeled with Mef2 and PCNA. $Mef2^+PCNA^+$ cells were quantified in hearts with the inhibition of YAP (C; mean±SEM, n=4) or ErbB (D; mean±SEM, n=4). dpt, day post-treatment; FDR, false discovery rate; GSEA, gene set enrichment analysis; KEGG, Kyoto Encyclopedia of Genes and Genomes; YAP, yes-associated protein.

DESCRIPTION OF EMBODIMENTS

Many cardiac diseases involve the loss of cardiomyocytes which are not replaced because adult cardiomyocytes are terminally differentiated cells that have limited proliferative capacity. As demonstrated herein, administration of a KLF or a KLF nucleic acid is useful promote cardiomyogenesis. As demonstrated herein each of KLF1 and KLF2b are useful to promote cardiomyogenesis. This process involves dedifferentiation of adult cardiomyocytes which then proliferate and subsequently differentiate into cardiomyocytes. That is, the administration of at least one KLF is useful to promote or induce cardiomyogenesis in an adult heart.

In one embodiment KLF induced cardiomyogenesis occurs not by reprogramming the cell lineage but by reprogramming the status of adult cardiomyocytes into a proliferative state. This may be accompanied by the reprogrammed cardiomyocytes promoting growth in neighboring tissues.

In some embodiments the cardiomyogenesis includes expansion of epicardial cells and endothelial cells.

Methods

Increasing the levels or activity of a KLF, for example by administration of a at least one KLF nucleic acid to cardiac tissue is useful for promoting or inducing cardiomyogenesis in vitro or in vivo. Accordingly, methods are provided for promoting or inducing cardiomyogenesis comprising administering at least one KLF, or at least one KLF nucleic acid, or at least one expression vector comprising a KLF nucleic acid to a subject. In one embodiment the cardiomyogenesis is associated with cardiomyocyte dedifferentiation, for example dedifferentiation of adult cardiomyocytes.

Suitable subjects include individuals (e.g., mammalian subjects, such as humans; non-human primates; experimental non-human mammalian subjects such as mice, rats, etc.) having a cardiac condition. The cardiac condition can result in ischemic heart tissue, e.g., individuals with coronary artery disease; and the like. Suitable subjects include those that have heart failure, or a degenerative cardiac disease such as familial cardiomyopathy, dilated cardiomyopathy, hypertrophic cardiomyopathy, restrictive cardiomyopathy, or coronary artery disease with resultant ischemic cardiomyopathy.

The subject can be an infant, child, or adult.

In one embodiment the method comprises administering the KLF, KLF nucleic acid, or an expression vector comprising a KLF nucleic acid to a cardiomyocyte or cardiac tissue of a subject. Alternatively, or in addition, the method can involve inducing the expression of a KLF in a cardiomyocyte of the subject. The addition or expression of active KLF in the cardiomyocyte dedifferentiates the cardiomyocyte. The resulting cell (proliferative cardiomyocyte) can then proliferate to replace at least a portion of the cardiomyocytes lost due to for example, an ischemic event. After proliferation the dedifferentiated cells re-differentiate into functional cardiomyocytes.

In some embodiments a KLF, a KLF nucleic acid, or an expression vector comprising a KLF nucleic acid is administered to a cardiomyocyte or cardiac tissue. The administration to the cardiomyocyte and/or cardiac tissue can occur in vitro or in vivo. The KLF, KLF nucleic acid, or an expression vector comprising the KLF nucleic acid can be contacted with the cell directly, i.e. applied directly to a cell, or alternatively may be combined with the cell indirectly, e.g. by injecting the KLF, KLF nucleic acid, or expression vector into the bloodstream of a subject, which then carries the molecule to the cell. Alternatively or in addition the KLF, KLF nucleic acid, or an expression vector comprising the KLF nucleic acid can be administered directly to the heart, for example by injection into the myocardium.

In these methods, a therapeutically effective amount of KLF, KLF nucleic acid or expression vector is administered to the subject. In some embodiments, administration involves the delivery of the KLF, KLF nucleic acid or expression vector to cardiac tissue or directly to cardiomyocytes.

Administering the KLF, KLF nucleic acid or expression vector may be achieved by any method known in the art. In some embodiments contacting the cell and the KLF or KLF nucleic acid occurs in vitro or in vivo. The KLF or KLF nucleic acid may be contacted with the cell directly, i.e. applied directly to a cardiomyocyte, or alternatively may be combined with the cell indirectly, e.g. by injecting the KLF1 or KLF1 nucleic acid into the cardiac tissue of a subject.

In some embodiments administering KLF, KLF nucleic acid or expression vector increases the level of KLF in a cardiomyocyte or cardiac tissue compared to the endogenous KLF level. The term 'endogenous' as used in this context refers to the 'naturally-occurring' levels of expression and/or activity of KLF prior to administration of KLF, KLF nucleic acid or expression vector.

Cardiomyogenesis

Cardiomyogenesis is a complex process in which the cardiomyocytes (CMs) that form the muscular tissue of the heart (the myocardium) divide and make new cells. As disclosed herein KLF-induced cardiomyogenesis is mediated through CM reprogramming and expansion (proliferation) of those cells followed by re-differentiation to mature, contractile CMs.

The KLF induces dedifferentiation of the cardiomyocyte to produce proliferative cardiomyocytes. That is cardiomyocytes are terminal differentiated cells that in normal adult individuals are incapable of differentiating to form other cell types or regenerate. It is generally accepted that after birth cardiomyocytes undergo terminal differentiation, characterized by binucleation and centrosome disassembly, rendering the heart unable to regenerate. However, as demonstrated herein KLF administration induces CMs to dedifferentiate into proliferative CMs. In some embodiments the proliferative CMs are mitotic.

In some embodiments the methods involve allowing the proliferative cardiomyocytes to proliferate in the presence of the KLF. This may occur in vitro under appropriate cell or tissue culture conditions or may occur in vivo. The result of the proliferation is that each CM produces a population of proliferative cardiomyocytes.

Once the KLF is removed, or once the KLF is metabolized otherwise degrades the population of proliferative cardiomyocytes spontaneously differentiates to produce a population of cardiomyocytes. In this way KLF can be used to increase the number of cardiomyocytes in vitro or in vivo In some embodiments the KLF induces chromatin remodeling to facilitate the dedifferentiation.

In one embodiment CMs expressing KLF have a paracrine effect. For example, as exemplified herein expression of KLF increases the number of epicardial cells and vascular endothelial cells.

In an embodiment expression of a KLF in CMs under the control of a myosin heavy chain (MHC) promoter does not lead to the expression of a marker for epicardial and endothelial cells, Raldh2 (retinaldehyde dehydrogenase 2; also known as Aldh1a2). Accordingly, expression of a KLF in CMs does not change the cell lineage. The cell lineage also does not change even after proliferation for 1, 2, 3, 4, 5, 6, 7, 8, 9, 10, 11 or 12 days. In some embodiments expression of KLF by the MHC promoter is at a reduced level in comparison to a normal CM.

That is KLF induced cardiomyogenesis in adult hearts does not involve reprogramming the cell lineage. Rather, KLF induced cardiomyogenesis is characterized by reprogramming the status of adult CMs into an extremely proliferative state, together with a capacity for promoting growth in neighboring tissues.

In some embodiments KLF induced cardiomyogenesis is characterized by a switch form energy production from oxidative phosphorylation (OXPHOS) to pentose phosphate pathway (PPP) and/or serine synthesis pathway (SPP).

KLF1

As used herein, 'Krüppel-like factor' or 'KLF' refers to any protein variant of KLF1 or KLF2b from any species (e.g., mouse, human, non-human primate), as well as any mutants and fragments thereof that retain a KLF activity. Similarly, a "KLF nucleic acid" refers to any nucleic acid sequence encoding a KLF, e.g., from any species, e.g., mouse, human, or non-human primate. The human KLF1 amino acid sequence is shown in SEQ ID NO: 1, the nucleotide sequence of human KLF1 is shown underlined in SEQ ID NO: 2 and the coding sequence in SEQ ID NO: 3. The nucleotide sequence of mouse KLF1 is shown in SEQ ID NO: 4, and the coding sequence is in shown in SEQ ID NO: 5. KLF1 is also known as Erythroid Krüppel-like transcription factor (EKLF), Krüppel-like factor 1, INLU, or HBFQTL6. The zebrafish KLF2b amino acid sequence is shown in SEQ ID NO: 6, the nucleotide sequence of zebrafish KLF2b is shown in SEQ ID NO: 7 and the coding sequence in in SEQ ID NO: 8. Also the zebrafish KLF1 amino acid sequence is shown in SEQ ID NO: 11, the nucleotide sequence of zebrafish KLF1 is shown in SEQ ID NO: 9 and the coding sequence in in SEQ ID NO: 10.

In some embodiments the KLF may be from a non-human or non-mammalian species. For example, the KLF may be from zebrafish or from a regenerative species such as a salamander or snake.

As described herein, KLF or nucleic acids encoding KLF (KLF nucleic acid) can be used to induce cardiomyogenesis in vitro or in vivo. Thus, the KLF and KLF nucleic acids can be used to treat conditions in which cardiomyocyte dedifferentiation, proliferation or both would be desirable, such as ischemic injury, for example after myocardial infarction (MI); after cardiac injury caused for example by cardiotoxic drugs (e.g., anthracycline antibiotics such as doxorubicin), cocaine, methamphetamine, cyclic antidepressants, calcium channel blockers, beta-blockers, and digoxin) or trauma (whether accidental or intentional as a result of surgery); heart failure; or diminished cardiac capacity associated with aging.

The methods disclosed herein can be used for cardiac regeneration. In this context, ‘cardiac regeneration’ refers to the structural and/or functional regeneration or improvement of a damaged heart. For example a structural improvement may be an increase in the amount or number of cardiomyocytes in a heart after administration of KLF. An example of a functional improvement is an increase in contractility or ejection fraction of a heart after administration of KLF.

For example the ejection fraction, fractional shortening, or both may be increased by 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, or more compared to the ejection fraction or fractional shortening before administration of the FLK.

In some embodiments the cardiac regeneration occurs by 2, 3, 4, 5, 6, 7, 8, 9, 10, 11, 12, 13, 14, 15, 16, 17, 18, 19, 20, 21, 22, 23, 24, 25, 26, 27, 28 days after administration of the KLF.

The methods disclosed herein can utilize a KLF variant or KLF functional fragment. A variant or functional fragment is capable of binding DNA with the same specificity as wild-type KLF and retains at least one function of wild-type KLF. For example, in one embodiment a variant or functional fragment is any variant of KLF that retains DNA binding activity.

In some embodiments the KLF may be a conjugate or a fusion protein. For example, a KLF fusion protein. A fusion protein comprises at least a portion of a KLF joined via a peptide bond to at least a portion of another protein, peptide or polypeptide, e.g. a nuclear localization sequence or an additional KLF or domain thereof, for example a transactivation domain. In some embodiments the KLF may be fused to a transactivation domain from another protein, for example the transactivator domain p53 or VP16. Fusion proteins can also comprise a marker protein (e.g. a fluorescent protein such as GFP), or a protein that aids in the isolation and/or purification (e.g., a FLAG or His tag). The non-KLF sequences can be amino- or carboxy-terminal to the KLF sequences.

In some embodiments the KLF is fused with one or more nuclear localization sequences.

In some embodiments the KLF nucleic acid encodes the KLF fusion protein.

In some embodiments the methods require administering KLF comprising the mature KLF amino acid sequence. Alternatively, a KLF may be at least 80% identical to a mature KLF amino acid sequence. In general, the KLF useful in the methods described herein are at least 80% identical to the wildtype KLF amino acid sequences, e.g. 80, 81, 82, 83, 84, 85, 86, 87, 88, 89, 90, 91, 92, 93, 94, 95, 96, 97, 98, or 99% sequence identity to the wildtype amino acid sequence. Useful KFL proteins can be identified through routine experimentation. In general, the KLF protein functions as wildtype KLF.

The methods can include administering a KLF nucleic acid comprising a mature KLF coding sequence. Alternatively, a KLF nucleic acid may be at least 80% identical to a mature KLF coding sequence. In general, the KLF nucleic acids useful in the methods described herein are at least 80% identical to the wildtype KLF nucleic acid, e.g. 80, 81, 82, 83, 84, 85, 86, 87, 88, 89, 90, 91, 92, 93, 94, 95, 96, 97, 98, or 99% sequence identity to the wildtype nucleic acid. Useful nucleic acids can be identified through routine experimentation. In general, the nucleic acids must encode a protein that functions as wildtype KLF.

In some embodiments, the KLF nucleic acid can be an ssRNA, dsRNA, dsDNA, or an expression vector, e.g., a viral expression vector of a plasmid expression vector comprising a KLF nucleic acid. The KLF nucleic acid may include one or more modifications.

In some embodiments, the KLF nucleic acid comprises at least one nucleotide modified at the 2' position of the sugar, for example a 2'-O-alkyl, 2'-O-alkyl-O-alkyl or 2'-fluoro-modified nucleotide. In other embodiments, RNA modifications include 2'-fluoro, 2'-amino and 2' O-methyl modifications on the ribose of pyrimidines, a basic residue or an inverted base at the 3' end of the RNA.

A number of nucleotide and nucleoside modifications make the nucleic acid into which they are incorporated more resistant to nuclease digestion. Specific examples of modified KLF nucleic acids include those comprising modified backbones, for example, phosphorothioates, phosphotriesters, methyl phosphonates, short chain alkyl or cycloalkyl intersugar linkages or short chain heteroatomic or heterocyclic intersugar linkages. In some embodiments the modifications of the KLF nucleic acid are a phosphorothioate backbone or a heteroatom backbone, particularly $CH_2$—NH—O—$CH_2$, CH, —N($CH_3$)—O—$CH_2$ (known as a methylene(methylimino) or MMI backbone), $CH_2$—O—N($CH_3$)—$CH_2$, $CH_2$—N($CH_3$)—N($CH_3$)—$CH_2$ or O—N($CH_3$)—$CH_2$—$CH_2$ backbones, wherein the native phosphodiester backbone is represented as O—P—O—CH); amide backbones; morpholino backbone structures; peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, or boranophosphates Modified nucleic acid backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

One or more substituted sugar moieties can also be included, e.g., one of the following at the 2' position: OH, SH, $SCH_3$, F, OCN, $OCH_3OCH_3$, $OCH_3O(CH_2)n\ CH_3$, $O(CH_2)n\ NH_2$ or $O(CH_2)n\ CH_3$ where n is from 1 to about 10; C1 to C10 lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2$; $CH_3$; $ONO_2$; $NO_2$; $N_3$; $NH_2$; heterocycloalkyl; heterocycloalkaryl; aminoalkylamino; polyalkylamino; substituted silyl; a group for improving the pharmacokinetic properties of the nucleic acid; or a group for improving the pharmacodynamic properties of the nucleic acid and other substituents having similar properties. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA).

As another example, the KLF nucleic acid sequence can include at least one 2'-O-methyl-modified nucleotide, and in some embodiments, all of the nucleotides include a 2'-O-methyl modification. In another embodiment the modification is a 2'-methoxyethoxy[2'-O—$CH_2CH_2OCH_3$, also known as 2'-O-(2-methoxyethyl)]. Other modifications include 2'-methoxy (2'-O—$CH_3$), 2'-propoxy (2'-$OCH_2CH_2CH_3$) or 2'-fluoro (2'-F). Similar modifications may also be made at other positions on the nucleic acid, particularly the 3' position of the sugar on the 3' terminal nucleotide and the 5' position of 5' terminal nucleotide. The nucleic acids may also have sugar mimetics such as cyclobutyls in place of the pentofuranosyl group.

The KLF nucleic acid can also include, additionally or alternatively, base modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC or gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine or 2,6-diaminopurine. Inosine, can also be included. Other modifications include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl or other 8-substituted adenines and guanines, 5-halo particularly 5-bromo, 5-trifluoromethyl or other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

It is not necessary for all positions in a given nucleic acid to be uniformly modified, and more than one of the aforementioned modifications may be incorporated in a single oligonucleotide or even at within a single nucleoside within an oligonucleotide.

In some embodiments, the nucleic acids are chemically linked to one or more moieties or conjugates that enhance the activity, cellular distribution, or cellular uptake of the oligonucleotide. Such moieties comprise but are not limited to, lipid moieties such as a cholesterol moiety, a thioether, e.g., hexyl-S-tritylthiol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-t oxycholesterol moiety.

In some embodiments the KLF nucleic acid is operatively coupled to a promoter sequence. The promote sequence may be constitutively active or may be compositionally active. In some embodiments the promoter sequence is cardiac specific, for example the cardiac specific promoter sequence may be an alpha-myosin heavy chain (α-MHC) promoter, a myosin light chain 2 (MLC-2) promoter, a cardiac troponin C (cTnC) promoter, a NCX1 promoter, or a TNNT2 promoter.

In some embodiments the KLF nucleic acid is operatively coupled to an inducible promoter, for example a tetracycline inducible promoter, steroid hormone (e.g. progesterone or ecdysone) inducible promoter, or a hypoxia responsive promoter.

In other embodiments the KLF nucleic acid is operatively coupled to a promoter that is active or selectively active in a region of the heart adjacent to a damaged area. Such promoters include, for example, the GATA-4 promoter.

In other embodiments the KLF nucleic acid is operatively coupled to a promoter of a gene that is overexpressed in cardiac tissue in response to stress that results from ischemia and reperfusion. These genes include aminoadipate-semialdehyde synthase, apolipoprotein E, flavin containing monooxygenase 2, NADPH oxidase 4, prostaglandin-endoperoxide synthase 2, recombination activating gene 2, stearoyl-coenzyme A desaturase 1, or solute carrier family 38 (member 1).

Administration of KLF

In the methods described herein a KLF or KLF nucleic acid is administered to a subject. In particular the KLF or KLF nucleic acid is administered to a target cell, tissue or organ. In some embodiments, a KLF or KLF nucleic acid is administered to a target cell, tissue or organ or an expression vector encoding the KLF nucleic acid is administered to a target cell, tissue or organ where the KLF nucleic acid is expressed. In some embodiments, administered is systemic and the expression vector is taken up into target cells, tissues or organs. In some embodiments the expression vector may be taken up by non-target cells, tissues or organs, but preferably does not have a significant negative effect on such cells or tissues, or on the subject as a whole.

Methods for administered or delivery of nucleic acids and expression constructs to target cells are known in the art and include the methods described briefly below. Target cells can be, for example, cardiomyocytes. In some embodiments, the KLF, KLF nucleic acid or expression vector is delivered to the target cell, tissue or organ in vivo. In some embodiments, the KLF, KLF nucleic acid or expression vector is administered to the target cell ex vivo. In some embodiments, the KLF, KLF nucleic acid or expression vector is delivered to the target cell in vitro.

In some embodiments, the target cell is a cardiomyocyte. The cardiomyocyte may be present in a subject or may be in culture outside of the subject. In some embodiments, the KLF, KLF nucleic acid or expression vector is administered to the heart or cardiac tissue.

In other embodiments the target cell is a proliferative cardiomyocyte. That is, the KLF, KLF nucleic acid or expression vector can be administered to a cardiomyocyte that has already undergone KLF-induced dedifferentiation.

In some embodiments the KLF nucleic acid or expression vector may be transfected or transduced ex vivo into a cell of a subject. The transfected or transduced cells, capable of expressing KLF can then be expanded and administered to a subject. In some embodiments the cells are autologous to the subject. Suitable cells include those isolated from blood or bone marrow such as adult hematopoietic stem/progenitor cells.

In some embodiments the KLF, KLF nucleic acid or expression vector delivered systemically, such as by intravenous injection. Additional routes of administration may include, for example, oral, topical, intracardiac, and intramuscular. In some embodiments, KLF, KLF nucleic acid or expression vectors can be delivered ex vivo to cells harvested from a subject and then cells containing the KLF, KLF nucleic acid or expression vector are reintroduced to the subject.

In some embodiments the KLF, KLF nucleic acid or expression vector are administered via cardiac catheterization.

A number of methods are known in the art for delivery of nucleic acids (such as the KLF nucleic acids). These include adeno-associated viruses (AAV)- or lentiviral-mediated delivery, nano-particle mediated delivery, gel foam-mediated intrapericardial delivery; and direct intramuscular administration of nucleic acids into the heart.

A preferred method to administer a KLF nucleic acid is by the use of an adeno-associated virus (AAV). In some embodiments the KLF nucleic acids may be continually or conditionally expressed. Additionally, the use of cardiotropic AAV serotypes or mutants improves tissue specificity. Thus, for example, the methods include delivering the KLF nucleic acid in a cardiotropic AAV. Suitable AAV include cardiac specific AAV such as those described in Pacak and Byrne, Mol Ther, 2011, 19(9), pp 1582-1590.

Other viruses may also be used, for example a retrovirus, lentivirus, HSV or an adenovirus.

The use of cardiac tissue-specific promoters (e.g., NCX1, TNNT2) for expression allows for further specificity in addition to the AAV serotype.

In some embodiments, the KLF, KLF nucleic acid or expression vector is administered by transfection using a transfection agent or delivery vehicle. As used herein, the term “delivery vehicle” refers to a compound or compounds that enhance the entry of the KLF nucleic acid into cells. Examples of delivery vehicles include protein and polymer complexes (polyplexes), combinations of polymers and lipids (lipopolyplexes), multilayered and recharged particles, lipids and liposomes (lipoplexes, for example, cationic liposomes and lipids), polyamines, calcium phosphate precipitates, polycations, histone proteins, polyethylenimine, polylysine, and polyampholyte complexes. In some embodiments, the delivery vehicle comprises a transfection agent. Transfection agents may be used to condense nucleic acids. Transfection agents may also be used to associate functional groups with a polynucleotide. Non-limiting examples of functional groups include cell targeting moieties, cell receptor ligands, nuclear localization signals, compounds that enhance release of contents from endosomes or other intracellular vesicles (such as membrane active compounds), and other compounds that alter the behavior or interactions of the compound or complex to which they are attached (interaction modifiers). For delivery in vivo, complexes made with sub-neutralizing amounts of cationic transfection agent can be used.

In some embodiments, the KLF nucleic acid or expression vector can be delivered using an exosome or exosome-like vesicle. For example, the KLF nucleic acid may be introduced into an exosome-producing cell and exosomes containing the KLF nucleic acid may be isolated from those cells. Alternatively, exosomes may be isolated or prepared according to any method known in the art and the KLF nucleic acid introduced into the exosomes.

In some embodiments, the KLF nucleic acid or expression vector can be delivered using a lipopolymer, liposomes, gelatin complex, poloxamine nanosphere, or a lipoprotein.

An alternate technique to achieve cardiac specific delivery of the KLF nucleic acid or expression vector is ultrasound targeted microbubble destruction (UTMD). This technique is based upon physical properties of ultrasound contrast agents which are gas filled microbubbles that oscillate to destruction when sonified by ultrasound. The Microbubbles can be loaded with KLF nucleic acid or expression vector, infused intravenously and destroyed in the heart by ultrasound, thus transfecting the heart.

In some embodiments, the KLF nucleic acid or expression vector can be delivered systemically. In some embodiments, the KLF nucleic acid or expression vector can be delivered in combination with one or more pharmaceutically acceptable carriers. Polymer reagents for delivery of the KLF nucleic acid or expression vector may incorporate compounds that increase their utility. These groups can be incorporated into monomers prior to polymer formation or attached to polymers after their formation. A vector transfer enhancing moiety is a molecule that modifies a nucleic acid complex and can direct it to a cell location (such as tissue cells) or location in a cell (such as the nucleus) either in culture or in a whole organism. By modifying the cellular or tissue location of the complex, the desired localization and activity of the KLF nucleic acid or expression vector can be enhanced. The transfer enhancing moiety can be, for example, a protein, a peptide, a lipid, a steroid, a sugar, a carbohydrate, a nucleic acid, a cell receptor ligand, or a synthetic compound. The transfer enhancing moieties can, in some embodiments, enhance cellular binding to receptors, cytoplasmic transport to the nucleus and nuclear entry or release from endosomes or other intracellular vesicles.

Nuclear localizing signals (NLSs) can also be used to enhance the targeting of the mir-1 nucleic acid or expression vector into proximity of the nucleus and/or its entry into the nucleus. Such nuclear transport signals can be a protein or a peptide such as the SV40 large Tag NLS or the nucleoplasmin NLS. These nuclear localizing signals interact with a variety of nuclear transport factors, such as the NLS receptor (karyopherin alpha), which then interacts with karyopherin beta. The nuclear transport proteins themselves can also, in some embodiments, function as NLS since they are targeted to the nuclear pore and nucleus.

Those skilled in the art will be able to select and use an appropriate system for delivering the KLF nucleic acid or expression vector to the heart or cardiac tissues or to cardiomyocytes or other target cells in vitro, ex vivo, or in vivo without undue experimentation.

In some embodiments, local delivery of KLF nucleic acid or expression vector is desirable. In particular, delivery of the KLF nucleic acid or expression vector to the heart is desirable.

There are a number of strategies to enable localized delivery of KLF, KLF nucleic acid or expression vector to the heart. For example, osmotic mini-pumps, such as the Alzet® osmotic pump, can be used for effective local delivery of the KLF, KLF nucleic acid or expression vector at a sustainable therapeutic concentration. The pumps with their reservoirs are commonly implanted into subcutaneous tissue, and deliver the KLF, KLF nucleic acid or expression vector to the target tissue via silicone tubes or cannulae. Osmotic mini-pumps depend on osmotic pressure for steady-state drug delivery and have already been applied clinically.

Localized delivery of KLF, KLF nucleic acids or expression vectors may be achieved by grafting of cells. In addition to cell replacement therapy, cells containing a KLF, KLF nucleic acid or expression vector may also be grafted to the cardiac muscle.

KLF Dosage

The effective dose level of the administered KLF, KLF nucleic acid, or expression vector will depend upon a variety of factors including: the type of condition being treated and the stage of the condition; the activity and nature of the KLF, KLF nucleic acid, or expression vector employed; the composition employed; the age, body weight, general health, sex and diet of the subject; the time of administration; the route of administration; the duration of the treatment; drugs used in combination or coincidental with the treatment, together with other related factors well known in medicine.

A skilled person would be able, by routine experimentation, to determine an effective, non-toxic dosage that would be required to treat applicable conditions. These will most often be determined on a case-by-case basis.

Generally, an effective dosage is expected to be in the range of about 0.0001 mg to about 1000 mg per kg body weight per 24 hours; typically, about 0.001 mg to about 750 mg-per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; or about 1.0 mg to about 250 mg per kg body weight per 24 hours. More typically, an effective dose range is expected to be in the range of about 10 mg to about 200 mg 20 per kg body weight per 24 hours.

Alternatively, an effective dosage may be up to about 5000 mg/m2. Generally, an effective dosage is expected to be in the range of about 10 to about 5000 mg/m2, typically about 10 to about 2500 mg/m2, about 25 to about 2000 mg/m2, about 50 to about 1500 mg/m2, about 50 to about 1000 mg/m2, or about 75 to about 600 mg/m2.

Further, it will be apparent to one of ordinary skill in the art that the optimal quantity and spacing of individual dosages will be determined by the nature and extent of the condition being-treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per day for a defined number of days, can be ascertained by those skilled in the art using conventional course of treatment determination tests.

The efficacy of a treatment may also be evaluated by determining the level of expression of KLF in the sample from a subject treated with KLF, KLF nucleic acid or an expression vector. After a period of time the level of expression of a KLF nucleic acid in a further sample from the subject is determined and a change in the level of KLF nucleic acid expression may be indicative of the efficacy of the treatment regime. The sample may comprise blood plasma or blood serum.

Alternatively or in addition the efficacy of a treatment can be evaluated by determining the level of proliferative cardiomyocytes, for example in a sample from a subject treated with KLF, KLF nucleic acid or an expression vector.

Cardiomyocyte Population/Cardiac Progenitor Cell Population

The administration of KLF, a KLF nucleic acid or expression vector generates a population of proliferative cardiomyocytes. The proliferative cardiomyocytes can be a population of immature cardiomyocytes, cardiomyocytes with embryonic phenotype, or cardiac progenitor cell population, or any combination thereof. This population of proliferative cardiomyocytes can be incorporated into a pharmaceutical composition for administration to the subject. In some embodiments the population of proliferative cardiomyocytes can be allowed to differentiate into cardiomyocytes before incorporation into a pharmaceutical composition.

KLF, a KLF nucleic acid or expression vector can be administered to adult cardiomyocytes taken from a subject (or elsewhere) in order to induce cardiomyogenesis. The resultant cells, whether they be a population of cardiomyocytes or a population of proliferative cardiac progenitor cells can be prepared as a pharmaceutical composition, for example a sterile aqueous or non-aqueous solution, suspension or emulsion, which additionally comprises a physiologically acceptable carrier (i.e., a non-toxic material that does not interfere with the activity of the cardiomyocytes). Any suitable carrier known to those of ordinary skill in the art may be used in the pharmaceutical composition. The selection of a carrier will depend, in part, on the nature of the substance (i.e., cells or chemical compounds) being administered.

Suitable carriers include physiological saline solutions, gelatin, water, alcohols, natural or synthetic oils, saccharide solutions, glycols, injectable organic esters such as ethyl oleate or a combination of such materials. A pharmaceutical composition may additionally contain preservatives and/or other additives such as, for example, antimicrobial agents, anti-oxidants, chelating agents and/or inert gases, and/or other active ingredients. In some embodiments, a cardiomyocyte population or cardiac progenitor population is encapsulated, according to known encapsulation technologies.

In some embodiments, a cardiomyocyte population or cardiac progenitor population is present in a matrix.

A unit dosage form of a cardiomyocyte population or cardiac progenitor population can contain from about $10^3$ cells to about $10^9$ cells, e.g., from about $10^3$ cells to about $10^4$ cells, from about $10^4$ cells to about $10^5$ cells, from about $10^5$ cells to about $10^6$ cells, from about $10^6$ cells to about $10^7$ cells, from about $10^7$ cells to about $10^8$ cells, or from about $10^8$ cells to about $10^9$ cells.

In some embodiments, there is provided a method of inducing cardiomyogenesis in a population of cardiomyocytes in vitro and implanting the population of cardiomyocytes into the heart of a subject. The population of cardiomyocytes can be used for allogenic or autologous transplantation into an individual in need thereof.

Combination Therapy

The terms 'combination therapy' or 'adjunct therapy' in defining use of KLF, KLF nucleic acid, or vector together with one or more other pharmaceutical agents, are intended to embrace administration of each agent in a sequential manner in a regimen that will provide beneficial effects of the drug combination, and is intended to embrace co-administration of these agents in a substantially simultaneous manner, such as in a single formulation having a fixed ratio of these active agents, or in multiple, separate formulations of each agent.

In accordance with various embodiments of the present invention one or more of KLF, KLF nucleic acid, or vector may be formulated or administered in combination with one or more additional therapeutic agents. Thus, in accordance with various embodiments of the present invention, at least one of KLF, KLF nucleic acid, or vector may be included in combination treatment regimens with surgery and/or other known treatments or therapeutic agents, and/or adjuvant or prophylactic agents.

A number of agents are available in commercial use, in clinical evaluation and in pre-clinical development, which could be selected for treatment of the diseases and conditions listed above as part of combination drug therapy. Suitable agents which may be used in combination therapy will be recognized by those of skill in the art. Suitable agents are listed, for example, in the Merck Index, An Encyclopedia of Chemicals, Drugs and Biologicals, 12th Ed., 1996, and subsequent editions, the entire contents of which are incorporated herein by reference.

Combination regimens may involve the active agents being administered together, sequentially, or spaced apart as appropriate in each case. Combinations of active agents including at least one of the KLF, KLF nucleic acid, or vector may be synergistic.

The co-administration of at least one of the KLF, KLF nucleic acid, or vector with an additional agent may be effected by the agents being in the same unit dose as another active agent, or one or more other active agent(s) may be present in individual and discrete unit doses administered at the same, or at a similar time, or at different times according to a dosing regimen or schedule. Sequential administration may be in any order, as required, and may require an ongoing physiological effect of the first or initial compound to be current when the second or later compound is administered, especially where a cumulative or synergistic effect is desired.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

In order that the present technology may be more clearly understood, preferred embodiments will be described with reference to the following drawings and examples.

EXAMPLES

Example 1: Injury Induces Myocardial Expression of klf1 During Heart Regeneration in Zebrafish While investigating molecular mechanisms for heart regeneration in zebrafish, the inventors identified an injury-induced, myocardial expression of krüppel-like factor 1 (klf1) (FIG. 1A), the gene encoding the zebrafish ortholog of a zinc finger transcription factor KLF1/EKLF. In mammals, KLF1 is expressed in hematopoietic tissues and essential for erythrocyte development, but a role for KLF1 in non-hematopoietic organs was unclear prior to this study.

Figure 1:
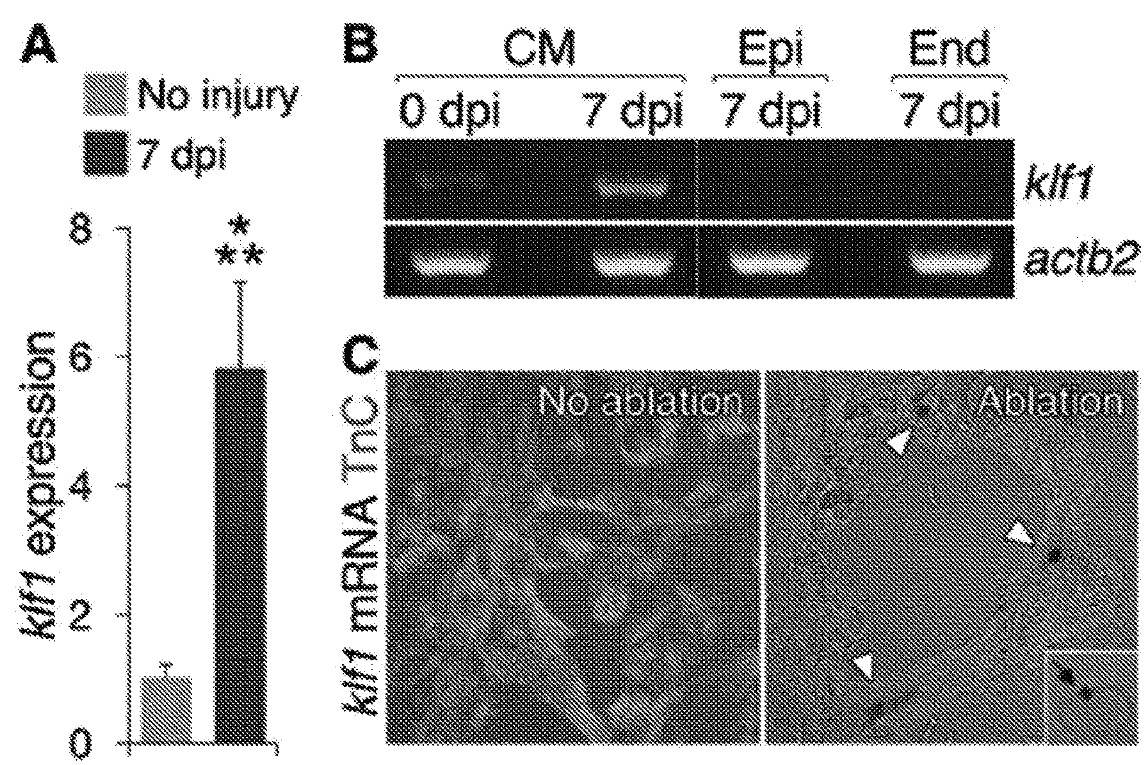
FIG. 1: Klf1 expression during heart regeneration in zebrafish. (A) qPCR analysis of uninjured (No injury) and injured (7 dpi) ventricles. (B) Semi-qPCR. Cardiomyocytes (CM), endocardial cells (End), and epicardial cells (Epi) were purified using fluorescence-activated cell sorting (FACS) from uninjured and 7 days post-injury (dpi) ventricles of Tg(cmlc2:EGFP), Tg(fli1a:EGFP), and TgBAC (tcf21:DsRed2) fish, respectively. (C) RNAScope analysis.

The analysis used quantitative reverse transcriptase polymerase chain reaction (RT-qPCR) to indicate that klf1 expression transiently peaked at 7 days post injury (dpi) (FIG. 1B), corresponding to the maximal response of the regenerative proliferation of cardiomyocytes (CMs). When RT-qPCR was performed with purified cardiac cells obtained from 7 dpi ventricles of cell-type specific reporter lines using fluorescent activated cell sorting (FACS), klf1 transcripts were detected in CMs, but not in epicardial and endocardial cells (FIG. 1B). klf1 expression was also assessed using a genetic CM ablation model, in which 4-hydroxytamoxifen (4-HT) treatment could specifically damage cardiac muscle without causing a bleeding. Using sections of the CM-depleted hearts, the inventors performed highly sensitive in situ hybridization and immunofluorescence against troponin C (TnC), a cytosolic muscle marker, and detected co-localization of klf1 mRNA signals with TnC in the regenerating myocardium (FIG. 1C, arrowheads). These data indicate that injury induces myocardial expression of klf1 during heart regeneration in zebrafish.

Example 2: Klf1 is Essential for Heart Regeneration in Zebrafish

To investigate the function of Klf1 in cardiac regeneration, the inventors established the zebrafish line Tg(actb2:IoxP-TagBFP-STOP-IoxP-dn-klf1)$^{vcc22}$ (hereafter actb2:BS-dn-klf1), in which dominant-negative form of Klf1 (dn-Klf1) is induced in CMs in combination with a cardiac muscle-specific Cre driver line, Tg(cmlc2:CreER) (hereafter, cmlc2:CreER). We treated cmlc2:CreER; actb2:BS-dn-klf1 (KlfDN-ON) and control actb2:BS-dn-klf1 fish (KlfDN-OFF) with 4-HT and analyzed regeneration at 30 dpi. Strikingly, all KlfDN-ON hearts exhibited extremely severe scarring at the wound area (7 out of 7; FIG. 2A), while such a phenotype was not observed with any control KlfDN-OFF hearts (0 out of 7; FIG. 2A). Myocardial expression of dn-Klf1 significantly reduced CM proliferation, as detected by reduced co-labeling of the myonuclear marker Mef2 with PCNA (FIG. 2B). These data indicate that Klf1 is an essential transcription factor for cardiac regeneration in zebrafish.

Using quantitative transcriptional analysis, it was observed that expression of klf1 expression peaked at 7 days post-injury (dpi) (FIG. 3A), concurrently with the period of maximal regeneration-induced proliferation in cardiomyocytes. This transient klf1 expression was restricted to purified cardiomyocytes, and it was not detected in epicardial (Epi) or endocardial cells (End) (FIG. 3B). Using a conditional 4-hydroxytamoxifen (4-HT)-inducible cardiomyocyte ablation model, which damages cardiac muscle without causing a cardiac bleed, co-localization of klf1 mRNA with the cytosolic muscle marker troponin C was observed. This indicates that regenerating myocardial cells express Klf1 during heart regeneration in zebrafish.

Example 3: Klf1 Expression Induces CM Dedifferentiation in the Zebrafish Heart

The transgenic zebrafish line Tg(actb2:IoxP-TagBFP-STOP-IoxP-3×HA-klf1)$^{vcc29}$ was established to overexpress 3×HA-tagged Klf1 in CMs with cmlc2:CreER. Double-transgenic fish and Cre-negative clutch-mates were referred to as klf1-ON and klf1-OFF, respectively. klf1-ON; cmlc2:

GFP and control klf1-OFF; cmlc2:GFP fish were treated with 4-HT and assessed the expression of a dedifferentiation marker Sm22α (Sm22), in CMs labeled with cmlc2:GFP. Strikingly, compared with the control heart (12d klf1-OFF), the level of Sm22 expression was profoundly increased in the Klf1-overexpressed heart, where the expression was initially detected in the outermost myocardium of the ventricle at 7 days post-4-HT treatment (dpt) and later observed also in the inner trabecular myocardium at 12 dpt. The analysis using Tg(gata4:EGFP) (hereafter, gata4:GFP), another dedifferentiation marker in zebrafish CMs, also revealed a similar spatial and temporal pattern of gata4:GFP to that of Sm22. Immunofluorescence of α-actinin, a major component of Z-lines, revealed a highly disorganized sarcomere structure in klf1-ON myocardium compared with that of klf1-OFF myocardium. Moreover, consistent with the histological evidence for CM dedifferentiation, the klf1-ON heart significantly increased the expression of runx1, a stem cell and CM dedifferentiation marker in mouse (FIG. 4A), accompanying with reduced expression of contractile genes such as myosin heavy chain (vmhc), cardiac muscle actin (actc1a), and myomesin (myom2a) (FIG. 4B). These data indicate that Klf1 expression is sufficient to dedifferentiate CMs into a less mature state in the zebrafish heart.

Example 4: Klf1 Expression Induces CM Proliferation in the Zebrafish Heart

Since the reduced contractile state acquired via CM dedifferentiation has been suggested to facilitate cell division, the inventors next addressed whether CM proliferation was enhanced by Klf1 overexpression using EdU incorporation assay. Strikingly, compared with the background level of proliferation ($EdU^+$CMs) in klf1-OFF hearts (FIG. 5A), proliferation in klf1-ON hearts was increased by nearly 200-fold (FIG. 5A). We next assessed CM mitosis by immunofluorescence using an antibody against phospho-Histone H3 (pHH3). Identifying mitotic CMs is extremely difficult even in the regenerating zebrafish heart, likely due to the short period of the mitotic phase in the cell cycle. However, the inventors constantly observed ~6 $pHH3^+$ CMs per section in klf1-ON hearts while no mitotic CMs were detected in control hearts (FIG. 5B), which strongly indicates the potent effect of Klf1 overexpression in CMs for cell cycle re-entry. Consistent with the profoundly elevated level of CM proliferation, klf1-ON heart significantly increased the expression of a broad range of cell cycle regulators such as FoxM1, PCNA, E2F2, Cdc25b, cyclin-dependent kinases (Cdk1/2), and G1/S (CyclinD1) and G2/M cyclins (CyclinB2/A2) (FIG. 5C). Together, these data indicate that Klf1 expression is sufficient to force quiescent CMs to re-enter cell cycle in the adult zebrafish heart.

Example 5: KLF1 Function in the Adult Mouse Heart

Similar to the zebrafish heart, mouse Klf1 (mKlf1) mRNA was upregulated from a baseline level in the regenerating neonatal heart after infarction (Neonate; FIG. 6A). Intriguingly, however, mKlf1 expression was not induced in infracted adult hearts (Adult; FIG. 6A), indicating the correlation of its expression levels with the regenerative capacity of the mouse heart.

To investigate KLF function in the adult mouse heart, the inventors generated a recombinant adenovirus vector in which mKlf1 cDNA is linked to EGFP cDNA via P2A peptide sequence to visualize the infected cells (Ad-Klf1. Also generated was a control vector containing only EGFP cDNA (Ad-GFP). Purified Ad-GFP or Ad-Klf1 viruses were injected into the myocardium of the uninjured heart of adult C57BL/6 mice and assessed CM proliferation by Ki67 immunofluorescence analysis. It was found that the injection of Ad-Klf1 virus significantly increased the co-labeling of Ki67 and Troponin-T (TnT) (KLF1; FIG. 6B), compared with the injection of the control virus (GFP; FIG. 6B). Immunofluorescence detection of GFP indicated the expression of mKlf1 in proliferating CMs.

To confirm this result, the inventors delivered EdU using an osmotic mini-pump and assessed CM proliferation, identifying CMs with a membrane marker wheat germ agglutinin (WGA) in conjunction with immunofluorescence of TnT. This is a more sensitive method to identify proliferating CMs in adult mouse heart sections. Consistent with the result from immunolabeling of Ki67 and TnT, the analysis using WGA staining also detected significantly increased $EdU^+$ CMs in hearts injected with Ad-Klf1 virus (KLF1; FIG. 6C). Together, these data indicate that mKlf1 has a conserved function in CM proliferation in mice and can induce CM cell cycle re-entry in vivo even in the absence of injury.

Klf1 was also delivered to adult mouse hearts after myocardial infarction (MI). Significantly increased CM proliferation (FIG. 7A) and mitosis (FIG. 7B) were also observed with Ad-Klf1 transduction, indicating that mKlf1 has a conserved regenerative function in mice. Consistent with the increased CM renewal, we found that cardiac scarring was remarkably reduced in the hearts with Ad-Klf1 transduction with increased myocardial formation in the damaged area (FIG. 7C) and significant recovery in cardiac function (FIG. 7D). Together, these data indicate that mKlf1 has a conserved function in CM proliferation and regeneration in mice.

Example 6: Conditional Gene Trap Lines

To address the role for Klf1 in heart regeneration, the inventors created a conditional gene trap line, Tg(klf1:Zwitch2)$^{vcc33Gt}$ (referred to as klf1-ct or klf1$^{ct}$ hereafter), by inserting a Cre-dependent gene-trap cassette termed Zwitch2 into the 1st intron of klf1 gene via homologous recombination as previously described (FIG. 8A, B). Zwitch2 consists of a splice-acceptor (SA) site followed by triplet poly-A sequences (3×BGHpA) and a removable lens-specific tag with enhanced green fluorescence protein (EGFP) expression for screening (FIG. 8A). The segment containing SA and 3×BGHpA is flanked by tandem IoxP and Iox5171 sites in opposite orientations, which could permanently invert via Cre-mediated recombination and inactivate klf1 expression via aberrant splicing (Mutagenic; FIG. 8B).

In the established line, the precise insertion of Zwitch2 was verified by genomic PCR, southern blot, and DNA sequencing analysis (FIG. 9A-D). The inventors also characterized the established allele by crossing klf1-ct/+ with Tg(ubb:iCre-P2A-EGFP), a strain in which Cre is expressed by a strong, ubiquitously expressed ubiquitin B (ubb) promoter. Through breeding, we obtained embryos carrying the WT and/or mutagenic klf1 allele (FIG. 9E, F) and analyzed the phenotype of these embryos confirming the evolutionary conserved role of Klf1 in erythrocyte development in zebrafish (FIG. 10A).

The inventors crossed klf1-ct/+ fish with Tg(cmlc2:CreER) (cmlc2:CreER), a strain in which 4 Hydroxytamoxifen (4-HT)-inducible Cre is expressed by regulatory sequences of the contractile gene cardiac myosin light chain 2 (cmlc2/myl7), to inactivate klf1 expression in the myocardium. The inventors obtained klf1-ct/ct and cmlc2:CreER; klf1-ct/ct fish, treated the fish with 4-HT for overnight for 3 consecutive days, and performed resection injury at 2 days after the last treatment. The 4-HT treatment regimen successfully reduced myocardial klf1 expression to a uninjured control level in 7 dpi cmlc2:CreER; klf1-ct/ct ventricles (FIGS. 8C, 9H). CM proliferation was analyzed by immunofluorescence against the myonuclear marker Mef2 and proliferating cell nuclear antigen (PCNA) to identify a significant reduction in the number of proliferating $Mef2^+$, $PCNA^+$ CMs with the inactivation of myocardial expression klf1 (FIG. 8D). Immunofluorescence was performed against fetal CM markers, such as smooth muscle protein 22 alpha (Sm22a; also known as transgelin) (FIG. 8E) and activated leukocyte cell adhesion molecule a (Alcama; also known as DM-GRASP) (FIG. 8F). This significantly reduced expression of these markers in the heart lacking klf1 expression (FIG. 8F). Together, these data indicate that Klf1, while having an important role in erythropoiesis and congenital anaemia, also drives a novel mechanism of CM dedifferentiation and proliferation during heart regeneration in zebrafish.

Details of generation and characterization of $klf1^{ct}$ described (FIG. 9A-D). Global activation of $klf1^{ct}$ with ubiquitously expressed Cre-induced $klf1^{ct}$ activation (FIG. 9E) as well as profound reduction of klf1 expression (FIG. 9F), which leads to cardiac edema due to severe anaemia (FIG. 10A). Tissue-specific activation of $klf1^{ct}$ was achieved in adult myocardium with the cardiomyocyte-restricted Cre line Tg(cmlc2:CreER). This myocardial trap line and cmlc2:CreER-negative control line, referred to as klf1-MT and klf1-CT (FIG. 3C), respectively, were subjected to ventricular resection after 4-HT treatment, which verified induction of a Cre-dependent, cardiac klf1-CT inversion (FIG. 9G) and reduction of ventricular expression of klf1 at 7 dpi to the same levels as those of uninjured controls (FIG. 9H). Inactivation of myocardial klf1 expression significantly increased the proportion of regenerating hearts that exhibited a persistent fibrin and collagenous scar (FIG. 3D), indicating that myocardial Klf1 is required for heart regeneration in zebrafish.

Known cardiomyocyte dedifferentiation markers, such as smooth muscle protein 22α/Transgelin (Sm22; FIG. 3E) and activated leukocyte cell adhesion molecule (Alcam; FIG. 3F), were markedly reduced in the klf1-MT heart. This was accompanied by a significant reduction in the number of proliferating cardiomyocytes double-positive for myocyte enhancer factor 2 (Mef2) and proliferating cell nuclear antigen (PCNA) (FIG. 3G). Similarly, we observed profoundly impaired cardiac regeneration and significant reduction in cardiomyocyte dedifferentiation and proliferation under conditional expression of a dominant-negative form of Klf1 (dn-Klf1; FIG. 11A-D), providing further evidence for an essential role of Klf1 in cardiac regeneration. Taken together, these data identify a novel, non-hematopoietic function of Klf1 in myocardial regeneration, whereby Klf1 plays an essential role in the successful induction of cardiomyocyte dedifferentiation and proliferation.

klf1 was virtually undetectable during cardiac development (one mRNA punctum per 81 ventricular myocardial sections examined). It was tested whether Klf1 has a functional role in the development of the myocardium. Strikingly, in contrast to the anaemic phenotype observed with global inhibition of Klf1 (FIG. 10A, B), neither myocardial $klf1^{ct}$ activation (FIG. 10C) nor myocardial dn-Klf1 overexpression (FIG. 10D) affected cardiac morphogenesis and cardiomyocyte proliferation during development. A similar phenotype was also observed for hearts in which $klf1^{ct}$ activation or dn-Klf1 expression was constitutively induced using the ubiquitously expressed Cre driver when the analysis was performed before cardiac edema occurred (FIG. 10E, F). Together, these data indicate a regeneration-specific role for Klf1 in the myocardium.

Example 8: Klf1 Triggers an Injury-Independent Regenerative Response

To investigate whether enforced klf1 expression induces a regenerative phenotype in uninjured hearts, the inventors used a conditional strategy to drive 3×HA-tagged Klf1 in the myocardium (klf1-ON; FIG. 12A). We treated klf1-ON fish or Cre-negative controls (klf1-OFF; FIG. 12A) with 4-HT overnight (FIG. 12B) and detected nuclear localization of 3×HA-Klf1 in the myocardium by immunofluorescence. In klf1-ON hearts, myocardial expression of Sm22 and Alcam was increased at 7 days post-treatment (dpt) and more so at 12 days post-4-HT treatment (dpt). During myocardial regeneration, cardiomyocyte division is likely facilitated by reduced contractility and is accompanied by the expression of genes associated with an immature proliferative state. Consistent with partial cardiomyocyte dedifferentiation in klf1-ON hearts at 7 dpt, α-actinin, a major component of the Z-line, disordered sarcomeres in cortical layer myocardium were observed and more broadly in trabecular myocardium at 12 dpt. These structural abnormalities were visualized as diffuse Z-disks by transmission electron microscopy (TEM) at 7 and 12 dpt.

To determine whether Klf1-induced cardiomyocyte dedifferentiation is accompanied by increased cardiomyocyte proliferation, the proliferation marker PCNA was examined and fa massive increase in the number of $PCNA^+Mef2^+$ cardiomyocytes in klf1-ON ventricles was observed (FIG. 12C). A profound increase in the incorporation of 5-ethynyl-2'-deoxyuridine (EdU) in klf1-ON cardiomyocytes confirmed that many cardiomyocytes had undergone DNA synthesis (FIG. 12D). Visualization of mitotic phosphohistone $H3^+$ ($pHH3^+$) cardiomyocytes is extremely rare, even in vigorously regenerating zebrafish hearts. However, many $pHH3^+$ cardiomyocytes were detected in klf1-ON ventricles (FIG. 12E), clearly showing that cardiomyocytes successfully proceeded through mitosis to anaphase. Together, these data indicate that klf1 overexpression is sufficient to trigger robust cardiomyocyte dedifferentiation responses and strongly promotes cardiomyocyte cell cycle re-entry and proliferation in uninjured zebrafish hearts.

During the course of the extensive proliferative response observed in klf1-ON hearts, cardiomyocytes genetically labeled with EGFP were restricted to cells of the myocardial lineage and did not contribute to other cardiac cell lineages, such as endocardial or epicardial cells. These data indicate that Klf1 induces cardiomyocyte expansion not by reprogramming mature cardiomyocytes into proliferative, multipotent progenitor cells, but rather by the extensive upregulation of cardiomyocyte self-renewal without affecting lineage plasticity. In klf1-ON hearts, increased numbers of vasculature endothelial cells and epicardial cells were observed (FIG. 13A, B), indicating that myocardial Klf1 expression indirectly stimulates a regenerative program within other cardiac cells.

KLF1 subfamily members KLF2 and KLF4 regulate cardiovascular development and function. We compared the cardiomyogenic capacity of the KLF1 subfamily by expressing the zebrafish KLF2 and KLF4 orthologs, Klf2a, Klf2b, and Klf4 in an inducible manner, as described for klf1-ON (FIG. 12A, B). Notably, the strongest induction of cardiomyocyte mitosis was during Klf1 overexpression (FIG. 13C). Whereas cardiomyocyte mitosis was induced at a moderate level during Klf2b overexpression (FIG. 13C), such induction was negligible with Klf2a and Klf4 overexpression (FIG. 13C). The comparatively high potency of Klf1 compared with its family members, Klf2 and Klf4, demonstrates a unique role of Klf1 in the regulation of adult-specific cardiomyogenic targets.

Mammalian KLF1 possesses a similar domain structure with KLF2 and KLF4, which have a notable function in reprogramming somatic cells into pluripotent stem cells. Although at much lower efficiency than KLF2 and 4, KLF1 can also generate induced pluripotent stem cells with other reprogramming factors, indicating that a mechanism whereby Klf1-induced cardiomyogenesis was mediated through CM reprogramming and progenitor amplification followed by re-differentiation to cardiac muscle. Interestingly, the inventors observed significantly more epicardial cells and vasculature endothelial cells in klf1-ON ventricles, indicating paracrine effects of klf1$^+$ CMs but could also be explained by de novo differentiation from reprogrammed klf1$^+$ CMs. To address an involvement of cell reprogramming, the inventors performed genetic fate-mapping analysis using klf1-ON fish carrying a tamoxifen-dependent indicator transgene, which enabled us to permanently label CMs at the onset of klf1 induction. It was found that the genetically labeled cells, while at a reduced level, still expressed myosin heavy chain (MHC) at 12 dpt and did not express a marker for epicardial and endothelial cells, Raldh2 (retinaldehyde dehydrogenase 2; also known as Aldh1a2), indicating that klf1$^+$ CMs did not change the cell lineage during an extensive proliferation period. Thus, Klf1 overexpression achieved an extensive level of cardiomyogenesis in adult hearts not by reprogramming adult CMs to a proliferative multi-potent cardiac progenitor but by dedifferentiating adult CMs into a proliferative immature state, together with a capacity for promoting growth in neighboring tissues.

Example 9: Klf1-Induced Cardiomyocyte Hyperplasia Drives Cardiac Regrowth

The klf1-ON zebrafish progressively exhibited signs of heart failure, including raised scales (FIG. 14A), lethargy, and rapid breathing that impacted survival by 9 dpt (FIG. 14B). To model a transient therapeutic delivery of Klf1, Tg(cmlc2:3×HA-klf1-ER; cryaa:TagBFP)$^{vcc32}$ (hereafter, klf1-ER) was established. In klf1-ERKlf1 reversibly translocates to the nucleus in response to 4-HT (FIG. 12F).

Treatment with 4-HT once per day for seven days (FIG. 12G) induced nuclear klf1-ER localization and regenerative responses in the ventricles. In contrast to klf1-ON, there was no impact on the survival of klf1-ER fish after the cessation of 4-HT treatment and thus, the inventors analyzed the hearts 30 days later (FIG. 12G), when Klf1-induced responses were quiescent. Of interest, gross analysis of the experimental hearts revealed massive enlargement of the hearts collected from 4-HT-treated klf1-ER fish (FIG. 12H). Sections of the enlarged hearts did not exhibit pathological dilation or fibrosis (FIG. 12I), and the myocardial area was significantly larger (~two-fold; FIG. 12J). The number of Mef2$^+$ nuclei profoundly increased in klf1-ER ventricles, where α-actinin staining clearly displayed a distinct, well organized striated pattern of Z-bands. Moreover, the size of the individual cardiomyocytes in the enlarged ventricles was small (FIG. 12K), therefore, not hypertrophic, but had significantly increased in number by approximately five-fold compared with those in the control ventricles (FIG. 12L). Thus, in just seven-days of Klf1 activation cardiomyocytes multiplied almost five times in uninjured zebrafish hearts, highlighting the extreme pro-proliferative potency of Klf1 in stimulating cardiomyogenesis in adult hearts.

Example 10: Klf1 Induces Chromatin Remodeling to Suppress Myocardial Gene Programs To gain insight into the myocardial function of Klf1, the inventors performed chromatin immunoprecipitation (ChIP) followed by sequencing (ChIP-seq) on klf1-OFF and klf1-ON ventricles using an anti-HA-tag antibody at 7 dpt. 3×HA-Klf1 ChIP peaks were detected specifically in klf1-ON ventricles (FIG. 15A). These peaks were most significantly enriched for the KLF1 motif (FIG. 15B), which validates the specificity of Klf1 purification using the anti-HA antibody. potential target genes under the Klf1 peaks were analyzed with the genomic regions enrichment of annotations tool (GREAT) and identified genes involved in organogenesis pathways including cardiac muscle development (FIG. 15C).

To characterize Klf1 binding sites, ChIP-seq for the active promoter mark (histone H3K4me3) were conducted and the active enhancer marks (histones H3K4me1 and H3K27ac) and plotted the histone peaks obtained relative to the Klf1 peaks (FIG. 15D). Unexpectedly, only a small fraction (98 peaks; 8.6%) of the Klf1 peaks at active promoters were found, and the remaining majority (1,039 peaks; 91.4%) were at active enhancers, which were constitutively marked with H3K27ac and H3K4me1 (FIG. 15D), as well as a reduction in DNA methylation (5-methylcytosine, 5mC; FIG. 15D), regardless of the expression of klf1 or cardiomyogenic responses. Moreover, cross-referencing the inventors data with previously published datasets showed that Klf1-targeted enhancers gained the activated epigenetic profile as early as 48 hours post-fertilization (hpf), and some Klf1 target sites corresponded with the genomic positions of functionally-validated, developmentally-active enhancers from the VISTA enhancer browser. These data indicate that Klf1 preferentially targets developmentally-activated and constitutively-active enhancers in adult cardiomyocytes.

The inventors next assessed a global change in chromatin accessibility in klf1-ON hearts with an assay for transposase-accessible chromatin using sequencing (ATAC-seq). Strikingly, the majority of differentially enriched ATAC peaks were annotated at regions of reduced chromatin accessibility in klf1-ON hearts (FIG. 15E), accompanying the reduction of H3K27ac (FIG. 15F) and transcription of nearby genes (FIG. 15G). Remarkably, regions with reduced accessibility were enriched for binding sites of MEF2C, GATA4, MEF2A, and NKX2.5 (FIG. 15H), which comprise the core cardiac regulatory network controlling cardiac cell fate, structure and morphogenesis, and contractile gene expression. Consistent with this result, pathways regulating cardiac tissue development were most significantly linked to reduced accessibility regions (FIG. 15I). Moreover, RNA-seq analysis of klf1-ON ventricles demonstrated that whereas cardiomyocyte dedifferentiation marker genes were upregulated, myocardial structural and regulatory genes were profoundly downregulated (FIG. 15I). Collectively, these data demonstrate a model for cardiomyocyte dedifferentiation: Klf1 binds to preexisting myocardial enhancers in adult hearts and reduces chromatin accessibility at core cardiac transcription factor binding sites, thereby suppressing genetic programs that control cardiac muscle development and function.

Example 11: Klf1 Upregulates Diverse Cell Cycle Genes to Promote Cardiomyocyte Proliferation and Division Consistent with histological evidence for increased cardiomyocyte proliferation in klf1-ON hearts (FIG. 12D, E), that the inventors found that the majority of gene signatures upregulated with klf1 overexpression were associated with cell cycle machinery (FIG. 16A, B). In klf1-ON hearts, a robust increase in the expression of genes encoding essential regulators of DNA replication, cell cycle, and cytokinesis was observed (FIG. 16C, D). Of note, the inventors identified a profound upregulation of genes encoding many types of cyclins such as cyclin D (ccnd1, ccnd2a, ccnd2b), cyclin E (ccne1, ccne2), cyclin A (ccna2), and cyclin B (ccnb1, ccnb2), as well as cyclin-dependent kinases (cdk1, cdk2), whereas expression of a Cdk inhibitor gene (cdkn1ca) was downregulated. Among these cyclin genes, the inventors detected Klf1 binding regulatory regions of the ccnd1 and ccnd2a genes, demonstrating that Klf1 directly regulates the expression of D-type cyclins.

The inventors also analyzed the interaction of Klf1 with known genetic pathways for adult cardiomyogenesis, such as the Hippo-yes-associated protein (YAP) pathway and the Neuregulin-ErbB2 pathway. Gene-set enrichment analysis with the RNA-seq data of the klf1-ON and klf-OFF hearts was performed and detected significant enrichment of gene signatures of the Hippo pathway (FIG. 19A), but not those of the ErbB pathway (FIG. 19B), with klf1 overexpression. The inventors assessed whether inhibition of these pathways affected cardiomyocyte proliferation in klf1-ON hearts and found that pharmacological inhibition of YAP (FIG. 19C), but not of ErbB (FIG. 19D), significantly reduced cardiomyocyte proliferation in klf1-ON hearts. These findings demonstrate that Klf1 mediates cardiomyocyte proliferation partly through the Hippo-YAP pathway. While the expression of many YAP target genes was increased in klf1-ON hearts, the expression of genes encoding core Hippo pathway components was not significantly changed, and Klf1 peaks were not found in these core component genes (data not shown) and demonstrate that Klf1 activates the Hippo-YAP pathway via an indirect mechanism.

Example 12: Klf1 Induces Metabolic Reprogramming to Support Robust Cardiomyocyte Proliferation The majority of downregulated gene signatures in klf1-ON hearts were related to mitochondrial metabolism and bioenergy production (FIG. 16A, B, E). TEM analysis of klf1-ON myocardium revealed mitochondria with reduced cristae and enlarged matrices (FIG. 16F), a morphological phenotype similar to that of functionally immature mitochondria in embryonic and neonatal mouse hearts. Mitochondrial DNA (mtDNA) content was also significantly reduced in klf1-ON hearts (FIG. 16G), with global downregulation of genes that regulate mitochondrial energy metabolism, such as the tricarboxylic acid (TCA) cycle and oxidative phosphorylation. Major metabolic products of these pathways, such as NADH, NAD+, and ATP, were also significantly reduced in klf1-ON hearts (FIG. 16H-K), providing further evidence for a reduction in mitochondrial energy metabolism during klf1 overexpression. These data indicate that the Klf1 pathway, similar to other cardiogenic pathways, facilitates cardiomyocyte proliferation by attenuating OXPHOS, a major mechanism for cell cycle arrest in postnatal cardiomyocytes.

Klf4 has been shown to control cardiac mitochondrial homeostasis by regulating mitochondrial biogenesis and autophagic clearance. We did not detect significant enrichment of autophagy genes nor an increase of autophagic flux in klf1-ON hearts. Rather, in klf1-ON hearts we found a significant reduction in the expression of nuclear genes that regulate mitochondrial homeostasis and function (FIG. 16L). Of note, we found downregulation of the gene encoding PPARγ coactivator-1α (PGC-1α/PPARGC1a), a master regulatory transcription factor that controls mitochondrial biogenesis and oxidative function (FIG. 16L). We also found Klf1 ChIP peaks in enhancers of the ppargc1a gene and reduction of H3K27ac levels in klf1-ON hearts, indicating a mechanism whereby Klf1 modulates mitochondrial function by directly reducing the expression of ppargc1a.

A switch of energy production from OXPHOS to aerobic glycolysis, known as the Warburg effect, supports highly proliferative cells such as cancer cells and recently has been shown to support myocardial regeneration as well. However, the expression of glycolytic enzyme genes was downregulated in klf1-ON hearts, demonstrating that kfl1-ON cardiomyocytes utilize a different metabolic mechanism to support proliferation. To gain further insight into the metabolic role of Klf1, we analyzed the metabolome of klf1-ON and OFF ventricles at 7 dpt. We found significant reductions of glucose 6-phosphate (FIG. 16M) and lactate, confirming the downregulation of glycolysis in klf1-ON hearts. By contrast, key metabolites of the pentose phosphate pathway (PPP; FIG. 16N, O, Q, S) and the serine synthesis pathway (SSP; FIG. 16P), as well as genes for their regulatory enzymes, were upregulated in klf1-ON hearts, demonstrating that klf1 overexpression leads to the divergence of glucose metabolism from the glycolytic pathway to the PPP and SSP. In cancer, the PPP and SSP play a crucial role in the synthesis of macromolecules (e.g., nucleic acids, amino acids) and antioxidants (e.g., NADPH) to support cell proliferation and growth. Thus, our data indicate that Klf1 induces metabolic rewiring of oxidative respiration pathways to provide the biomass and antioxidant defense required for extensive proliferation of cardiomyocytes.

Example 13: Conserved Regenerative Function of Klf1 in Mouse Hearts

The function of Klf1 in mouse hearts was investigated. Using RT-qPCR, significant upregulation of mouse Klf1 (mKlf1) gene expression in the neonatal mouse heart after myocardial infarction (MI) was detected (FIG. 17A). High-resolution in situ hybridization detected co-localization of mKlf1 mRNA with cardiac troponin T (TnT) staining in the myocardium bordering the infarcted area. These findings indicate that, similar to the zebrafish heart, mKlf1 expression is induced in the neonatal mouse heart upon injury. However, expression of the mKlf1 gene was not significantly upregulated in the adult mouse heart after MI (FIG. 17A), contributing to the loss of regenerative capacity with age.

To address whether mKlf1 expression unlocks regenerative capacity in the adult mouse heart, we induced MI after measuring baseline cardiac function by echocardiography and injected adenoviral vectors carrying either control reporter (Ad-GFP; FIG. 17B) or the mKlf1 construct (Ad-mKlf1; FIG. 17B) into the peri-infarcted myocardium of the MI hearts (FIG. 17C, D). Using echocardiography, we observed a marked reduction in the left ventricular ejection fraction (FIG. 17E) and fractional shortening (FIG. 17F) in both groups at 3 dpi, verifying the induction of MI in these cohorts. In time course echocardiography analysis, cardiac function of the control hearts declined further at 28 dpi (FIG. 17E, F), indicating the development of ischemic heart failure. By contrast, cardiac function of the Ad-mKlf1-treated hearts improved significantly at 7 dpi, recovering to almost 50% of the baseline levels by 14 dpi (FIG. 17E-G), with significant improvement over the control group being maintained at 28 dpi (FIG. 17G, H).

Consistent with these results, histological analysis demonstrated that while the control hearts developed severe cardiac remodeling, the Ad-mKlf1-treated hearts maintained markedly better cardiac morphology (FIG. 17H, I) with significantly less scarring at 28 dpi (FIG. 17H, J). We measured cardiomyocyte cell size, defined by $TnT^+$ areas encapsulated by wheat germ agglutinin (WGA), and found that cardiomyocytes were significantly smaller along the border zone myocardium of the Ad-mKlf1-treated hearts (FIG. 17K), indicating that mKlf1 transduction induces cardiomyocyte hyperplasia. Consistent with this observation, we also found a significant increase in the number of $TnT^+$ cardiomyocytes co-labeled with the cell proliferation marker Ki67 (FIG. 17L), the S-phase marker EdU (FIG. 17M), and the mitosis marker pHH3 (FIG. 17N). The effect of Ad-mKlf1 transduction in the liver, a highly regenerative organ in adult mice was assessed. No significant change in cell proliferation was observed (FIG. 18A), indicating that the pro-regenerative function of Klf1 is specific to the heart. Together, these data demonstrate that, similar to zebrafish Klf1, mouse Klf1 has a pro-regenerative function in adult hearts and induces repair in post-MI hearts.

These data indicate that pro-survival pathways are unlikely to play a major role in the recovery of post-MI hearts with Ad-mKlf1 injection. Similar to the observation of increased vasculature in klf1-ON hearts of zebrafish (FIG. 13A), significantly more coronary vessels near the wound areas of Ad-mKlf1 treated hearts in mice were observed (FIG. 18B). These data indicate that, similar to the zebrafish heart, activation of the Klf1 pathway in the mouse heart stimulates a regenerative program that also involves the coronary vasculature, and the increase vascularity, at least in part, contributes to better repair with Klf1 overexpression. Collectively, our data indicate that the myocardial role of Klf1 is dampened in adult mammals but that administration of exogenous Klf1 re-initiates cardiac regeneration, thus KLF1 is a suitable treatment strategy to restore cardiac muscle from within the spared myocardium of damaged human hearts.

Example 14: Methods 14.1 Animals

Wild-type and genetically modified zebrafish of the outbred Ekkwill (EK) background strain ranging in age from 4 to 12 months were used in this study. All transgenic strains were analyzed as hemizygotes, except the klf1d line. Published transgenic lines used in this study are as follows:

- Tg(cmlc2:EGFP)—Burns, C. G. et al. *Nat Chem Biol* 1, 263-264 (2005),
- TgBAC(tcf21:DsRed2)—Kikuchi, K. et al. *Development* 138, 2895-2902 (2011),
- Tg(fli1a:EGFP)—Lawson, N. D. & Weinstein, B. M. *Dev Biol* 248, 307-318 (2002),
- Tg(cmlc2:CreER)—Kikuchi, K. et al., et al. *Nature* 464, 601-605 (2010),
- Tg(bactin2:IoxP-mCherry-STOP-IoxP-DTA176)—Wang, J. et al. *Development* 138, 3421-3430 (2011),
- Tg(gata4:EGFP)—Heicklen-Klein & Evans. *Dev Biol* 267, 490-504 (2004), and
- Tg(ubb:iCRE-GFP)—Sugimoto, K. et al *Elife* 6, e24635 (2017).

Details of the generation of new transgenic strains are described below. Fish were housed at approximately five fish per liter and fed three times daily. Water temperature was maintained at 28° C. Resection injury was performed on zebrafish anesthetized with tricaine as previously described (Poss, K. D., Wilson, L. G. & Keating, M. T. *Science* 298, 2188-2190 (2002)). Genetic cardiomyocyte depletion was performed as described (Wang, J. et al. *Development* 138, 3421-3430 (2011)).

Male C57BL/6J mice ranging from 8 to 12 weeks of age were used in this study. Mice were housed at a maximum of five mice per cage in racks in a 12:12 hr light-dark cycle and given ad libitum access to food and water. All animal experiments were performed in accordance with institutional and national animal ethics guidelines and approved by Garvan Institute of Medical Research/St Vincent's Hospital Animal Ethics Committee.

14.2 Myocardial Infarction

MI was performed on mice anesthetized by intraperitoneal injection of xylazine (13 mg/kg) and ketamine (100 mg/kg), as previously described (Naqvi, N. et al. *Cell* 157, 795-807 (2014)). Anesthetized mice were ventilated using a mini-vent ventilator (Harvard Apparatus, Hollistion, Mass, USA) with 1.5%-2% isoflurane in oxygen (0.5 mL stroke volume at 120 strokes per minute). The fourth rib space was opened, the left anterior descending (LAD) artery permanently ligated using an 8-0 prolene suture on a tapered needle, and the chest was closed with 6-0 prolene sutures.

14.3 Generation of actb2:BS-klf1, klf2a, klf2b, and klf4

TagBFP cDNA was PCR-amplified from pTagBFP-C (Evrogen, Moscow, Russia), and 3×HA-tag was synthesized using Ultramer Oligo Synthesis (IDT Technologies, Coralville, IA, USA). The DsRed and EGFP of the actb2:IoxP-DsRed-STOP-IoxP-EGFP construct (Kikuchi, K. et al., et al. *Nature* 464, 601-605 (2010)) were replaced with TagBFP and 3×HA-tag, respectively. Klf1, Klf2a, Klf2b, and Klf4 cDNAs were amplified by PCR using wild-type (Ekkwill) zebrafish cDNA libraries and cloned downstream and in-frame with the 3×HA-tag. In each construct, the entire cassette was flanked with I-SceI sites for transgenesis using the meganuclease method (Thermes, V. et al. *Mech Dev* 118, 91-98 (2002).). The full name of these transgenic lines are as follows: Tg(actb2:IoxP-TagBFP-STOP-IoxP-3×HA-klf1)$^{vcc29}$; Tg(actb2:IoxP-TagBFP-STOP-IoxP-3×HA-klf2a)$^{vcc36}$; Tg(actb2:IoxP-TagBFP-STOP-IoxP-3×HA-klf2b)$^{vcc38}$; and Tg(actb2:IoxP-TagBFP-STOP-IoxP-3×HA-klf4)$^{vcc35}$. At least two founder lines were isolated for each line and crossed with cmlc2:CreER to examine the expression of Klf1, Klf2a, Klf2b, and Klf4 proteins in adult hearts by immunofluorescence staining against 3×HA-tag. Lines that express 3×HA-Klf2a, Klf2b, or Klf4 at a similar or higher level than that of 3×HA-Klf1 were used for this study.

14.4 Generation of actb2:BS-dn-klf1

A dominant-negative form of Klf1 was generated using an engrailed repressor domain (EnR) based on a strategy employed for the construction of a dominant-negative form of Klf5 (Oishi, Y. et al. *Cell Metab* 1, 27-39 (2005)).

The EnR was PCR-amplified from pCS2-EnR and fused in-frame with the 5' end of Klf1 cDNA. The p026 pCS2-EnR was a gift from Dr. Ramesh Shivdasani (Addgene plasmid #11028; http://n2t.net/addgene:11028; RRID: Addgene_11028). The resulting EnR-Klf1 chimeric gene was cloned downstream of the IoxP-flanked STOP cassette of an actb2:IoxP-TagBFP-STOP-IoxP backbone construct. The entire cassette was flanked with I-SceI sites for transgenesis using the meganuclease method. The full name of this transgenic line is Tg(actb2:IoxP-TagBFP-STOP-IoxP-dn-klf1)$^{vcc22}$.

14.5 Generation of ubb:IoxP-TagBFP-STOP-IoxP-EGFP

This transgenic construct was generated by inserting the IoxP-TagBFP-STOP-IoxP-EGFP cassette into the CH211-202A12 BAC after the ubb translational start codon using Red/ET recombineering (GeneBridges, Heidelberg, Germany). The final construct was purified, linearized with SfiI, and injected into single-cell-stage embryos. The full name of this transgenic line is TgBAC(ubb:IoxP-TagBFP-STOP-IoxP-EGFP)$^{vcc18}$.

14.6 Generation of klf1-ER

3×HA-Klf1 cDNA was PCR-amplified from the actb2:BS-klf1 construct and subcloned downstream of the 5.1 kb cmlc2 promoter. Human estrogen receptor (ER) cDNA was PCR-amplified from pBabepuro-myc-ER and subcloned downstream and in-frame with 3×HA-Klf1. pBabepuro-myc-ER was a gift from Wafik EI-Deiry (Addgene plasmid #19128; http://n2t.net/addgene:19128; RRID:Addgene_19128). A TagBFP cassette controlled by the lens-specific alpha A-crystallin promoter, which enables visual identification of transgenic animals by lens fluorescence, was also inserted upstream of the cmlc2 promoter in the opposite orientation. The entire cassette was flanked with I-SceI sites for transgenesis using the meganuclease method. The full name of this transgenic line is Tg(cmlc2:3×HA-klf1-ER; cryaa: TagBFP)$^{vcc32}$.

14.7 Generation of the Conditional klf1 Allele

The published plasmid pZwitch was modified to reduce its size by removing the TagRFP sequence and two repeats of 5×BGHpA. The resulting plasmid was referred to as pZwitch2. The LA and RA of the homology sequences were amplified from genomic DNA isolated from adult wild-type zebrafish (EK) using LA amplification primers klf1-LA-F and klf1-LA-R and RA amplification primers klf1-RA-F and klf1-RA-R. The LA and RA PCR products were cloned into the corresponding restriction enzyme sites in pZwitch2 via restriction enzyme digestion. The resulting product, pZwitch2-klf1-int1, was co-injected with transcription activator-like effector nucleases (TALENs) into one-cell-stage embryos, and injected embryos were screened to identify founder fish as described previously (Sugimoto, K. et al *Elife* 6, e24635 (2017)). The full name of this transgenic line is Tg(klf1:Zwitch2)$^{vcc33Gt}$.

The TALEN kit used for constructing Platinum TALENs was a gift from Dr. Takashi Yamamoto (Addgene kit #1000000043). Southern blotting was performed using a probe radioactively labeled with a Prime-a-Gene Labeling System (Promega, Madison, WI, USA). The detection probe was generated using PCR with wild-type genomic DNA and the amplification primers klf1-probe-F and klf1-probe-R (Supplementary Table 1). DNA bands were imaged on a FLA-5100 Bio-Imaging Analyzer (FujiFilm, Tokyo, Japan).

14.8 RT-PCR

Total RNA was extracted using TRIzol reagent, and cDNA was subsequently synthesized either with the Transcriptor first strand cDNA synthesis kit (Roche, Basel, Switzerland) or SensiFAST cDNA Synthesis Kit (Bioline, Eveleigh, Australia). RT-qPCR was performed using a LightCycler 480 System (Roche) or a CFX384 Touch Real-Time PCR Detection System (Bio-Rad, Hercules, CA, USA). The total amount of cDNA was normalized to actb2 or rpl13a amplification in RT-qPCR experiments. All RT-qPCR assays were performed using SYBR Select Master Mix (Thermo Fisher Scientific, Waltham, MA, USA) or TaqMan Universal Master Mix (Thermo Fisher Scientific). See Supplementary Table 1 for details of the primers.

14.9 Cell Sorting

Cardiomyocytes, endocardial cells, and epicardial cells were purified from ventricles of transgenic reporter zebrafish carrying cmlc2:EGFP, tcf21:DsRed2, or fli1a:EGFP, respectively, using fluorescence-activated cell sorting (FACS) as described (Hui, S. P. et al. *Dev Cell* 43, 659-672.e5 (2017)).

14.10 In Situ Hybridization

Zebrafish klf1 and mouse Klf1 mRNAs were detected using RNAscope probes (Advanced Cell Diagnostics, Hayward, CA, USA). The zebrafish klf1 and mouse Klf1 RNAscope probes were designed and synthesized by Advanced Cell Diagnostics. The manufacturer's protocol for RNAscope 2.5 HD Detection Kit-Red (Advanced Cell Diagnostics) was used to detect the signals, followed by immunofluorescence using anti-troponin C or anti-troponin T antibodies. Imaging was performed with a Zeiss LSM 710 confocal microscope as described (Hecksher-Sørensen, J. & Sharpe, J. *Mech Dev* 100, 59-63 (2001)).

14.11 Histological Assays

Picro-Mallory staining, 3,3'-Diaminobenzidine (DAB) staining, and Gomori-trichrome staining were performed using standard protocols. Immunofluorescence was performed in paraformaldehyde-fixed 10 μm cryosections as described previously (Hui, S. P. et al. *Dev Cell* 43, 659-672.e5 (2017)). Supplementary Table 2 shows details of primary and secondary antibodies used in this study. Hemoglobin staining in embryos was performed using o-Dianisidine (Sigma Aldrich, St. Louis, MO, USA) as described by Detrich et al. *Proc Natl Acad Sci USA* 92, 10713-10717 (1995).

14.12 Microscopes

Sections stained by the Picro-Mallory, DAB, or Gomori-trichrome methods were imaged on a Leica DM4000 B microscope (Leica Camera AG, Wetzlar, Germany). Immunofluorescent sections were imaged using a Zeiss AXIO imager M1 microscope (Carl Zeiss AG, Oberkochen, Germany), and confocal images were taken with a Zeiss LSM 710 confocal microscope (Carl Zeiss AG). Whole-mount images of zebrafish embryos were taken with an MVX10 microscope (Olympus, Tokyo, Japan).

14.13 Transmission Electron Microscopy

Zebrafish ventricles were fixed with 2.5% glutaraldehyde in 0.1 M sodium cacodylate buffer and re-fixed with fresh fixative solution in a PELCO BioWave microwave processor (Ted Pella Inc., Redding, CA, USA). Post-fixation was carried out with 1% $OsO_4$ in cacodylate buffer. Tissues were embedded with Procure 812 resin (ProSciTech, Kirwan, Australia) and sectioned using a Leica Ultracut EM UC6 (Leica Camera AG). Ultrathin sections were collected onto copper grids and imaged at 200 kV on an FEI Tecnai $G^2$ 20 transmission electron microscope (FEI company, Hillsboro, OR, USA).

14.14 4-HT Administration

Zebrafish were placed in a small beaker of aquarium water supplemented with 5 μM 4-HT for 10-12 h overnight as described (Kikuchi, K. et al. *Development* 138, 2895-2902 (2011)). Zebrafish were rinsed with fresh aquarium water and returned to the recirculating water system for feeding. This cycle was repeated for multiple treatments. Zebrafish embryos were treated similarly, except they were not fed.

14.15 EdU Assay klf1-OFF and ON fish were intraperitoneally injected with 50 μL of 8 mM EdU once daily at 5, 6, and 7 days after 4-HT treatment. For mice, an osmotic minipump (ALZET, Charles River, MA, USA) was subcutaneously implanted one week after MI surgery, and EdU was infused at 10 mg/kg each day for seven days.

14.16 Quantification of Mocardial Dedifferentiation

Zebrafish ventricular tissues co-labeled with myosin heavy chain (MHC) and Sm22 were quantified in pixels by ImageJ (NIH, Bethesda, MD, USA). Total $MHC^+$ areas were also quantified in pixels, and the percentages of $Sm22^+$ $MHC^+$ areas per total $MHC^+$ areas were determined. Three selected sections were analyzed for each heart. Myocardial expression of Alcam was quantified similarly, except that troponin C was used as a marker for myocardium.

14.17 Quantification of Cardiomyocyte Proliferation in Zebrafish Hearts $PCNA^+$ cardiomyocytes were quantified in injured hearts as described previously (Hui, S. P. et al. *Dev Cell* 43, 659-672.e5 (2017)). Briefly, images of the injury border zone area were taken using a Zeiss AXIO imager M1 microscope (approximately 185 μm vertically), and the numbers of $Mef2^+$ and $Mef2^+PCNA^+$ cells were manually counted using ImageJ software (NIH). Three selected sections were analyzed for each heart. Quantification in uninjured ventricles was performed similarly, except that images of the mid-ventricular myocardium (490 μm vertically×420 μm horizontally) were used for quantification.

To quantify $EdU^+$ cardiomyocytes in uninjured zebrafish ventricles, confocal images of the mid-ventricular myocardium (490 μm vertically×420 μm horizontally) were taken with z-stacks spanning the entire myocardial thickness. The numbers of $EdU^+$ nuclei embedded within cmlc2:$EGFP^+$ myocardium were manually counted and normalized to the total cmlc2:$EGFP^+$ areas that were quantified using ImageJ software (NIH). Three selected sections were analyzed for each heart. Quantification of $pHH3^+$ cardiomyocytes was performed similarly, except that $pHH3^+$ nuclei within the entire ventricle were counted.

14.18 Quantification of Cardiomyocyte Proliferation in Mouse Hearts

For quantification of $Ki67^+$ cardiomyocytes, cross-sectional images of the areas adjacent to the scar tissue were taken at the papillary muscle level. The number of $Ki67^+$ nuclei in the injury border zone myocardium, which was defined as healthy myocardium in the areas within a distance of approximately 700 μm from the scar, were counted manually. $Ki67^+$ nuclei surrounded by WGA staining were defined as non-cardiomyocytes and excluded from counting (Ang, K. L. et al. *Am J Physiol Cell Physiol* 298, C1603-9 (2010)). Numbers were normalized to the total troponin $T^+$ areas that were quantified using ImageJ software (NIH). Quantification of $EdU^+$ cardiomyocytes or $pHH3^+$ cardiomyocytes was performed similarly.

14.19 Cardiomyocyte Number and Size Measurements

Cardiomyocyte numbers in zebrafish embryos were quantified as previously described (Sugimoto, K. et al *Elife* 6, e24635 (2017)). Cardiomyocyte numbers in adult hearts were measured as follows. Ventricles were briefly fixed in 3% PFA for 5 min and incubated in PBS with 1 mg/mL collagenase type 4 (Worthington Biochemical, Lakewood, NJ, USA) at 4° C. overnight. Dissociated cells were resuspended in PBS, and rod-shaped cells with defined edges and clear striations were counted manually as cardiomyocytes using a hemocytometer.

To measure cardiomyocyte size, zebrafish ventricles were fixed in 3% PFA for 5 min and incubated in PBS supplemented with 1 mg/mL collagenase type 4 (Worthington Biochemical) at 4° C. overnight. After dissociating cardiac cells by gentle pipette trituration, cells were resuspended in PBS and deposited onto a slide using a Cyto-Tek Cytocentrifuge (Sakura Finetek, Tokyo, Japan), followed by immunofluorescence using an anti-α-actinin antibody (Supplementary Table 2). Confocal images of α-$actinin^+$ cells were used to measure the size of each cardiomyocyte using ImageJ software (NIH).

14.20 Ventricular Area Measurement

Sections of adult zebrafish ventricles underwent Picro-Mallory staining, and ventricular muscle areas were quantified using ImageJ software (NIH). Three selected sections were analyzed for each heart.

Example 15: Summary

This present disclosure provides a function for Klf1 in the regenerative plasticity of adult cardiomyocytes. Despite the similarity of its domain architecture to that of Klf4, Klf1 regulates cardiomyocyte plasticity with an entirely distinct mechanism from the known function of Klf4 in cell reprogramming. Klf4 has the capacity to bind methylated DNA and targets silent chromatins as a pioneer factor to induce the expression of pluripotency genes. By contrast, Klf1 associates with hypomethylated, constitutively active myocardial enhancers and reduces chromatin accessibility at the binding sites for the core transcription factors that regulate myocardial development and function. Recently, genome-wide reduction of active chromatin has been shown to occur during cardiomyocyte renewal in zebrafish. The data presented herein supports this finding and further demonstrates that Klf1 plays a key role in the global repression of myocardial gene programs that trigger cardiomyocyte dedifferentiation.

The data presented herein indicate that Klf1 induces cardiomyocyte proliferation partly through YAP (FIG. 19A, C). Myocardial activation of YAP is regulated by mechanical signals resulting from cytoskeletal and sarcomeric changes. Klf1 may activate Hippo signaling as a consequence of the reduction in sarcomeres induced by the downregulation of genes controlling cardiac muscle contraction and actin cytoskeleton organization (FIG. 15H, I). The motif analysis of Klf1 ChIP-seq identified enrichment for the binding site of the YAP cofactor, TEA domain transcription factor 4 (TEAD4) (FIG. 15B), indicating that one mechanism for the action involves Klf1 regulating the Hippo pathway through association with a YAP-TEAD4 complex in the nucleus.

Klf1 induces metabolic reprogramming of adult cardiomyocytes from cellular respiration pathways to the pentose phosphate pathway (PPP) and serine synthesis pathway (SSP). These upregulate the synthesis of macromolecules and antioxidants to help klf1-ON cardiomyocytes undergo extensive proliferation, indicating the potential to target these pathways in cardiomyocyte renewal therapies. However, the PPP and SSP do not produce ATP, and the continuous activation of these pathways likely leads to energy deprivation (FIG. 16K) and fatal cardiac dysfunction (FIG. 14A, B).

The invention claimed is:

1. A method for inducing cardiomyogenesis comprising administering a therapeutically effective amount of a Krüppel-like transcription factor 1 (KLF1) to a cardiomyocyte, or inducing expression of the KLF1 in the cardiomyocyte, and wherein:

(i.) the KLF1 protein has KLF activity; and (ii.) the KLF1 protein comprises the amino acid sequence of SEQ ID NO: 1, 11, or 12.

2. The method of claim 1, wherein the cardiomyocyte is a cardiomyocyte from an infant, child, or adult.

3. The method of claim 1, wherein the method is carried out in vitro, ex vivo, or in vivo.

4. The method of claim 1, wherein the cardiomyocyte is present in a subject, and wherein the subject has a cardiac condition associated with cardiomyocyte loss selected from myocardial infarction, ischemic cardiomyopathy, dilated cardiomyopathy, or heart failure.

5. The method of claim 4, wherein the KLF1 is administered to the subject, or to the heart of the subject.

6. The method of claim 4, wherein the cardiomyogenesis facilitates cardiac regeneration in the subject.

7. The method of claim 6, wherein the cardiac regeneration is characterized by an increase in one or more of an ejection fraction, a fractional shortening, an increase in vascular endothelial cells, or an increase in epicardial cells.

8. The method of claim 1, wherein the KLF1 induces dedifferentiation of the cardiomyocyte to produce proliferative cardiomyocytes, and wherein the proliferative cardiomyocytes are mitotic.

9. The method of claim 8, further comprising allowing the proliferative cardiomyocytes to proliferate in the presence of the KLF1 to produce a population of proliferative cardiomyocytes.

10. The method of claim 8, wherein the proliferative cardiomyocytes preferentially metabolize glucose using the pentose phosphate pathway, the serine synthesis pathway, or both pathways.

11. The method of claim 9, further comprising allowing differentiation of the population of proliferative cardiomyocytes to produce a population of cardiomyocytes.

12. The method of claim 11, wherein the differentiation occurs in the substantial absence of the KLF1, or after the induction of KLF1 has ceased.

13. The method of claim 8, wherein the KLF1 induces chromatin remodeling to facilitate the dedifferentiation.

14. The method of claim 8, wherein the proliferative cardiomyocytes are cardiomyocyte progenitor cells, immature cardiomyocytes, or cardiomyocytes with embryonic phenotype.

15. The method of claim 1, wherein the cardiomyogenesis does not involve reprogramming the cell lineage of the cardiomyocytes.

16. The method of claim 8, wherein the proliferative cardiomyocytes re-enter the cell cycle.

17. The method of claim 4, wherein the subject has a cardiac condition associated with cardiomyocyte loss.

18. The method of claim 17, wherein the cardiac condition is myocardial infarction, ischemic cardiomyopathy, dilated cardiomyopathy, or heart failure.

* * * * *